United States Patent
Ootsuki et al.

(10) Patent No.: US 8,354,147 B2
(45) Date of Patent: Jan. 15, 2013

(54) POLYMERIZABLE LIQUID CRYSTAL COMPOUND, COMPOSITION AND POLYMER

(75) Inventors: Daisuke Ootsuki, Ichihara (JP); Tomohiro Yano, Ichihara (JP)

(73) Assignees: JNC Corporation, Tokyo (JP); JNC Petrochemical Corporation, Tokyo (JP)

( * ) Notice: Subject to any disclaimer, the term of this patent is extended or adjusted under 35 U.S.C. 154(b) by 189 days.

(21) Appl. No.: 12/819,028

(22) Filed: Jun. 18, 2010

(65) Prior Publication Data
US 2011/0001088 A1 Jan. 6, 2011

(30) Foreign Application Priority Data
Jul. 3, 2009 (JP) ................................. 2009-158517

(51) Int. Cl.
C09K 19/34 (2006.01)
C07D 303/08 (2006.01)
C07D 303/12 (2006.01)

(52) U.S. Cl. .................... 428/1.1; 252/299.61; 549/554; 549/559; 549/562

(58) Field of Classification Search .................... 428/1.1; 252/299.61; 549/510, 555, 560, 561, 554, 549/559, 562
See application file for complete search history.

(56) References Cited

U.S. PATENT DOCUMENTS

| | | | | |
|---|---|---|---|---|
| 5,543,075 | A | 8/1996 | Parri et al. | 252/299.66 |
| 5,622,648 | A | 4/1997 | Parri et al. | 252/299.66 |
| 5,770,107 | A | 6/1998 | Hassal et al. | 252/299.6 |
| 5,773,178 | A | 6/1998 | Shiota et al. | 430/20 |
| 6,660,344 | B2 | 12/2003 | Lub | 428/1.1 |
| 2003/0111640 | A1 | 6/2003 | Lub | 252/299.61 |

FOREIGN PATENT DOCUMENTS

| | | |
|---|---|---|
| JP | 07-017910 | 1/1995 |
| JP | 09-316032 | 12/1997 |
| JP | 10-100247 | 4/1998 |
| JP | 2004-510785 | 4/2004 |
| WO | WO 94/08268 A1 | 4/1994 |

OTHER PUBLICATIONS

J. Mallon et al., "Synthesis and Characterization of Novel Epoxy Monomers and Liquid Crystal Thermosets" Journal of Polymer Science: Part A: Polymer Chemistry, vol. 31, pp. 2249-2260, 1993.
S. Jahromi et al., "Synthesis and photoinitiated polymerization of liquid crystalline diepoxides" Polymaer, vol. 35, No. 3, pp. 622-629, 1994.

*Primary Examiner* — Shean C Wu
(74) *Attorney, Agent, or Firm* — Hogan Lovells US LLP

(57) ABSTRACT

The purpose of the invention is to provide a polymerizable liquid crystal compound that has a liquid crystal phase with a wide temperature range, has an excellent compatibility with another polymerizable liquid crystal compound, has an excellent solubility in organic solvent and is polymerizable in air by heat or light.
Means for Solving the Subject
A polymerizable liquid crystal compound represented by formula (1) wherein $A^1$ and $A^2$ are a ring such as 1,4-cyclohexylene and 1,4-phenylene; $Z^1$ to $Z^3$ are a bonding group such as a single bond and —O—, m is an integer of 1 to 5; $Q^1$ and/or $Q^2$ are —O(C$_2$H$_4$O)$_{n1}$(C$_3$H$_6$O)$_{n2}$— or —O(C$_3$H$_6$O)$_{n2}$(C$_2$H$_4$O)$_{n1}$—, where n1 and n2 are integer of 0 to 5 and the sum of n1 and n2 is 2 to 5; one of $Q^1$ and $Q^2$ may be alkylene; $P^1$ and $P^2$ are a polymerizable group represented by any one of formula (2-1) to formula (2-3) and R is hydrogen, halogen or alkylene having 1 to 5 carbons.

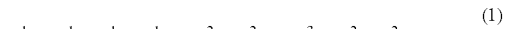

(1)

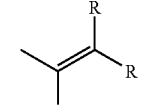

(2-1)

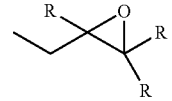

(2-2)

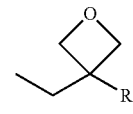

(2-3)

8 Claims, No Drawings

POLYMERIZABLE LIQUID CRYSTAL COMPOUND, COMPOSITION AND POLYMER

BACKGROUND OF THE INVENTION

1. Field of the Invention

The invention relates to a polymerizable liquid crystal compound, a liquid crystal composition including the compound and a polymer of the compound or the liquid crystal composition including the compound.

2. Related Art

A polymerizable liquid crystal compound has recently been utilized for an optically anisotropic substance such as a polarizing plate and an optical retardation plate. This is because the compound exhibits optical anisotropy in the liquid crystal state and then the liquid crystal molecules in this state are fixed fixed by polymerization. The kinds of optical characteristics required for a polymer having optical anisotropy depends on a purpose for use, and a compound having characteristics that suits the purpose is necessary. In the compound used for such a purpose, characteristics regarding its polymer are important in addition to the characteristic of optical anisotropy. The characteristics of the polymer include the rate of polymerization, transparency, mechanical strength, applicability, solubility, the degree of crystallinity, shrinkage, water permeability, water absorptivity, melting points, glass transition temperature, clearing points, chemical resistance and thermal resistance.

A compound having an acryloyloxy group as a polymerizable group among polymerizable liquid crystal compounds is used for such purposes (patent document Nos. 1 and 2). The acrylate has a high reactivity and the polymer derived from it has a high transparency. However, it is necessary to carry out the reaction in an atmosphere of an inert gas and to increase energy of ultraviolet irradiation, because the mode of polymerization is radical polymerization. Thus, an improvement of workability on curing in air and also of characteristics such as heat resistance, shrinkage, adhesive properties, adhesion and mechanical strength is required. Furthermore, a polymerizable liquid crystal compound (or its composition) is used for ink that is diluted with an organic solvent for the purpose of adjusting applicability. The ink in which the viscosity, the leveling properties and so forth are adjusted is prepared by dissolution of a polymerizable liquid crystal compound (or its composition), a photopolymerization initiator, a surfactant and so forth in an organic solvent when a film having optical anisotropy is produced from a polymerizable liquid crystal compound (or its composition). The ink is applied to a transparent substrate film aligned, the solvent is dried, and then the polymerizable liquid crystal compound (or its composition) is oriented. Next, the compound is polymerized with ultraviolet irradiation or heat and the aligned state is fixed. However, the compounds disclosed in non-patent documents Nos. 1 and 2 have subjects that should be solved in view of environmental load and safety (mutagenicity and toxicity), wherein solubility in an organic solvent such as propylene glycol monoethyl ether acetate (PGMEA) that is highly safe is low and thus a suitable concentration of the ink can not be achieved.

Conventional compounds are disclosed in the following patent documents: No. 1, JP H07-017910 A (1995) and No. 2, JP H09-316032 A (1997).

Conventional compounds are also disclosed in the following non-patent documents: No. 1, Polymer Chemistry, 1993, 31(9), 2249-60 and No. 2, Polymer, 1994, 35(3), 622-9.

SUMMARY OF THE INVENTION

The invention concerns a polymerizable liquid crystal compound according to the following item 1 and a composition including the compound, and also an optically anisotropic film derived from the compound or the composition and a liquid crystal display device containing the film.

[1] A polymerizable liquid crystal compound represented by formula (1):

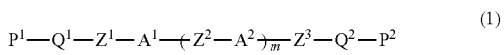

wherein $A^1$ and $A^2$ are each independently 1,4-cyclohexylene, 1,4-phenylene, pyridine-2,5-diyl, pyrimidine-2,5-diyl, naphthalene-2,6-diyl, tetrahydronaphthalene-2,6-diyl or fluorene-2,7-diyl; one or two nonadjacent —$CH_2$— in the 1,4-cyclohexylene may be replaced by —O—; arbitrary hydrogen in the 1,4-phenylene and fluorene-2,7-diyl may be replaced by fluorine, chlorine, cyano, methyl, ethyl, methoxy, hydroxy, formyl, acetoxy, acetyl, trifluoroacetyl, difluoromethyl or trifluoromethyl;

$Z^1$, $Z^2$ and $Z^3$ are each independently a single bond, —O—, —COO—, —OCO—, —CH=CH—COO—, —OCO—CH=CH—, —OCO—$CH_2CH_2$—, —$CH_2CH_2$—COO—, —C≡C—COO—, —OCO—COO—, —$CH_2$O—, —$OCH_2$—, —$CF_2$O—, —$OCF_2$—, —CONH—, —NHCO—, —$(CH_2)_4$—, —$CH_2CH_2$—, —$CF_2CF_2$—, —CH=CH—, —CF=CF— or —C≡C—;

m is an integer 1 to 5; a plurality of $Z^2$ may be different groups or at least two in a plurality of $Z^2$ may be the same groups and a plurality of $A^2$ may be different rings or at least two in a plurality of $A^2$ may be the same rings when m is 2 or more;

$Q^1$ and $Q^2$ are each independently alkylene having 1 to 20 carbons, —$O(CH_2CH_2O)_{n1}(CH_2CH_2CH_2O)_{n2}$— or —$O(CH_2CH_2CH_2O)_{n1}$—; arbitrary hydrogen in the alkylene may be replaced by fluorine or chlorine; in the alkylene, one —$CH_2$— may be replaced by —O— and one or two nonadjacent —$CH_2$— may be replaced by —COO—, —OCO—, —CH=CH— or —C≡C— when the number of carbon is 2 or more; n1 and n2 are each independently an integer of 0 to 5 and the sum of n1 and n2 is 2 to 5; at least one of $Q^1$ and $Q^2$ is —$O(CH_2CH_2O)_{n1}(CH_2CH_2CH_2O)_{n2}$— or —$O(CH_2CH_2CH_2O)_{n2}(CH_2CH_2O)_{n1}$— and $Z^1$ is a single bond when $Q^1$ is —$O(CH_2CH_2O)_{n1}(CH_2CH_2CH_2O)_{n2}$— or —$O(CH_2CH_2CH_2O)_{n2}(CH_2CH_2O)_{n1}$—, $Z^3$ is a single bond when $Q^2$ is —$O(CH_2CH_2O)_{n1}(CH_2CH_2CH_2O)_{n2}$— or —$O(CH_2CH_2CH_2O)_{n2}(CH_2CH_2O)_{n1}$—; and $P^1$ and $P^2$ are each independently a polymerizable group represented by any one of formula (2-1) to formula (2-3):

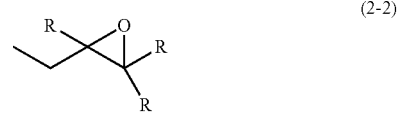

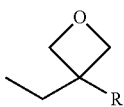

(2-3)

wherein R is independently hydrogen, halogen or alkyl having 1 to 5 carbons.

DETAILED DESCRIPTION OF THE INVENTION

The terms used in the invention will be explained first. The meaning of the term "liquid crystal" in this specification is not limited to characteristics having a liquid crystal phase, and includes also characteristics in which a compound can be used as a component of a liquid crystal composition when mixed with another liquid crystal compound, even though the compound itself does not have a liquid crystal phase. The compound represented by formula (1) may be abbreviated to "the compound (1)", and the same applies to a compound represented by another formula. The term "arbitrary" used in the explanation of chemical structural formulas means that "not only in cases when the position is arbitrary but also in cases when the number is arbitrary". For example, the expression "arbitrary A may be replaced by B, C or D," means that at least one A may be replaced by at least one B, at least one A may be replaced by at least one C, at least one A may be replaced by at least one D, and a plurality of A may be replaced by at least two of B, C and D. However, it is not desirable that a plurality of —$CH_2$— that are successive are replaced by the same groups in cases when arbitrary —$CH_2$— may be replaced by another group.

When the bonding position of a substituent on carbon in the ring is not clearly shown, the substituent may be bonded to any carbon without restraint as long as the bonding position is chemically reasonable. When the same symbols of a group are used in a plurality of formulas, each symbol means one of the groups within the range of the definition, which do not mean that these groups should be the same simultaneously. The symbols may be the same group in the plurality of formulas or the symbols may be different groups in every formula. Incidentally, the unit, gram (g), in Examples means a value of gram displayed in an electronic force valance. Values of percentage by weight or parts by weight are based on values thus measured.

One of the advantages of the invention is to provide a polymerizable liquid crystal compound that has a liquid crystal phase with a wide temperature range centering at room temperature, has an excellent compatibility with another polymerizable liquid crystal compound, has an excellent solubility in organic solvent and is polymerizable in air by heat or light. Another advantage is to provide a polymer that has optical anisotropy and has a plurality of excellent characteristics among characteristics such as transparency, mechanical strength, shrinkage, water permeability, water absorptivity, melting points, glass transition temperature, clearing points, chemical resistance and thermal resistance. A further advantage is to provide a liquid crystal display device containing the polymer having optical anisotropy.

The polymerizable liquid crystal compound of the invention had a polyether linkage, and satisfied a plurality of characteristics among characteristics such as a liquid crystal phase with a wide temperature range centering at room temperature, an excellent compatibility with another polymerizable liquid crystal compound, an excellent solubility in organic solvent, polymerization at room temperature, polymerization even in air, polymerization by heat, an easy polymerization, chemical stability and colorlessness. The solubility in a solvent that was highly safe was excellent when used especially for ink. A polymer formed from the polymerizable liquid crystal compound as a starting material satisfied a plurality of characteristics among characteristics such as optical anisotropy, a high peel adhesion to a supporting substrate, a sufficient hardness, transparent colorlessness, a high heat resistance, a high weather resistance, a low photoelasticity. Thus, the polymer of the invention can be utilized, for example, for elements of a liquid crystal display device, such as an optical retardation plate, a polarizer, an antireflection film, a selective reflection film, a brightness enhancement film and a viewing angle-compensation film.

The invention includes item 1 described above and items 2 to 31 described below.

[2] The polymerizable liquid crystal compound according to item 1, wherein $A^1$ and $A^2$ are each independently 1,4-cyclohexylene, 1,4-phenylene, naphthalene-2,6-diyl or fluorene-2,7-diyl; one or two hydrogens in the 1,4-phenylene and fluorene-2,7-diyl may be replaced by fluorine, methyl or trifluoromethyl.

[3] The polymerizable liquid crystal compound according to item 1, wherein $A^1$ and $A^2$ are each independently 1,4-cyclohexylene, 1,4-phenylene, naphthalene-2,6-diyl or fluorene-2,7-diyl; one or two hydrogens in the 1,4-phenylene and fluorene-2,7-diyl may be replaced by fluorine, methyl or trifluoromethyl; $Z^1$ and $Z^3$ are each independently a single bond, —O—, —COO— or —OCO—; $Z^2$ is independently a single bond, —COO—, —OCO—, —CH=CH—OCO—, —OCO—CH=CH—, —$CH_2CH_2$—COO—, —OCO—$CH_2CH_2$—, —$CH_2CH_2$— or —C≡C—; and m is an integer of 1 to 3.

[4] The polymerizable liquid crystal compound according to any one of items 1 to 3, wherein in formula (1) according to item 1, $Z^1$ and $Z^2$ are each independently a single bond, —O—, —COO— or —OCO—; $Z^2$ is independently a single bond, —COO— or —OCO—; and m is 1 or 2.

[5] The polymerizable liquid crystal compound according to any one of items 1 to 4, wherein in formula (1) according to item 1, $Q^1$ and $Q^2$ are each independently —O($CH_2CH_2O)_{n1}(CH_2CH_2CH_2O)_{n2}$— or —O($CH_2CH_2CH_2O)_{n2}(CH_2CH_2O)_{n1}$.

[6] The polymerizable liquid crystal compound according to any one of items 1 to 4, wherein in formula (1) according item 1, $Q^1$ and $Q^2$ are each independently —O($CH_2CH_2O)_{n1}$— or —O($CH_2CH_2CH_2O)_{n2}$—; and n1 and n2 are each independently an integer of 2 to 5.

[7] The polymerizable liquid crystal compound according to item 6, wherein n1 and n2 are each independently 2 or 3.

[8] The polymerizable liquid crystal compound according to any one of items 1 to 7, wherein in formula (2-1) to formula (2-3) according to item 1, R is independently hydrogen, methyl or ethyl.

[9] The polymerizable liquid crystal compound according to item 1, wherein $A^1$ and $A^2$ are each independently 1,4-cyclohexylene, 1,4-phenylene, naphthalene-2,6-diyl or fluorene-2,7-diyl, and arbitrary hydrogen in the 1,4-phenylene and fluorene-2,7-diyl may be replaced by fluorine, methyl or trifluoromethyl; $Z^1$ and $Z^3$ are a single bond; $Z^2$ is independently a single bond, —COO—, —OCO—, —CH=CH—COO—, —$CH_2CH_2$—COO—, —OCO—CH=CH—, —OCO—$CH_2CH_2$—, —$CH_2CH_2$— or —C≡C—; m is an integer of 1 to 3; $Q^1$ and $Q^2$ are each independently —O($CH_2CH_2O)_2$—, —O($CH_2CH_2O)_3$—, —O($CH_2CH_2CH_2O)_2$— or —O($CH_2CH_2O)_3$—; and $P^1$ and $P^2$ are each independently a polymerizable group represented by any one of formula (2-1) to formula (2-3) and R is independently hydrogen, methyl or ethyl.

[10] The polymerizable liquid crystal compound according to item 9, wherein $A^1$ and $A^2$ are each independently 1,4-cyclohexylene or 1,4-phenylene, and one or two hydrogens in the 1,4-phenylene may be replaced by fluorine or methyl; $Z^2$ is a single bond, —OCO—, or —OCO—; and m is 1 or 2.

[11] The polymerizable liquid crystal compound according to item 9, wherein $A^1$ and $A^2$ are each independently 1,4-cyclohexylene or 1,4-phenylene, and one or two hydrogens in the 1,4-phenylene may be replaced by fluorine or methyl; $Z^2$ is a single bond, —COO— or —OCO—; m is 1 or 2; and $P^1$ and $P^2$ is a polymerizable group represented by formula (2-1) and R is hydrogen.

[12] The polymerizable liquid crystal compound according to item 9, wherein $A^1$ and $A^2$ are each independently 1,4-cyclohexylene or 1,4-phenylene, and one or two hydrogens in the 1,4-phenylene may be replaced by fluorine or methyl; $Z^2$ is a single bond, —COO— or —OCO—; m is 1 or 2; and $P^1$ and $P^2$ are a polymerizable group represented by formula (2-2) and R is hydrogen.

[13] The polymerizable liquid crystal compound according to item 9, wherein $A^1$ and $A^2$ are each independently 1,4-cyclohexylene or 1,4-phenylene and one or two hydrogens in the 1,4-phenylene may be replaced by fluorine or methyl; $Z^2$ is a single bond, —COO— or —OCO—; m is 1 or 2; and $P^1$ and $P^2$ are a polymerizable group represented by formula (2-3) and R is methyl or ethyl.

[14] A composition including at least one of compounds according to any one of items 1 to 13.

[15] A polymerizable liquid crystal composition including at least one compound represented by formula (1) and at least one compound selected from the group of compounds represented by formula (M1), formula (M2), formula (M3) and formula (M4):

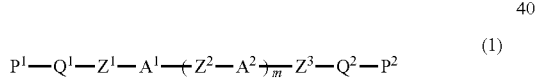
(1)

wherein $A^1$ and $A^2$ are each independently 1,4-cyclohexylene, 1,4-phenylene, pyridine-2,5-diyl, pyrimidine-2,5-diyl, naphthalene-2,6-diyl, tetrahydronaphthalene-2,6-diyl or fluorene-2,7-diyl; one or two nonadjacent —CH₂— in the 1,4-cyclohexylene may be replaced by —O—; arbitrary hydrogen in the 1,4-phenylene and fluorene-2,7-diyl may be replaced by fluorine, chlorine, cyano, methyl, ethyl, methoxy, hydroxy, formyl, acetoxy, acetyl, trifluoroacetyl, difluoromethyl or trifluoromethyl;

$Z^1$, $Z^2$ and $Z^3$ are each independently a single bond, —O—, —COO—, —OCO—, —CH=CH—COO—, —OCO—CH=CH—, —OCO—CH₂CH₂—, —CH₂CH₂—COO—, —C≡C—COO—, —OCO—C≡C—, —CH₂O—, —OCH₂—, —CF₂O—, —OCF₂—, —CONH—, —NHCO—, —(CH₂)₄—, —CH₂CH₂—, —CF₂CF₂—, —CH=CH—, —CF=CF— or —C≡C—;

m is an integer of 1 to 5; a plurality of $Z^2$ may be different rings or at least two of a plurality of $Z^2$ may be the same groups, and a plurality of $A^2$ may be different rings or at least two of a plurality of $A^2$ may be the same rings, when m is 2 or more;

$Q^1$ and $Q^2$ are each independently alkylene having 1 to 20 carbons, —O(CH₂CH₂O)$_{n1}$(CH₂CH₂CH₂O)$_{n2}$— or —O(CH₂CH₂CH₂O)$_{n2}$(CH₂CH₂O)$_{n1}$—; arbitrary hydrogen in the alkylene may be replaced by fluorine or chlorine; in the alkylene, one —CH₂— may be replaced by —O— and one or two nonadjacent —CH₂— may be replaced by —COO—, —OCO—, —CH=CH— or —C≡C—, when the number of carbon is two or more; n1 and n2 are each independently an integer of 0 to 5, and the sum of n1 and n2 is 2 to 5; at least one of $Q^1$ and $Q^2$ is —O(CH₂CH₂O)$_{n1}$(CH₂CH₂CH₂O)$_{n2}$— or —O(CH₂CH₂CH₂O)$_{n2}$(CH₂CH₂O)$_{n1}$—, and $Z^1$ is a single bond when $Q^1$ is —O(CH₂CH₂O)$_{n1}$(CH₂CH₂CH₂O)$_{n2}$— or —O(CH₂CH₂CH₂O)$_{n2}$(CH₂CH₂O)$_{n1}$— and $Z^3$ is a single bond when $Q^2$ is —O(CH₂CH₂O)$_{n1}$(CH₂CH₂CH₂O)$_{n2}$— or —O(CH₂CH₂CH₂O)$_{n2}$(CH₂CH₂O)$_{n1}$—; and $P^1$ and $P^2$ are each independently a polymerizable group represented by any one of formula (2-1) to formula (2-3):

(2-1)

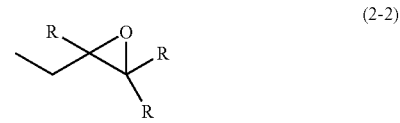
(2-2)

(2-3)

wherein R is independently hydrogen, halogen or alkyl having 1 to 5 carbons; and

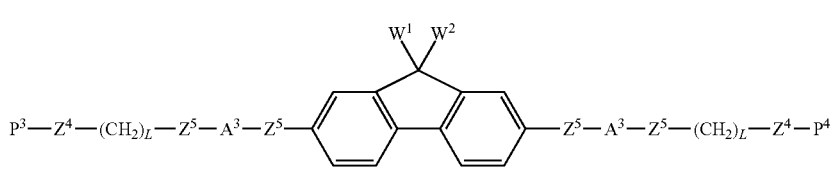
(M1)

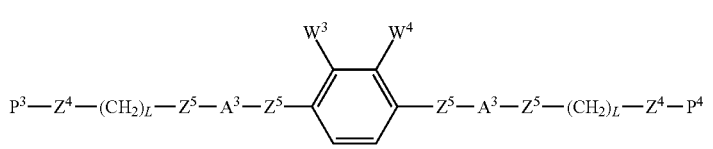
(M2)

(M3)

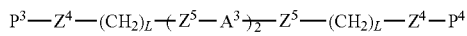

(M4)

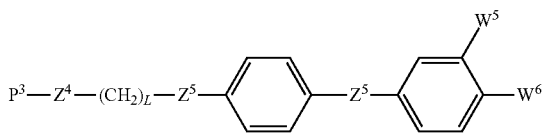

wherein $A^3$ is independently 1,4-cyclohexylene or 1,4-phenylene; in the 1,4-phenylene, arbitrary hydrogen may be replaced by fluorine or chlorine and one or two hydrogens may be replaced by cyano, methyl, ethyl, methoxy, hydroxy, formyl, acetoxy, acetyl, trifluoroacetyl, difluoromethyl or trifluoromethyl; $Z^4$ and $Z^5$ are each independently a single bond, —O—, —COO—, —OCO—, —CH═CH—COO—, —OCO—CH═CH—, —OCO—CH$_2$CH$_2$—, —CH$_2$CH$_2$—COO—, —C≡C—COO—, —OCO—C≡C—, —CH$_2$O—, —OCH$_2$—, —CF$_2$O—, —OCF$_2$—, —CONH—, —NHCO—, —(CH$_2$)$_4$—, —CH$_2$CH$_2$—, —CF$_2$CF$_2$—, —CH═CH—, —CF═CF— or —C≡C—; L is independently an integer of 2 to 20; $W^1$, $W^2$, $W^3$, $W^4$ and $W^5$ are each independently hydrogen, fluorine, chlorine, methyl or trifluoromethyl; $W^6$ is —CN, —OCF$_3$, alkyl having 1 to 10 carbons or alkoxy having 1 to 10 carbons; and $P^3$ and $P^4$ are each independently a polymerizable group represented by any one of formula (2-1) to formula (2-3) described above.

[16] The polymerizable liquid crystal composition according to item 15, wherein
in formula (1), $A^1$ and $A^2$ are each independently 1,4-cyclohexylene, 1,4-phenylene naphthalene-2,6-diyl or fluorene-2,7-diyl, and arbitrary hydrogen in the 1,4-phenylene and fluorene-2,7-diyl may be replaced by fluorine, methyl or trifluoromethyl; $Z^1$ and $Z^3$ are a single bond; $Z^2$ is independently a single bond, —COO—, —OCO—, —CH═CH—COO—, —CH$_2$CH$_2$—OCO—, —OCO—CH═CH—, —OCO—CH$_2$CH$_2$—, —CH$_2$CH$_2$— or —C≡C—; m is an integer of 1 to 3; $Q^1$ and $Q^2$ are each independently —O(CH$_2$CH$_2$O)$_2$—, —O(CH$_2$CH$_2$O)$_3$—, —O(CH$_2$CH$_2$CH$_2$O)$_2$— or —O(CH$_2$CH$_2$O)$_3$—; $P^1$ and $P^2$ are each independently a polymerizable group represented by any one of formula (2-1) to formula (2-3) and R is independently hydrogen, methyl or ethyl;
in formula (M1), formula (M2), formula (M3) and formula (M4), $A^3$ is independently 1,4-cyclohexylene or 1,4-phenylene and one or two hydrogens in the 1,4-phenylene may be replaced by fluorine or methyl; $Z^4$ and $Z^5$ are each independently —O—, —COO—, —OCO— or —OCOO—; L is independently an integer of 2 to 8; $W^1$ and $W^2$ are each independently hydrogen or methyl; $W^3$ and $W^4$ are each independently hydrogen, fluorine, methyl or trifluoromethyl; and $W^5$ is hydrogen, fluorine or trifluoromethyl.

[17] The polymerizable liquid crystal composition according to item 16, wherein
in formula (1), $A^1$ and $A^2$ are each independently 1,4-cyclohexylene or 1,4-phenylene and one or two hydrogens in the 1,4-phenylene may be replaced by fluorine or methyl; $Z^2$ is independently a single bond, —COO— or —OCO—; m is 1 or 2;
in formula (M1), formula (M2), formula (M3) and formula (M4), $A^3$ is independently 1,4-cyclohexylene or 1,4-phenylene and one or two hydrogens in the 1,4-phenylene may be replaced by fluorine or methyl; $Z^4$ and $Z^5$ are each independently —O—, —COO—, —OCO— or —OCOO—; $W^1$ and $W^2$ are each independently hydrogen or methyl; $W^3$ and $W^4$ are each independently hydrogen, fluorine, methyl or trifluoromethyl; and $W^5$ is hydrogen, fluorine or trifluoromethyl.

[18] The polymerizable liquid crystal composition according to anyone of items 15 to 17, wherein the ratio of at least one compound represented by formula (1) according to item 15 is in the range of approximately 5% to approximately 95% by weight and the ratio of at least one compound selected from the group of compounds represented by formula (M1), formula (M2), formula (M3) and formula (M4) is in the range of approximately 5% to approximately 95% by weight, based on the total amount of at least one compound represented by formula (1) and at least one compound selected from the group of compounds represented by formula (M1), formula (M2), formula (M3) and formula (M4).

[19] The polymerizable liquid crystal composition according to any one of items 15 to 17, wherein the ratio of at least one compound represented by formula (1) according to item 15 is in the range of approximately 10% to approximately 90% by weight and the ratio of at least one compound selected from the group of compounds represented by formula (M1), formula (M2), formula (M3) and formula (M4) is in the range of approximately 10% to approximately 90% by weight, based on the total amount of at least one compound represented by formula (1) and at least one compound selected from the group of the compounds represented by formula (M1), formula (M2), formula (M3) and formula (M4).

[20] The polymerizable liquid crystal composition according to any one of items 15 to 17, wherein the ratio of at least one compound represented by formula (1) according item 15 is in the range of approximately 20% to approximately 70% by weight and the ratio of at least one compound selected from the group of compounds represented by formula (M1), formula (M2), formula (M3) and formula (M4) is in the range of approximately 30% to approximately 80% by weight, based on the total amount of at least one compound represented by formula (1) and at least one compound selected from the group of compounds represented by formula (M1), formula (M2), formula (M3) and formula (M4).

[21] The polymerizable liquid crystal composition according to any one of items 15 to 20, wherein the composition further includes another polymerizable compound.

[22] The polymerizable liquid crystal composition according to any one of items 15 to 21, wherein the composition further includes another polymerizable and optically active compound.

[23] The polymerizable liquid crystal composition according to any one of items 15 to 22, wherein the composition further includes a non-polymerizable liquid crystal compound.

[24] The polymerizable liquid crystal composition according to any one of items 15 to 23, wherein the composition further includes a non-polymerizable and optically active compound.

[25] An optically anisotropic film formed by polymerization of at least one of compounds according to any one of items 1 to 13.

[26] An optically anisotropic film formed by polymerization of the polymerizable liquid crystal composition according to any one of items 15 to 24.

[27] The optically anisotropic film according to item 25 or 26, wherein the film has optical properties of an A-plate.

[28] The optically anisotropic film according to item 25 or 26, wherein the film has optical properties of a C-plate.

[29] The optically anisotropic film according to item 25 or 26, wherein the film has optical properties of a negative C-plate.

[30] The optically anisotropic film according to item 25 or 26, wherein the film has optical properties of an O-plate.

[31] A liquid crystal display device that contains the optically anisotropic film according to any one of items 25 to 30.

The compound (1) of the invention is characterized by a high physical and chemical stability under the conditions usually used and a high solubility in a polar solvent. A high optical anisotropy, a low optical anisotropy, a low viscosity and so forth can be adjusted by a suitable selection of the ring, the bonding group and the side chain constituting the compound of the invention. Even when atoms constituting the compound of the invention are isotopes, the compound can be used desirably because its characteristics are equivalent to those of the original compound.

The compound (1) is easily cured in air because a polymerizing mode belongs to cationic polymerization. A polymer formed from the bifunctional compound has a more rigid cross-link structure in comparison with that formed from the monofunctional compound, and thus it has a higher heat resistance, a lower water-absorptivity, a lower water-permeability, a lower gas-permeability and a higher mechanical strength (especially in hardness). Furthermore, the polymerizable compound is characterized by a high solubility in a safety solvent because of a polyether linkage in the side chain.

A polymerizable liquid crystal compound of the invention is represented by formula (1).

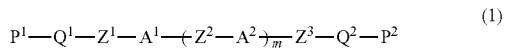

$$P^1-Q^1-Z^1-A^1-(Z^2-A^2)_m-Z^3-Q^2-P^2 \quad (1)$$

$A^1$ and $A^2$ are each independently 1,4-cyclohexylene, 1,4-phenylene, pyridine-2,5-diyl, pyrimidine-2,5-diyl, naphthalene-2,6-diyl, tetrahydronaphthalene-2,6-diyl or fluorene-2,7-diyl. One or two nonadjacent —$CH_2$— in the 1,4-cyclohexylene may be replaced by —O— and arbitrary hydrogen in the 1,4-phenylene and fluorene-2,7-diyl may be replaced by fluorine, chlorine, cyano, methyl, ethyl, methoxy, hydroxy, formyl, acetoxy, acetyl, trifluoroacetyl, difluoromethyl or trifluoromethyl.

Desirable $A^1$ and $A^2$ are each independently 1,4-cyclohexylene, 1,4-phenylene, naphthalene-2,6-diyl or fluorene-2,7-diyl, where one or two hydrogens in the 1,4-phenylene and fluorene-2,7-diyl may be replaced by fluorine or methyl.

More desirable $A^1$ and $A^2$ are each independently 1,4-cyclohexylene or 1,4-phenylene, where one or two hydrogens in the 1,4-phenylene may be replaced by fluorine or methyl.

That is to say, a desirable example of $A^1$ and $A^2$ is 1,4-cyclohexylene, 1,4-phenylene, 2-fluoro-1,4'-phenylene 3-fluoro-1,4-phenylene, 2-chloro-1,4-phenylene, 3-chloro-1,4-phenylene, 2,3-difluoro-1,4-phenylene, 2,5-difluoro-1,4-phenylene, 2,6-difluoro-1,4-phenylene, 2-methyl-1,4-phenylene, 3-methyl-1,4-phenylene and 2,3-dimethyl-1,4-phenylene. The compound shows a tendency to increase the melting point, the clearing point and the temperature range of a liquid crystal phase when both of $A^1$ and $A^2$ are 1,4-phenylene, and the compound shows a tendency to decrease the temperature range of a liquid crystal phase and the optical anisotropy when at least one of $A^1$ and $A^2$ is 1,4-cyclohexylene.

The viscosity is small when the bonding group $Z^2$ is a single bond, —$(CH_2)_2$—, —$CH_2O$—, —$OCH_2$—, —$CF_2O$—, —$OCF_2$—, —CH=CH—, —CF=$CF_2$, or —$(CH_2)_4$—. The viscosity is smaller when the bonding group $Z^2$ is a single bond, —$(CH_2)_2$—, —$OCF_2$—, —$CF_2O$—, —CH=CH— or —$(CH_2)_4$—. The temperature range of a liquid crystal phase is wide and the ratio of the elastic constants is large when the bonding group $Z^2$ is —CH=CH— or —CF=CF—. The optical anisotropy is large when the bonding group $Z^2$ is —C≡C—.

The compound shows a tendency to increase the temperature range of a liquid crystal phase and the solubility in an organic solvent when the bonding group $Z^1$ and $Z^3$ is —O—. The compound shows a tendency to increase the melting point and also the clearing point when the bonding group $Z^1$ and $Z^3$ are —COO— or —OCO—.

m is an integer of 1 to 5, and desirable m is an integer of 1 to 3 and more desirable m is 1 or 2. A plurality of $Z^2$ may be different groups or at least two of a plurality of $Z^2$ may be the same groups, when m is 2 or more. Similarly, a plurality of $A^2$ may be different rings or at least two of a plurality of $A^2$ may be the same rings, when m is 2 or more.

$Q^1$ and $Q^2$ that are spacers are independently alkylene having 1 to 20 carbons, —$O(CH_2CH_2O)_{n1}(CH_2CH_2CH_2O)_{n2}$— or —$O(CH_2CH_2CH_2O)_{n2}(CH_2CH_2O)_n$—. At least one of $Q^1$ and $Q^2$ is —$O(CH_2CH_2O)_{n1}(CH_2CH_2CH_2O)_{n2}$— or —$O(CH_2CH_2CH_2O)_{n2}(CH_2CH_2O)_{n1}$—, and desirable $Q^1$ and $Q^2$ are each independently —$O(CH_2CH_2O)_{n1}(CH_2CH_2CH_2O)_{n2}$— or —$O(CH_2CH_2CH_2O)_{n2}(CH_2CH_2O)_{n1}$—. n1 and n2 are each independently an integer of 0 to 5 and the sum of n1 and n2 is 2 to 5. In the alkylene having 1 to 20 carbons, arbitrary hydrogen may be replaced by fluorine or chlorine, and then one —$CH_2$— may be replaced by —O— and one or two nonadjacent —$CH_2$— may be replaced by —COO—, —OCO—, —CH=CH— or —C≡C— when the number of carbon is two or more. A desirable example of the alkylene includes hydrogen and alkylene having 2 to 10 carbons in which —$CH_2$— is not replaced by another group. The compound (1) shows a tendency to increase the temperature range of a liquid crystal phase, when $Q^1$ or $Q^2$ is such a desirable alkylene. The compound (1) shows a tendency to increase solubility in organic polar solvent, especially in a safety solvent, when $Q^1$ and $Q^2$ are each independently —$O(CH_2CH_2O)_{n1}CH_2CH_2CH_2O)_{n2}$— or —$O(CH_2CH_2CH_2O)_{n2}(CH_2CH_2O)_n$—. More desirable $Q^1$ and $Q^2$ are each independently —$O(CH_2CH_2O)_{n1}$— or —$O(CH_2CH_2CH_2O)_{n2}$—. At this point, n1 and n2 are each independently an integer of 2 to 5, and desirable n1 and n2 are each independently 2 or 3.

$P^1$ and $P^2$ are each independently a polymerizable group represented by any one of formula (2-1) to formula (2-3). Desirable $P^1$ and $P^2$ are the same groups that are represented by any one of formula (2-1) to formula (2-3). A polymer of the compound (1) is excellent in curability when $P^1$ and $P^2$ are a group represented by formula (2-2). The compound (1) shows a tendency to decrease the melting point and the clearing point, when $P^1$ and $P^2$ are a group represented by formula (2-3):

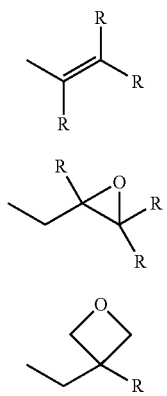

(2-1)

(2-2)

(2-3)

wherein R is independently hydrogen, halogen or alkyl having 1 to 5 carbons.

As described above, the compound (1) having objective physical properties can be obtained by the suitable selection of the kinds of polymerizable groups, spacers, rings and bonding groups, and the number of the rings. The compound (1) can be synthesized by means of a combination of techniques in synthetic organic chemistry. Methods for an introduction of objective terminal groups, rings and bonding groups to starting materials are described in books such as Houben-Wyle, Methods of Organic Chemistry, Georg Thieme Verlag, Stuttgart; Organic syntheses, John Wily & Sons, Inc.; Organic Reactions, John Wily & Sons Inc.; Comprehensive Organic Synthesis, Pergamon Press; and New Experimental Chemistry Course (Shin Jikken Kagaku Kouza, in Japanese title), Maruzen Co., LTD. In the following scheme, the meanings of symbols that are not explained are the same with that described before.

Formation of the bonding group $Z^2$ is explained in Schemes 1 to 11. In these schemes, $MSG^1$ and $MSG^2$ are an organic monovalent group having at least one ring. A plurality of $MSG^1$ (or $MSG^2$) may be the same or different. The compounds (1A) to (1M) correspond to the compound (1) of the invention.

<Synthesis of the Compound where the Bonding Group $Z^2$ is a Single Bond>

As Scheme 1 shows, the compound (1A) can be synthesized by the reaction of the arylboronic acid (S1) with the compound (S2), which is synthesized by a known method, in an aqueous solution of carbonate in the presence of catalyst such as tetrakis(triphenylphosphine)palladium. The compound (1A) can also be synthesized by the reaction of the compound (S3) that is synthesized by a known method, with n-butyllithium, and then with zinc chloride and by the reaction of the product with the compound (S2) in the presence of a catalyst such as dichlorobis (triphenylphosphine) palladium.

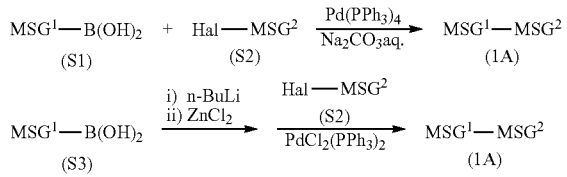

<Synthesis of the Compound where the Bonding Group $Z^2$ is —CH=CH—>

As Scheme 2 shows, the compound (1B) can be synthesized by the reaction of the aldehyde (S4) with a phosphine ylide generated by the addition of abase such as potassium t-butoxide to the phosphonium salt (S5) that is synthesized by a known method. Since a cis-isomer may be formed depending on the reaction conditions and the substrate, the cis-isomer is isomerized to the corresponding trans-isomer by a known method as requested.

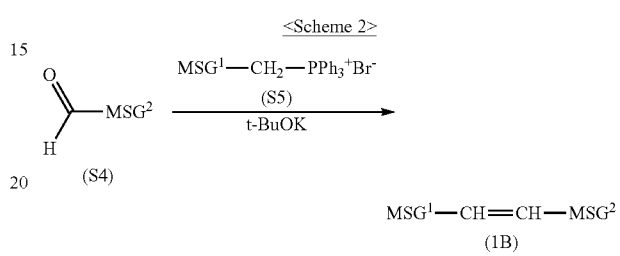

<Synthesis of the Compound where the Bonding Group $Z^2$ is —$(CH_2)_2$—>

As Scheme 3 shows, the compound (1C) can be synthesized by hydrogenation of the compound (1B) in the presence of a catalyst such as palladium on carbon.

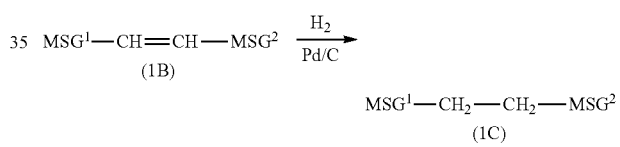

<Synthesis of the Compound where the Bonding Group $Z^2$ is —$(CF_2)_2$—>

As Scheme 4 shows, the compound (1D) having —$(CF_2)_2$— can be synthesized by fluorination of the diketone (S6) with sulfur tetrafluoride in the presence of a hydrogen fluoride catalyst, according to the method described in J. Am. Chem. Soc., 2001, 123, 5414.

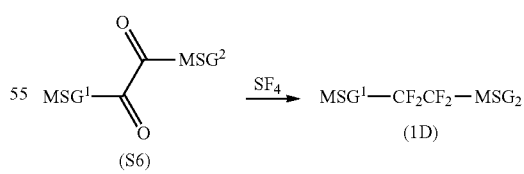

<Synthesis of the Compound where the Bonding Group $Z^2$ is —$(CH_2)_4$>

As Scheme 5 shows, the compound (1E) can be synthesized by catalytic hydrogenation of the compound having —$(CH_2)_2$—CH=CH—, which is synthesized using the phosphonium salt (S7) instead of the phosphonium salt (S5) according to the method in Scheme 2.

<Scheme 5>

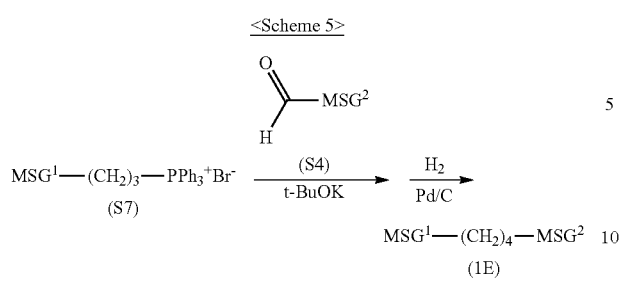

<Synthesis of the Compound where the Bonding group $Z^2$ is —$CH_2O$— or —$OCH_2$—>

As Scheme 6 shows, the compound (S4) is reduced with a reducing agent such as sodium borohydride, giving the compound (S8). Then, the compound (S8) is halogenated with hydrobromic acid or the like, giving the compound (S9). The compound (1F) can be synthesized by the reaction of the compound (S9) with the compound (S10) in the presence of potassium carbonate or the like. The compound having —$CH_2O$— can also be synthesized by this method.

<Scheme 6>

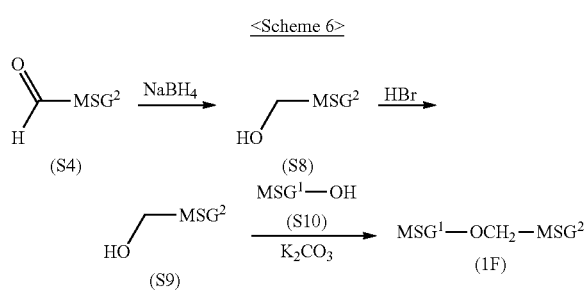

<Synthesis of the Compound where the Bonding Group $Z^2$ is —COO— or —OCO—>

As Scheme 7 shows, the compound (S3) is reacted with n-butyllithium and then with carbon dioxide, giving the carboxylic acid (S11). The compound (1G) having —COO— can be synthesized by the dehydration of the compound (S11) and phenol (S10) in the presence of DCC (1,3-dicyclohexylcarbodiimide) and DMAP (4-dimethylaminopyridine). The compound having —OCO—, can also be synthesized by this method. The compound (1G) can also be synthesized by the action of thionyl chloride or oxalyl chloride on the compound (S11), giving the corresponding acid chloride, and then by the action of the aldehyde (S10) on the acid chloride in the presence of a base such as pyridine or triethylamine.

<Scheme 7>

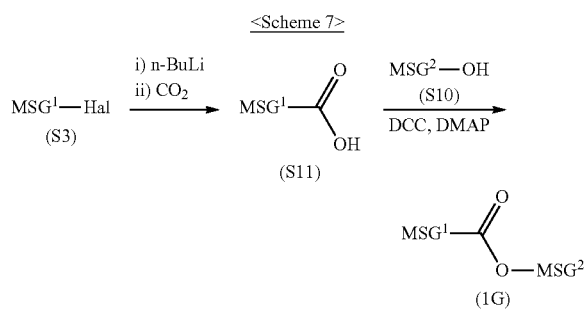

<Synthesis of the Compound where the Bonding Group $Z^2$ is —CF=CF—>

As Scheme 8 shows, the compound (S3) is treated with n-butyllithium, and then reacted with tetrafluoroethylene, giving the compound (S12). The compound (1H) can be synthesized by the treatment of the compound (S2) with n-butyllithium, and then by the reaction with the compound (S12). A cis-isomer of the compound (1H) can also be produced by selecting reaction conditions.

<Scheme 8>

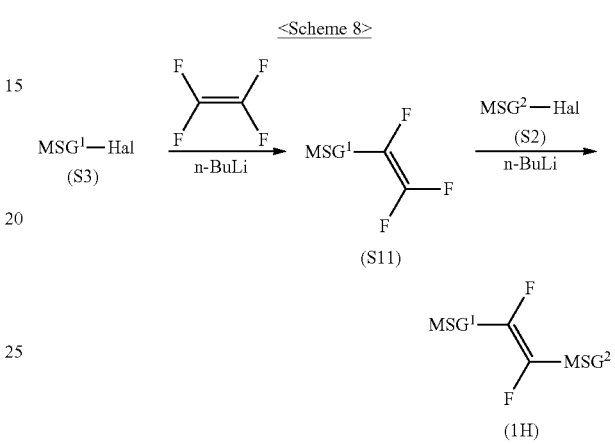

<Synthesis of the Compound where the Bonding Group $Z^2$ is —C≡C—>

As is shown below, the compound (1I) can be synthesized by the reaction of the compound (S12) with the compound (S2) in the presence of a catalyst of dichloropalladium and a copper halide.

<Scheme 9>

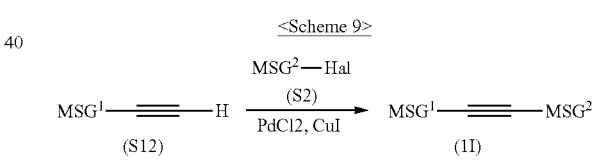

<Synthesis of the Compound where the Bonding Group $Z^2$ is —C≡C—OCO—>

As Scheme 10 shows, the compound (S12) is lithiated with n-butyllithium, and then reacted with carbon dioxide, giving the carboxylic acid (S13). The compound (1J) having —C≡C—OCO—, can be synthesized by the dehydration of the carboxylic acid (S13) and the phenol (S10) in the presence of DCC and DMAP. The compound having —OCO—C≡C— can also be synthesized by this method. The compound (1J) can also be synthesized via an acid chloride in the same way as in the derivation of the compound (1G) from the compound (S11) in Scheme 7.

<Scheme 10>

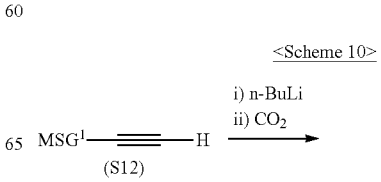

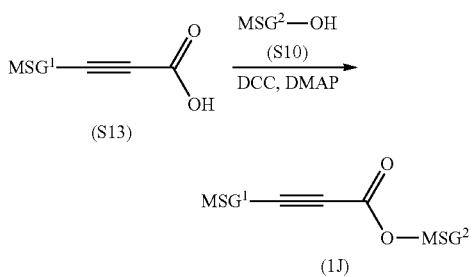

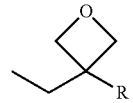

<Synthesis of the Compound where Z is —CF$_2$O— or —OCF$_2$—>

As Scheme 11 shows, the compound (1G) is treated with a thionating agent such as Lawesson's reagent, giving the compound (S14). The compound (1K) having —CF$_2$O— can be synthesized by fluorination of the compound (S14) with a hydrogen fluoride-pyridine complex and NBS (N-bromosuccinimide). The compound (1K) can also be synthesized by fluorination of the compound (S14) with (diethylamino)sulfurtrifluoride (DAST). The compound having —OCF$_2$— can also be synthesized by this method. These bonding groups can also be formed by the method described in P. Kirsch et al., Angew. Chem. Int. Ed. 2001, 40, 1480.

Scheme 11

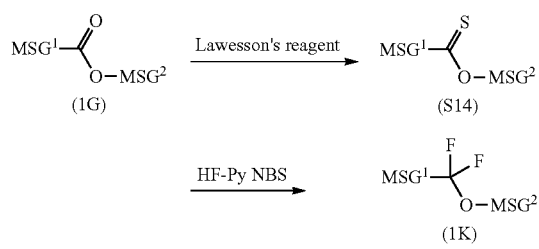

Methods for introducing a polymerizable group will be explained in Schemes 12 and 13. In these Schemes, MSG is an organic monovalent group having at least one ring. A plurality of MSG may be the same or different. Y is alkylene having 1 to 21 carbons, and in the alkylene, arbitrary hydrogen may be replaced by fluorine or chlorine and arbitrary —CH$_2$— may be replaced by —O—, —OCO—, —OCO—, —CH═CH— or —C≡C—. P is a polymerizable group represented by any one of formula (2-1) to formula (2-3):

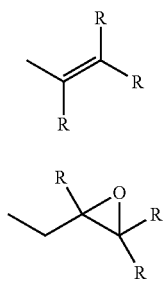

wherein R is independently hydrogen, halogen or alkyl having 1 to 5 carbons.

The compound (1L) corresponds to the compound (1) of the invention. These methods can be applied to the synthesis of the optically active compound (1) and the optically inactive compound (1).

<Earlier Introduction of a Polymerizable Group>

As Scheme 12 shows, the reaction of the diol (T1) with the compound (T2) that is synthesized by a known method, in the presence of a base such as sodium hydride, gives the monoether (T3). This compound is tosylated with p-toluenesulfonyl chloride or the like, giving the tosylate (T4). The compound (1L) can be synthesized by the reaction of the tosylate (T4) with the phenol (S10) in the presence of a base such as potassium carbonate. The compound (1L) can also be synthesized by the reaction of the compound (T5) that is synthesized by a known method, with the alcohol (T6) having a polymerizable group in the presence of a base such as sodium hydroxide, giving the monoether (T7), and then by the reaction of the monoether (T7) with the phenol (S10) in the presence of a base such as potassium carbonate.

<Scheme 12>

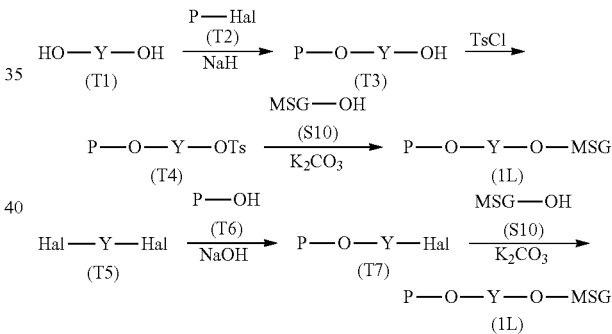

<Later Introduction of a Polymerizable Group>

As Scheme 13 shows, the reaction of the phenol (S10) with the compound (T8) that is synthesized by a known method, in the presence of a base such as potassium carbonate, gives the monoether (T9). The compound (1L) can be synthesized by the reaction of the monoether (T9) with the compound (T2) in the presence of a base such as sodium hydroxide.

<Scheme 13>

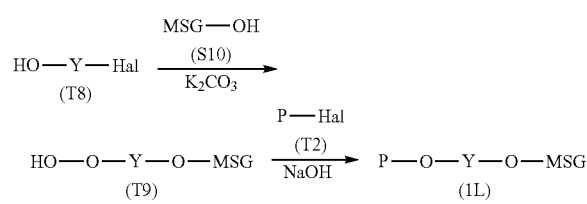

The compound of the invention can be produced by way of a combination of the methods described above. However, production methods are not limited to the methods described above. An example of the compound (1) synthesized by the method described above is as follows. Incidentally, the structures of compounds synthesized in the manner described above can be characterized by means of proton NMR spectroscopy.
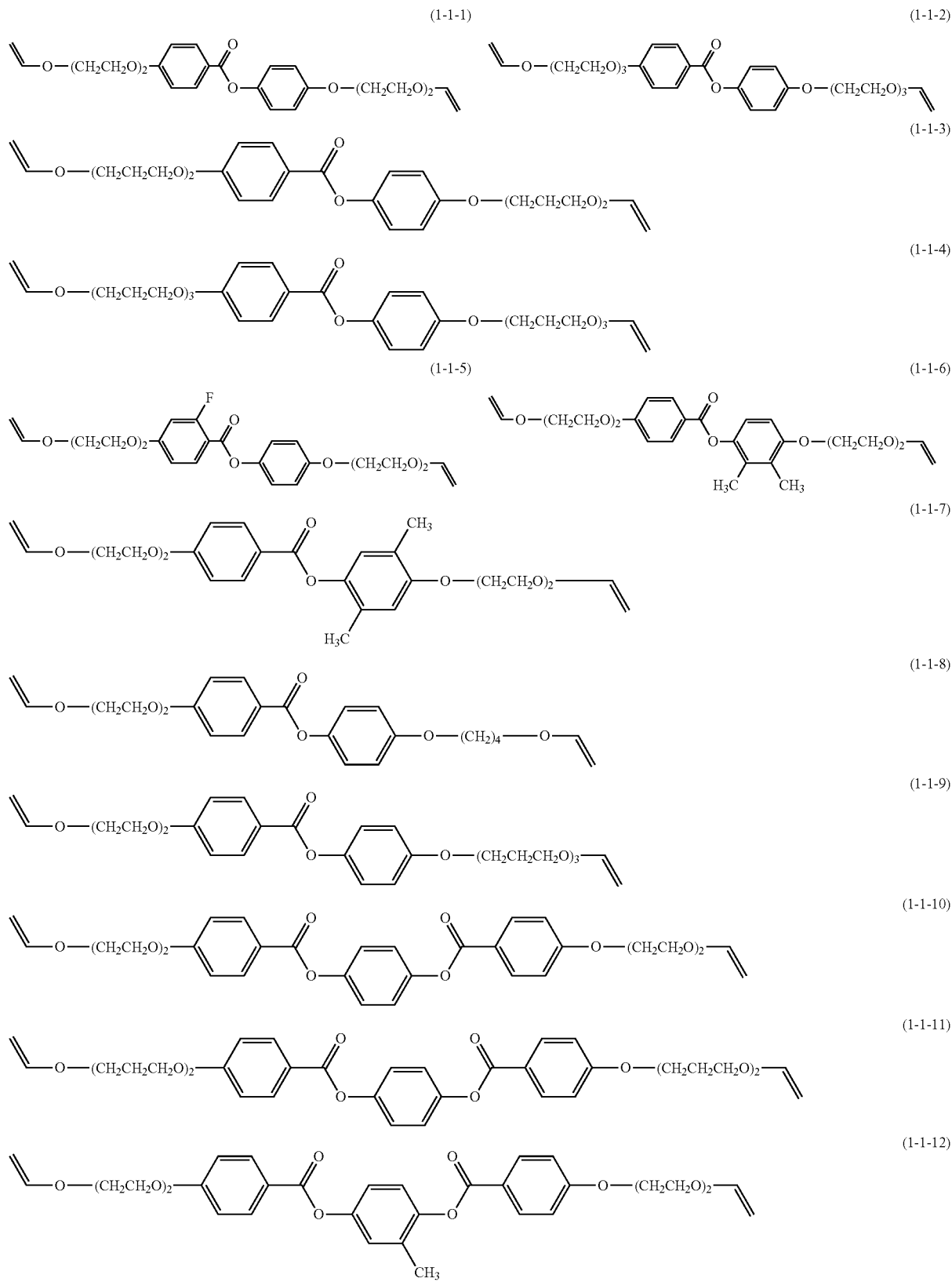

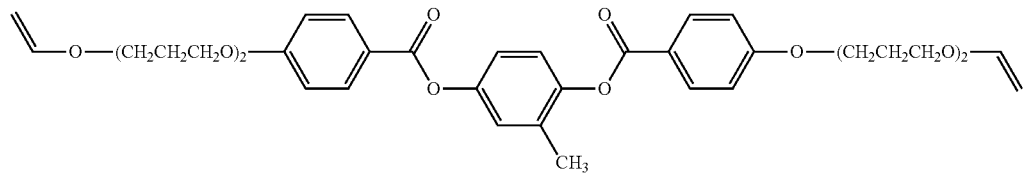
(1-1-13)
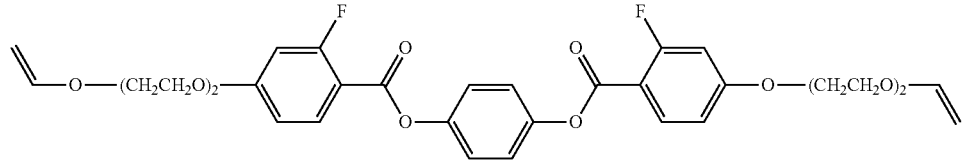
(1-1-14)
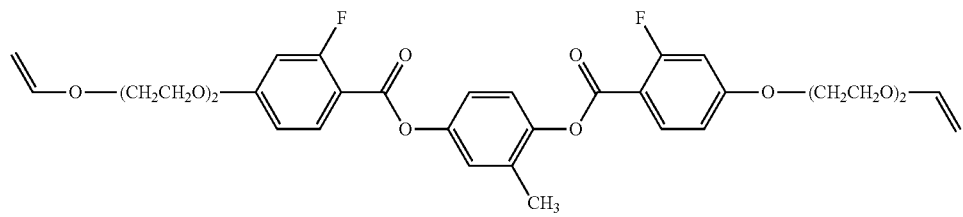
(1-1-15)
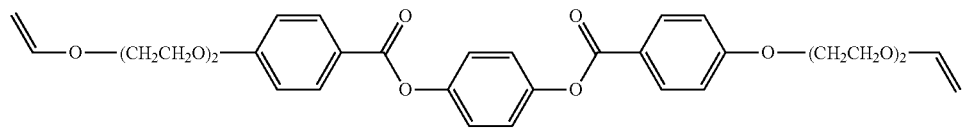
(1-1-16)
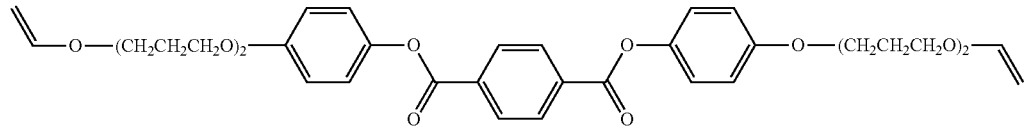
(1-1-17)
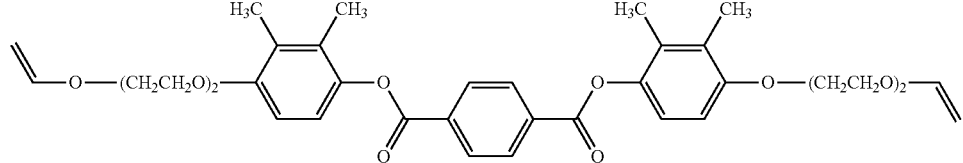
(1-1-18)
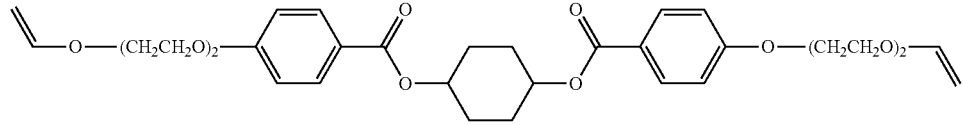
(1-1-19)
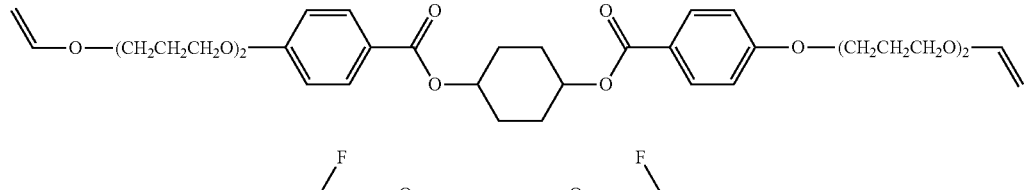
(1-1-20)
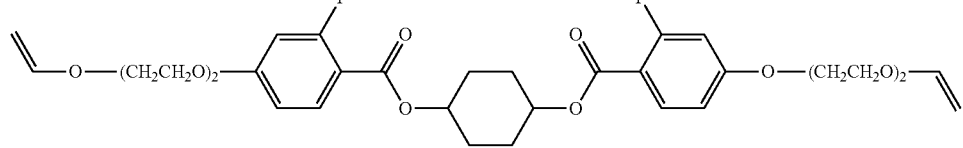
(1-1-21)
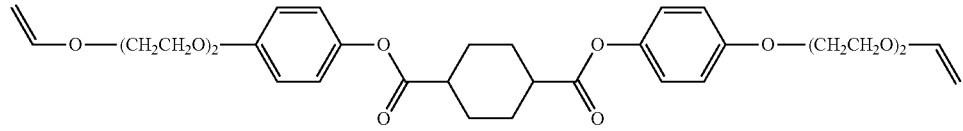
(1-1-22)

-continued
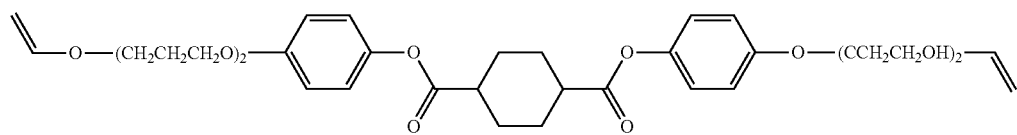
(1-1-23)
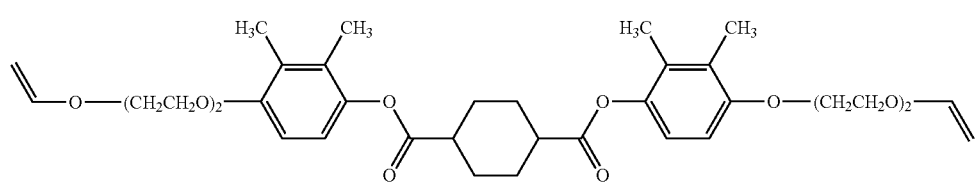
(1-1-24)
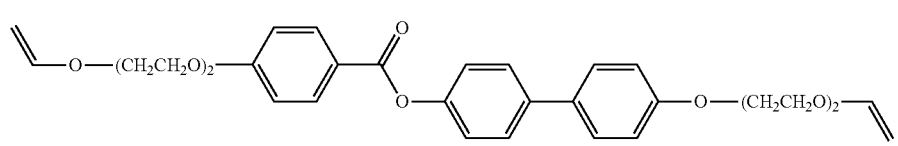
(1-1-25)
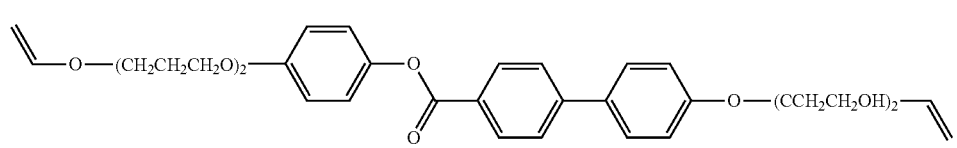
(1-1-26)
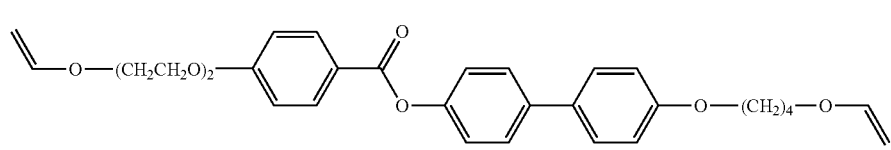
(1-1-27)
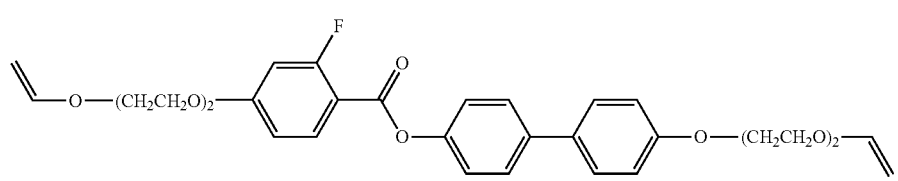
(1-1-28)
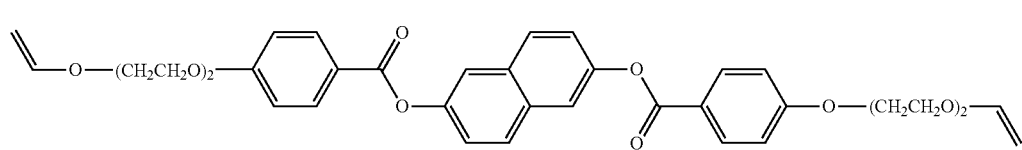
(1-1-29)
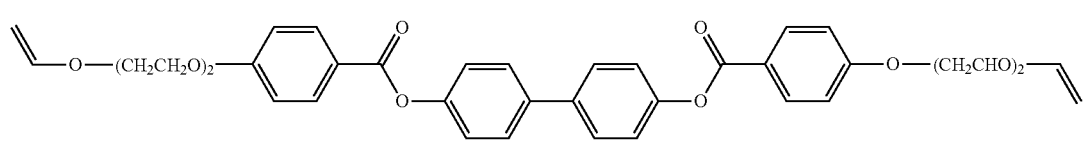
(1-1-30)
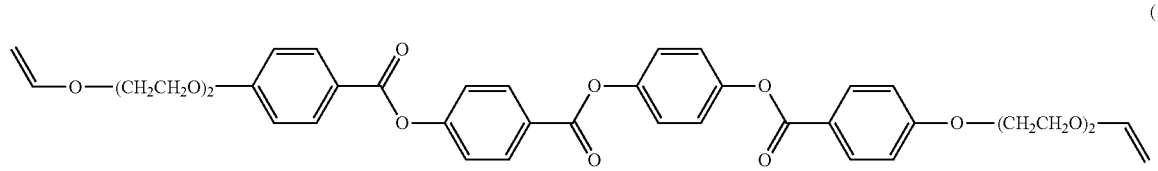
(1-1-31)
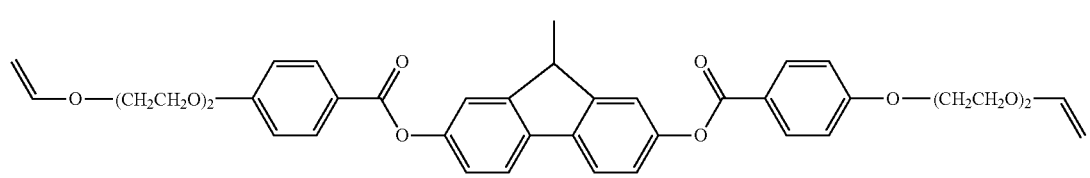
(1-1-32)

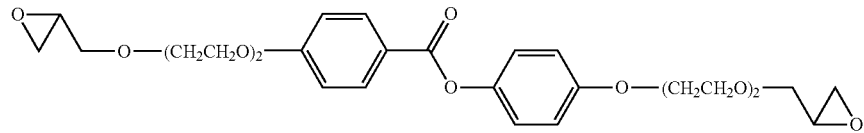
(1-2-1)
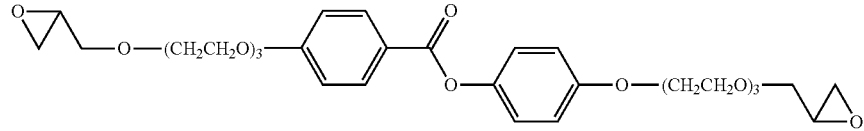
(1-2-2)
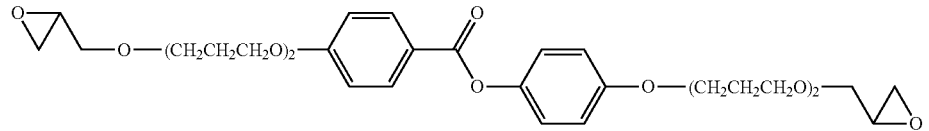
(1-2-3)
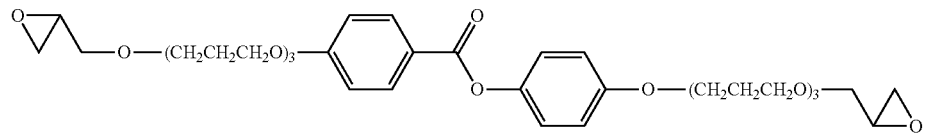
(1-2-4)
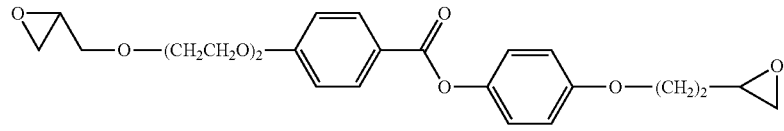
(1-2-5)
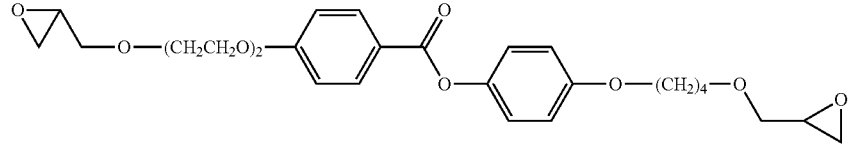
(1-2-6)
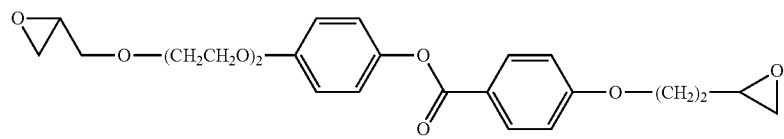
(1-2-7)
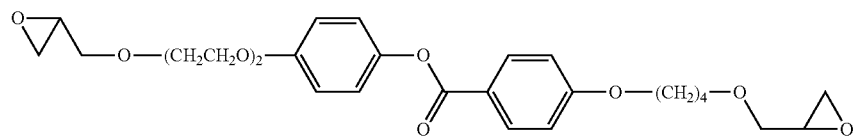
(1-2-8)
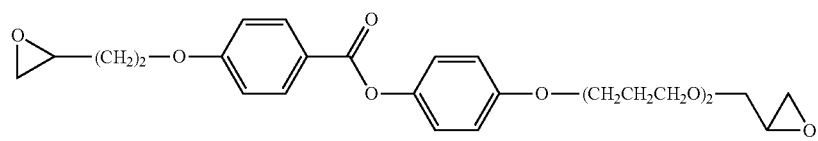
(1-2-9)
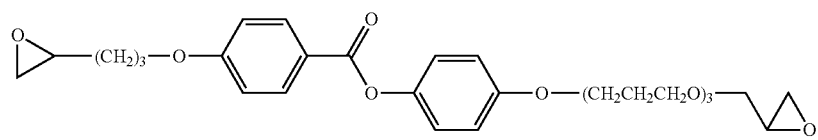
(1-3-10)
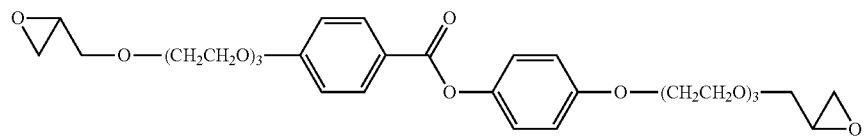
(1-2-11)

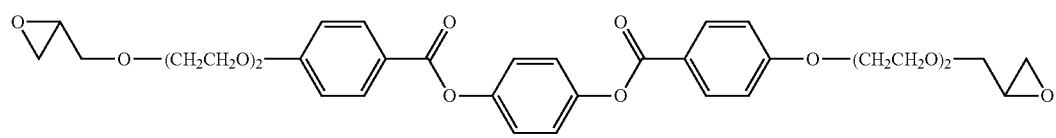
(1-2-12)
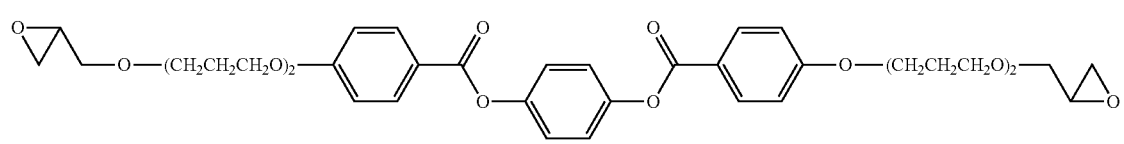
(1-2-13)
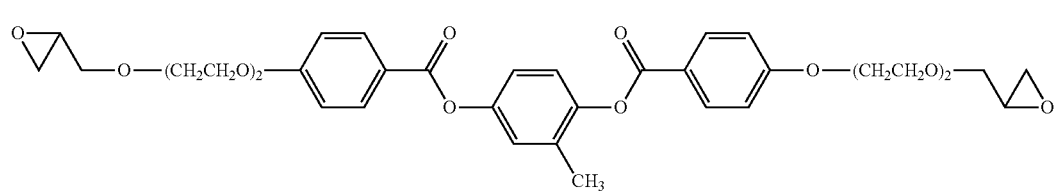
(1-2-14)
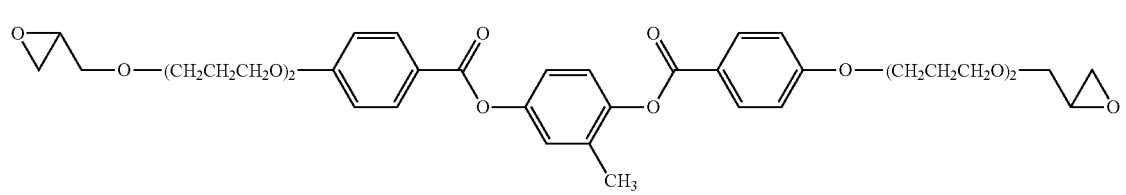
(1-2-15)
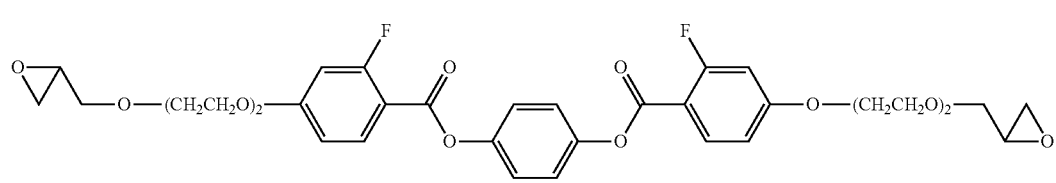
(1-2-16)
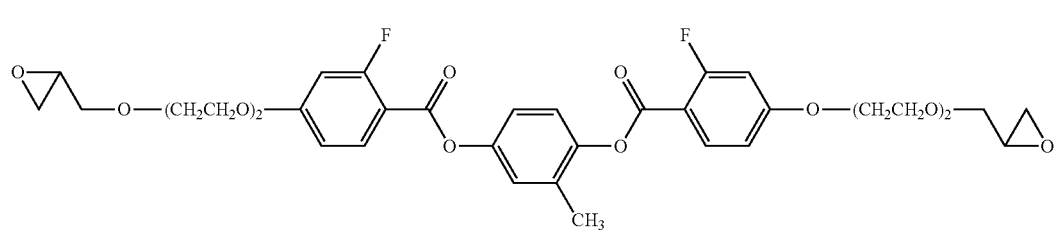
(1-2-17)
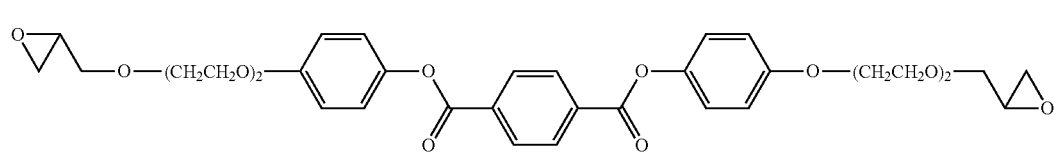
(1-2-18)
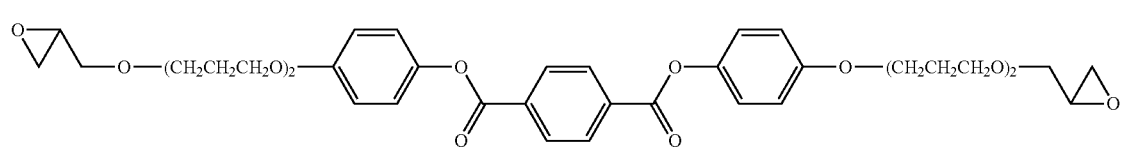
(1-2-19)
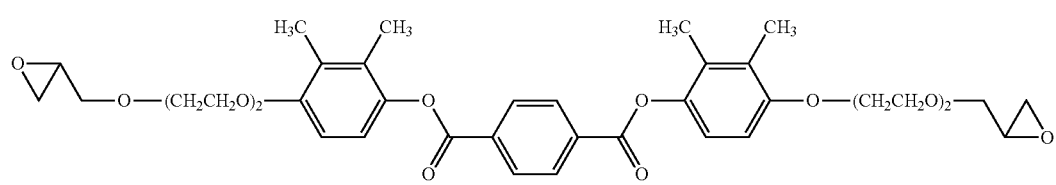
(1-2-20)

-continued
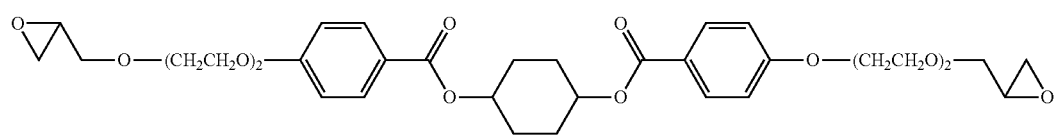
(1-2-21)
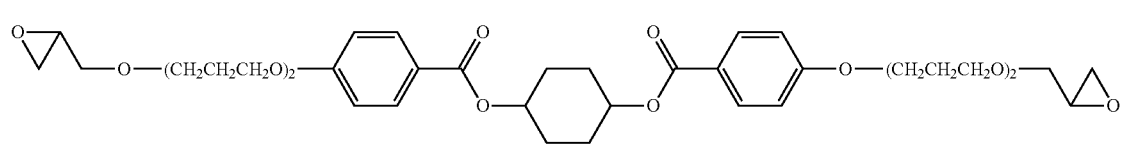
(1-2-22)
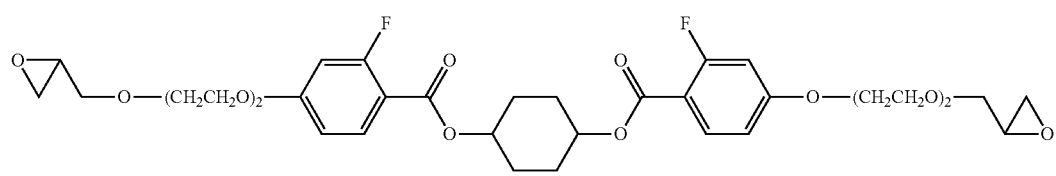
(1-2-23)
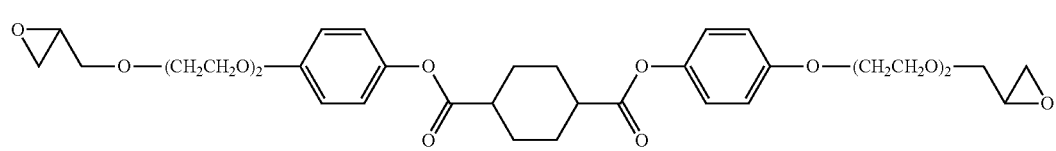
(1-2-24)
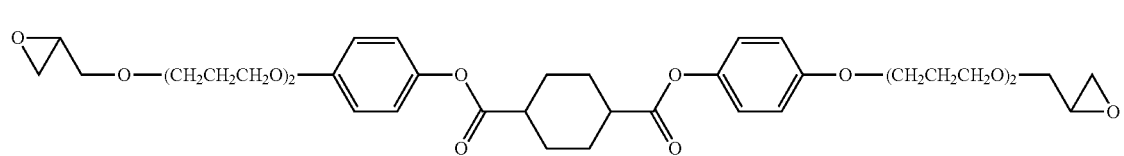
(1-2-25)
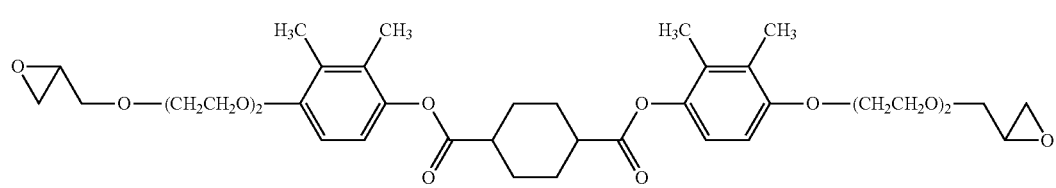
(1-2-26)
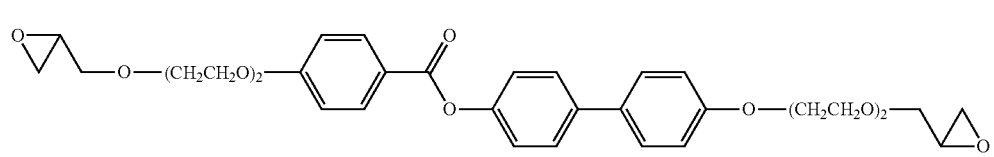
(1-2-27)
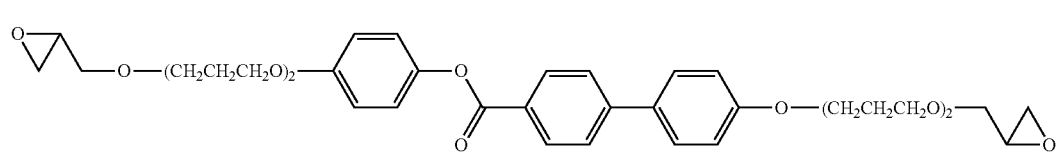
(1-2-28)
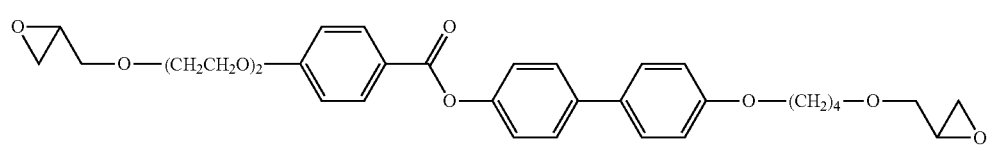
(1-2-29)
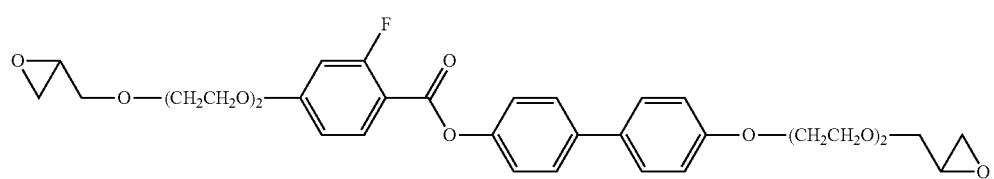
(1-2-30)

-continued
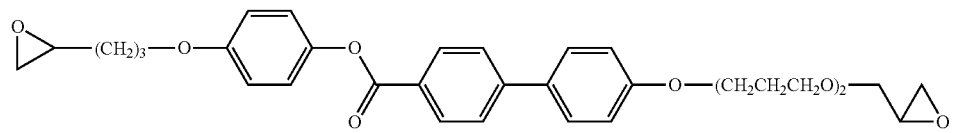
(1-2-31)
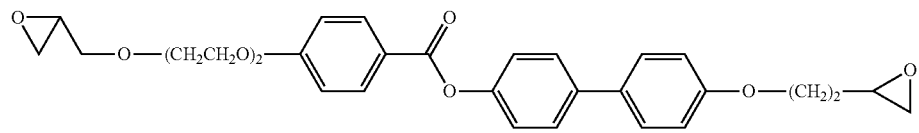
(1-2-32)
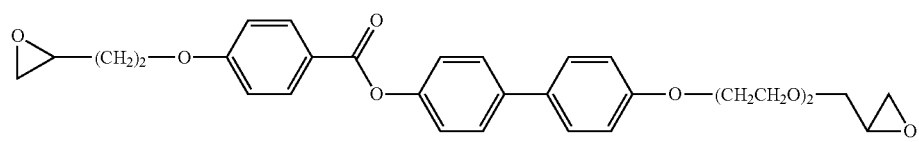
(1-2-33)
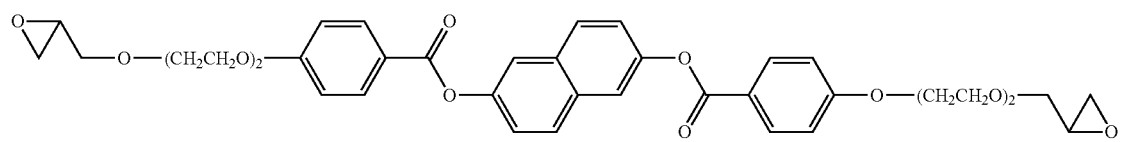
(1-2-34)
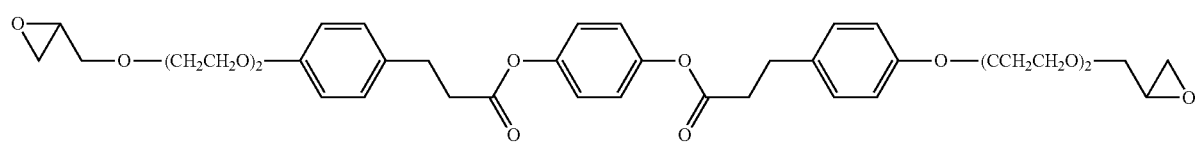
(1-2-35)
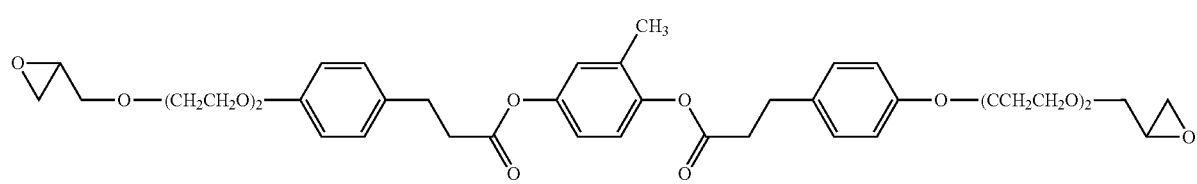
(1-2-36)
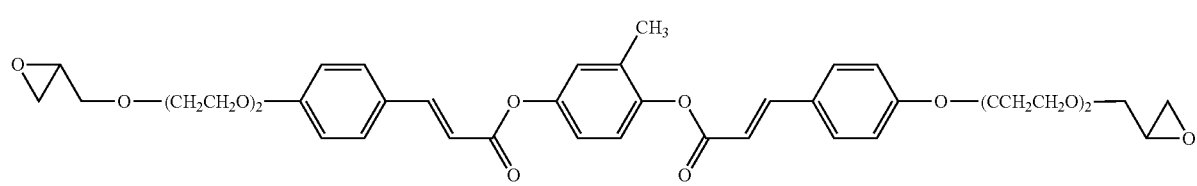
(1-2-37)
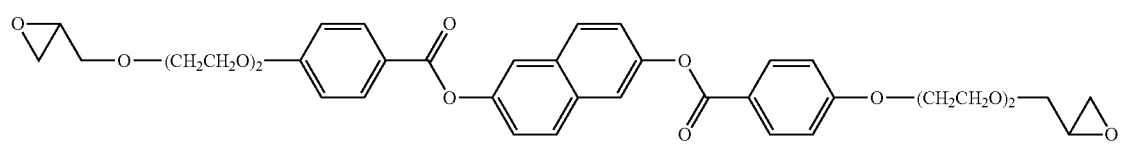
(1-2-38)
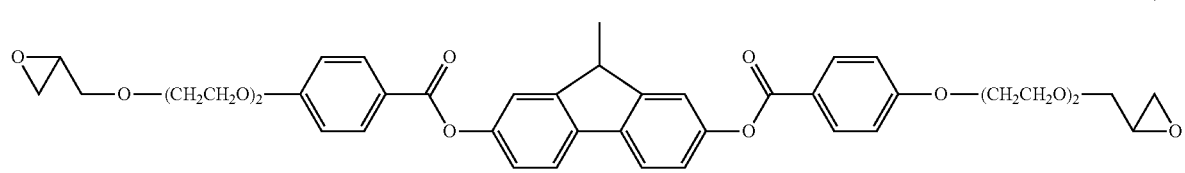
(1-2-39)
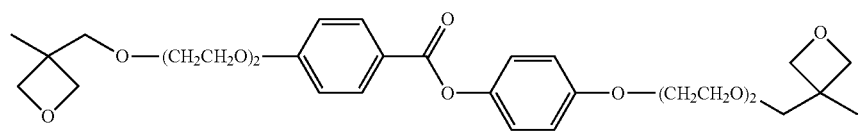
(1-3-1)

-continued
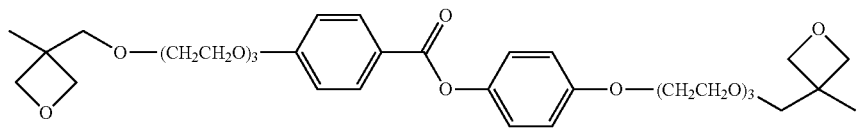 (1-3-2)
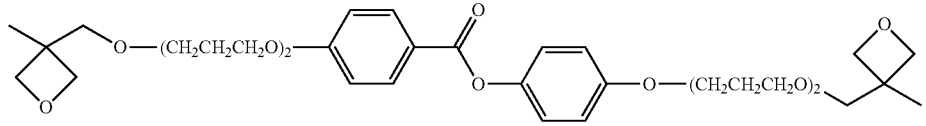 (1-3-3)
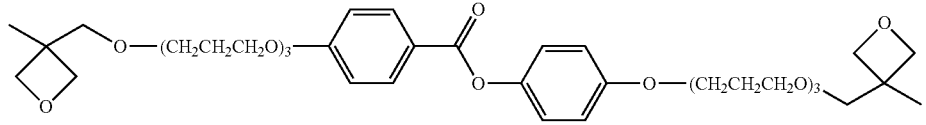 (1-3-4)
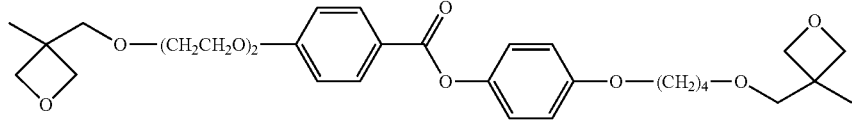 (1-3-5)
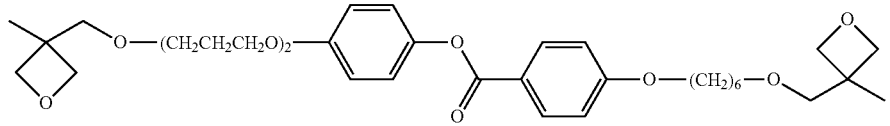 (1-3-6)
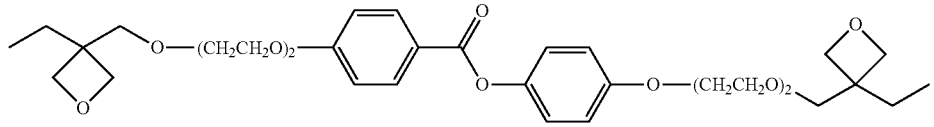 (1-3-7)
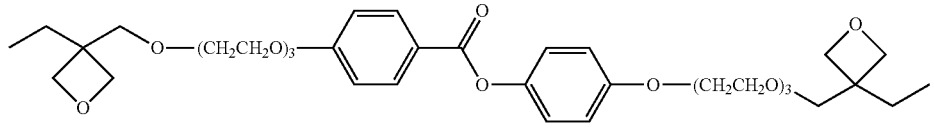 (1-3-8)
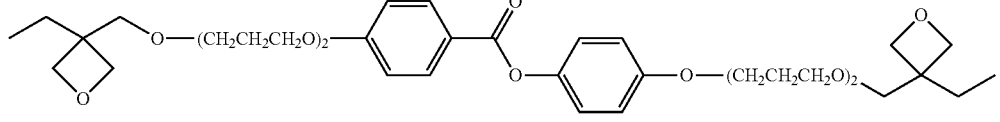 (1-3-9)
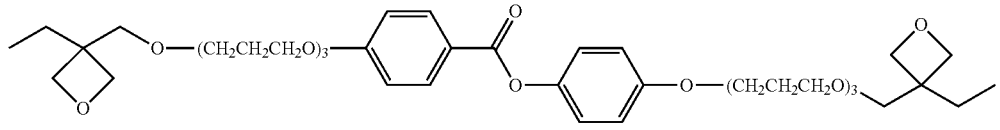 (1-3-10)
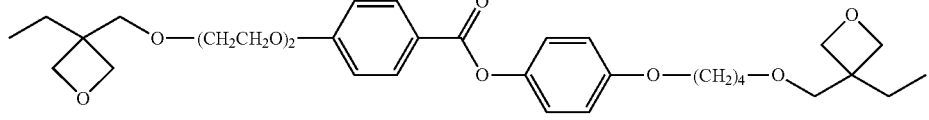 (1-3-11)
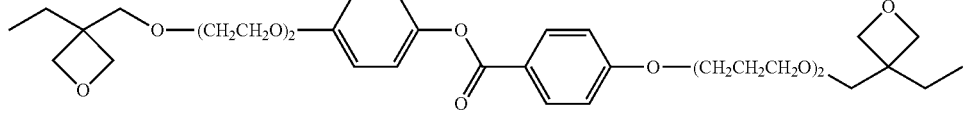 (1-3-12)

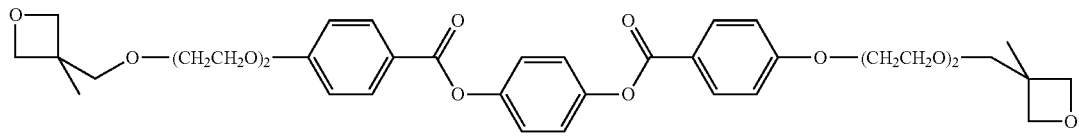
(1-3-13)
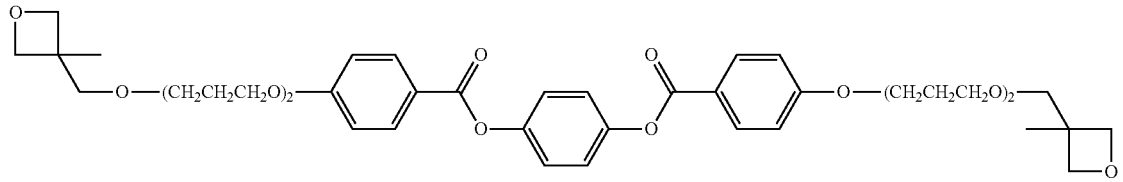
(1-3-14)
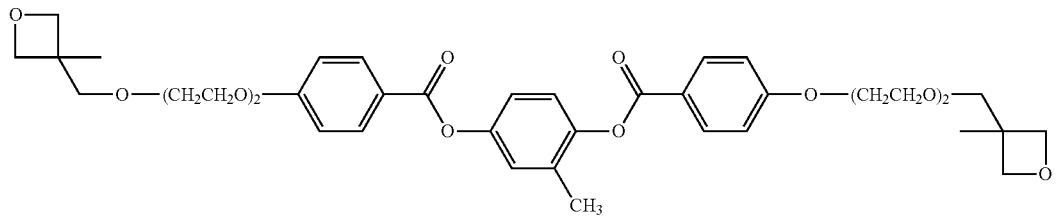
(1-3-15)
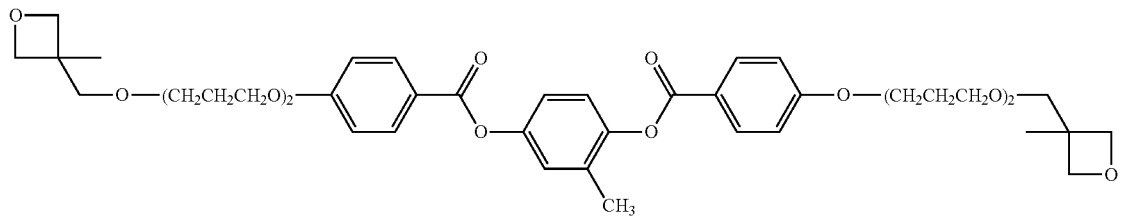
(1-3-16)
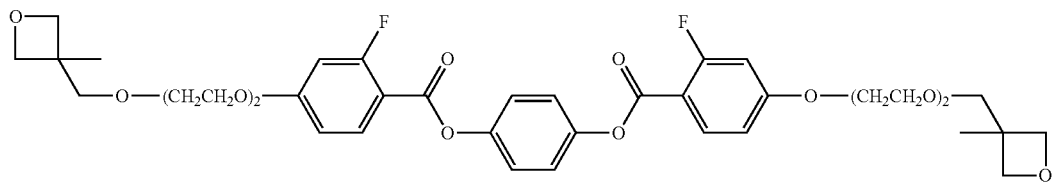
(1-3-17)
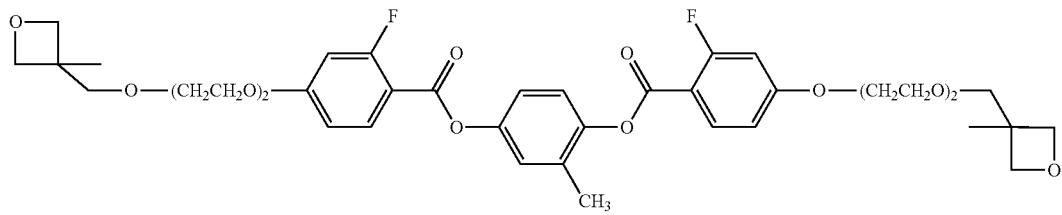
(1-3-18)
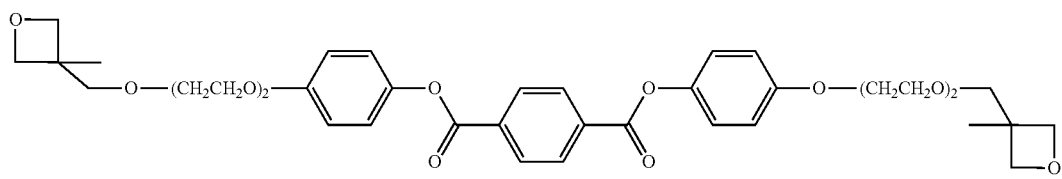
(1-3-19)
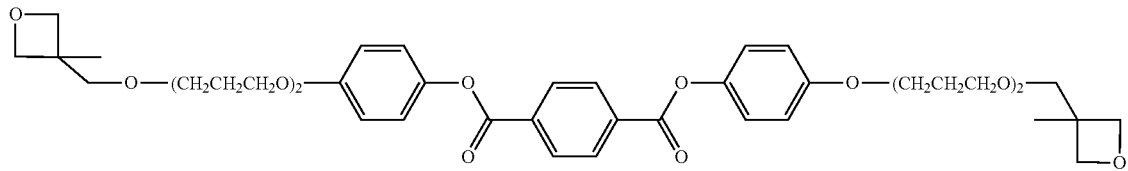
(1-3-20)

-continued
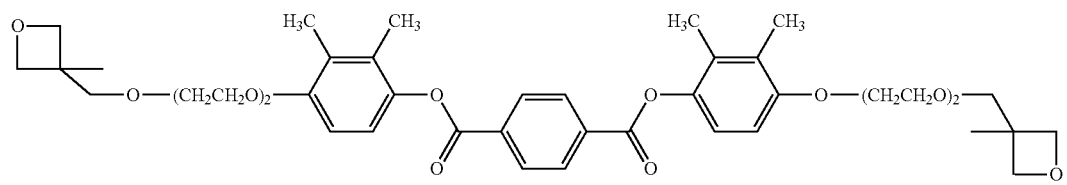
(1-3-21)
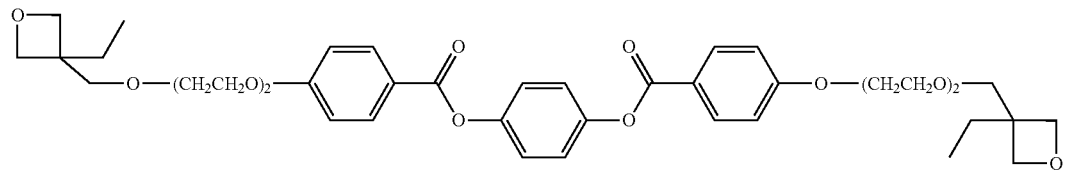
(1-3-22)
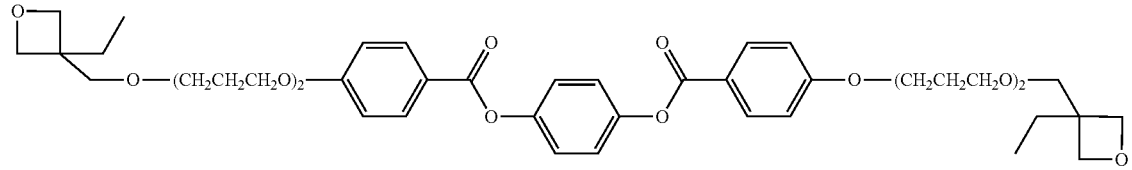
(1-3-23)
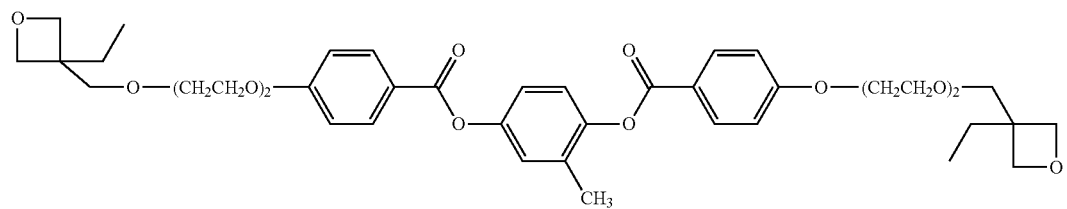
(1-3-24)
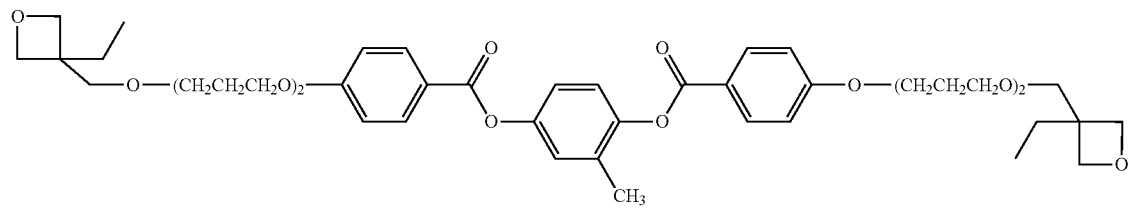
(1-3-25)
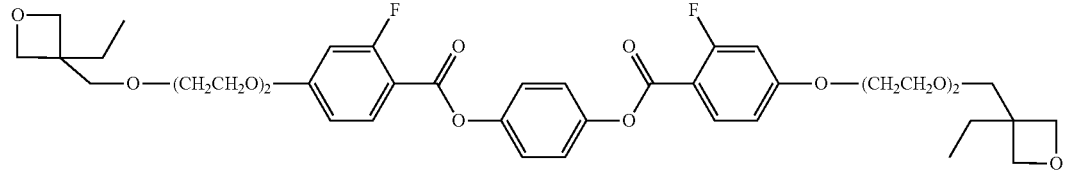
(1-3-26)
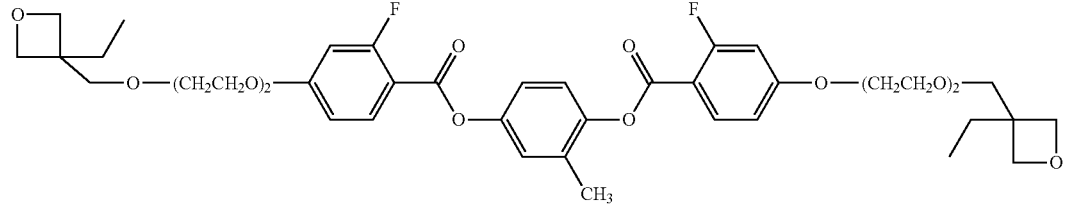
(1-3-27)
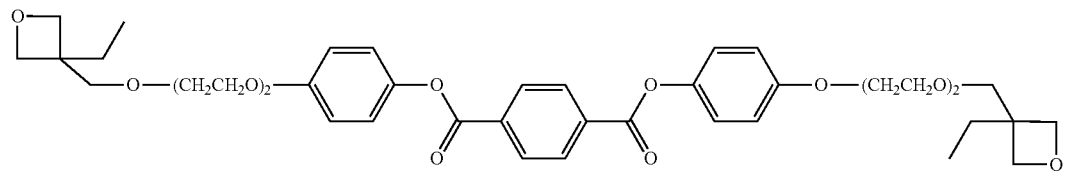
(1-3-28)

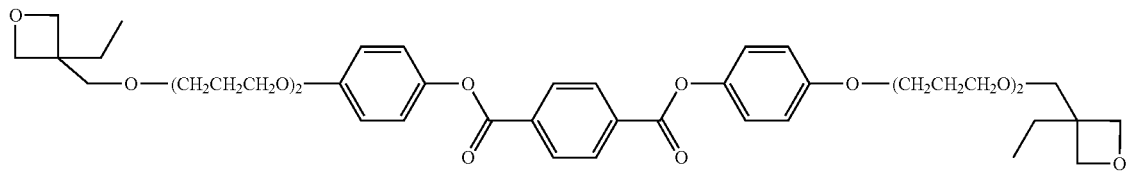
(1-3-29)
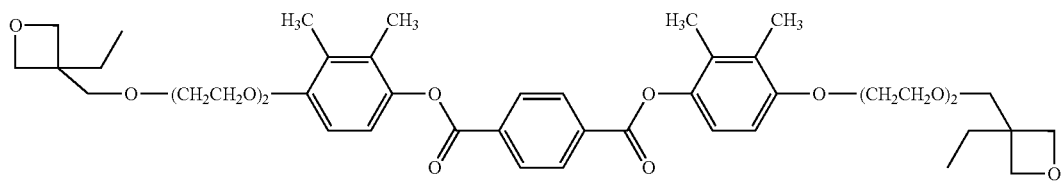
(1-3-30)
(1-3-31)
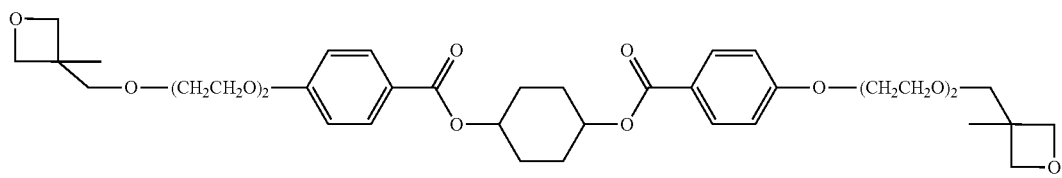
(1-3-32)
(1-3-33)
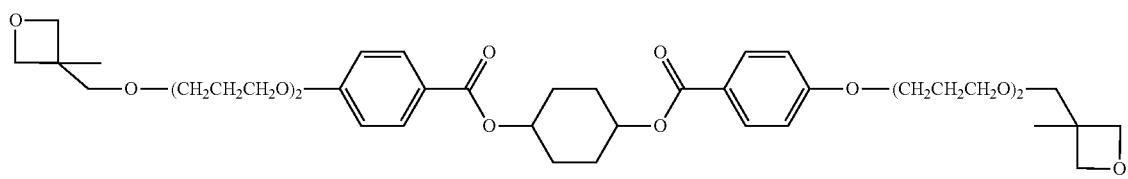
(1-3-34)
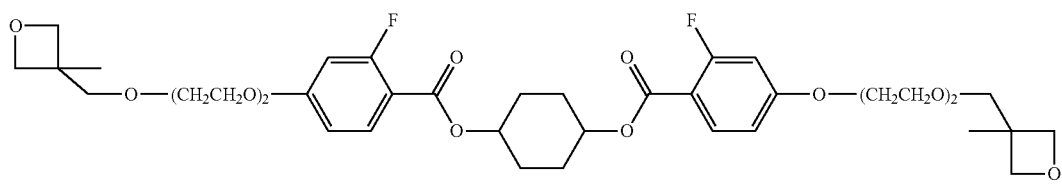
(1-3-35)
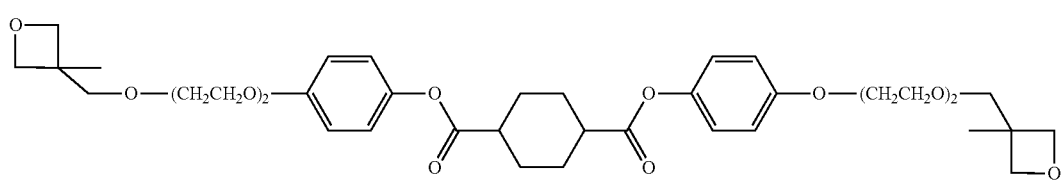
(1-3-36)
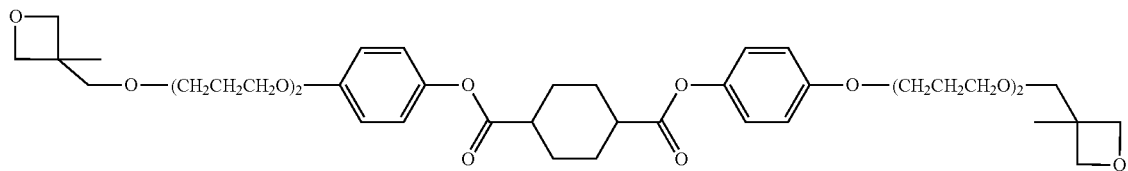
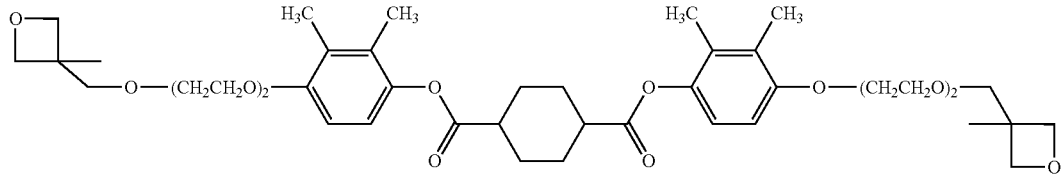

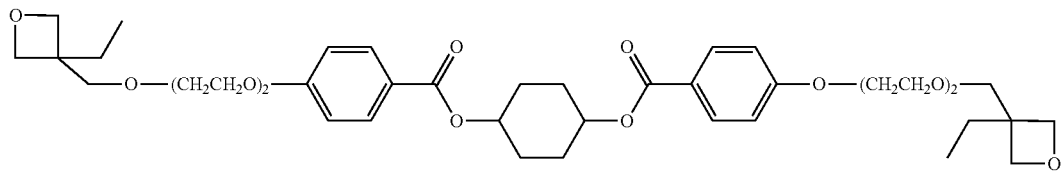
(1-3-37)
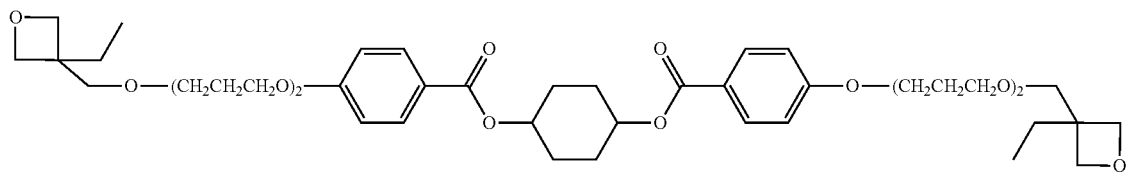
(1-3-38)
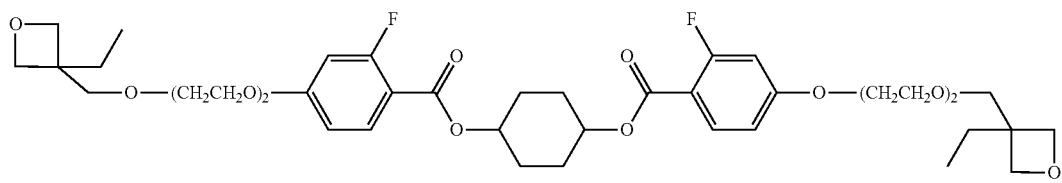
(1-3-39)
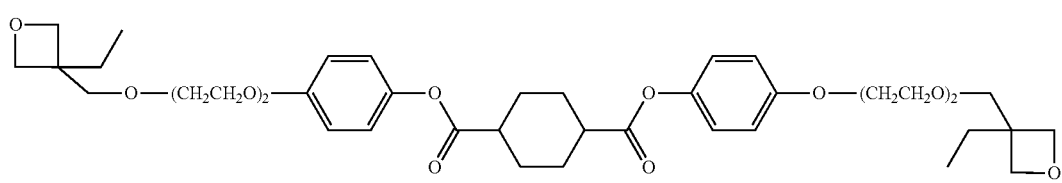
(1-3-40)
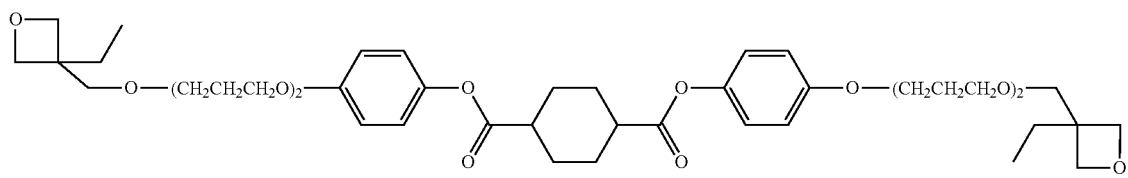
(1-3-41)
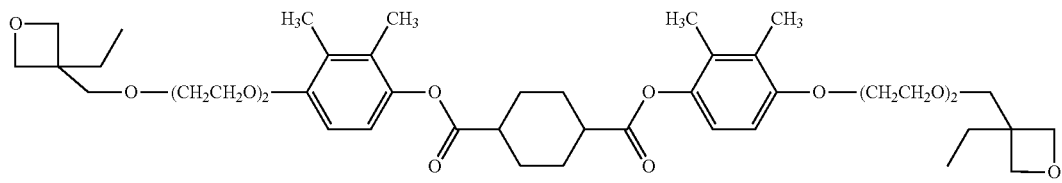
(1-3-42)
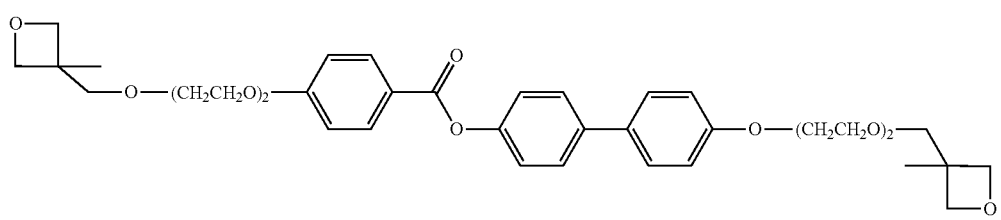
(1-3-43)
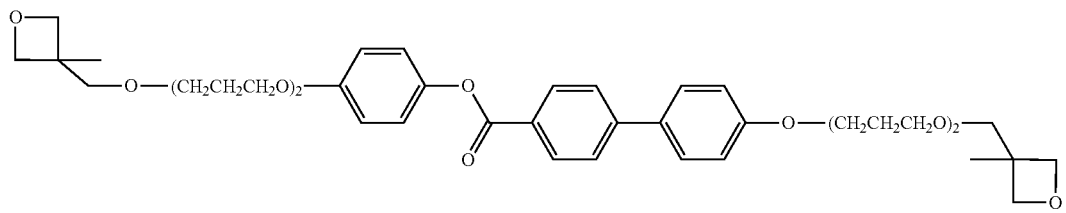
(1-3-44)

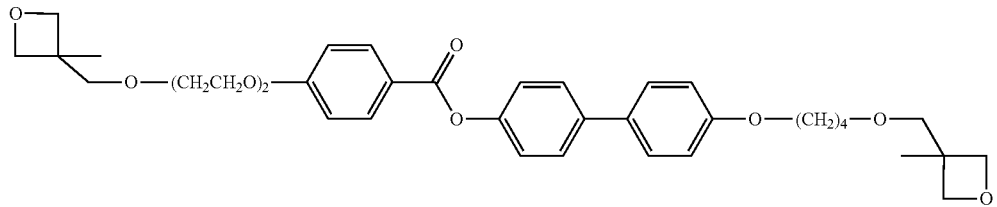
(1-3-45)
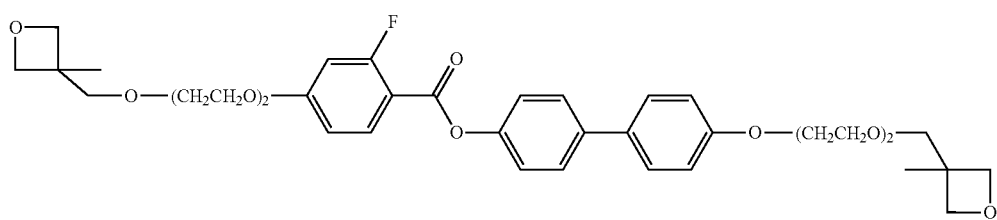
(1-3-46)
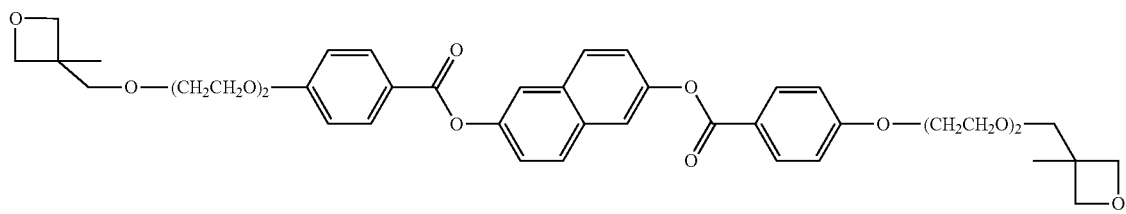
(1-3-47)
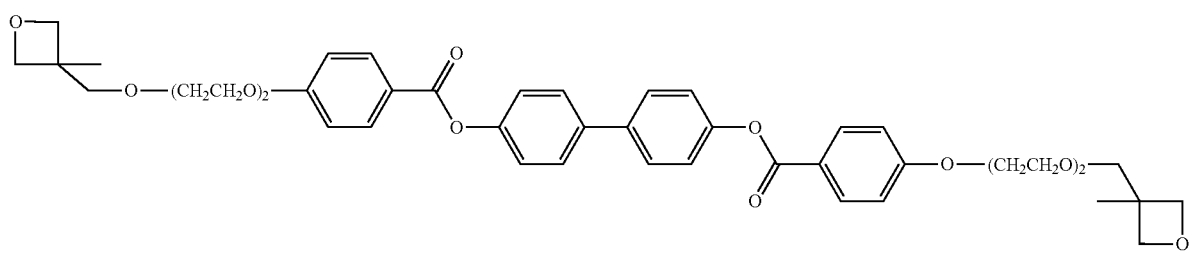
(1-3-48)
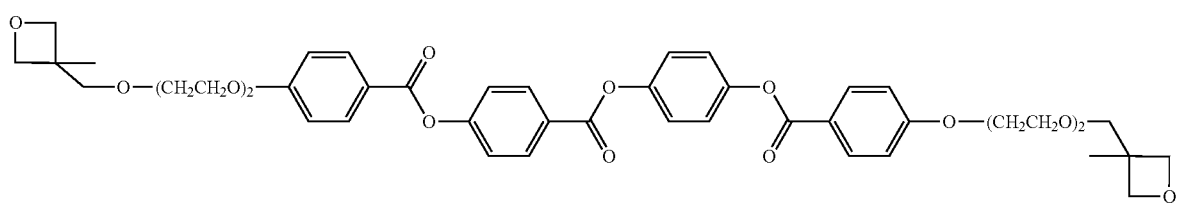
(1-3-49)
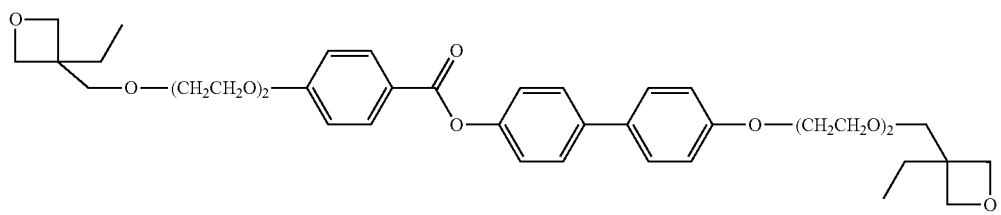
(1-3-50)
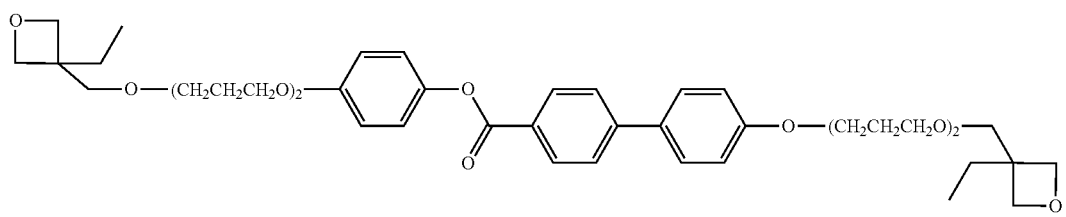
(1-3-51)

(1-3-52)
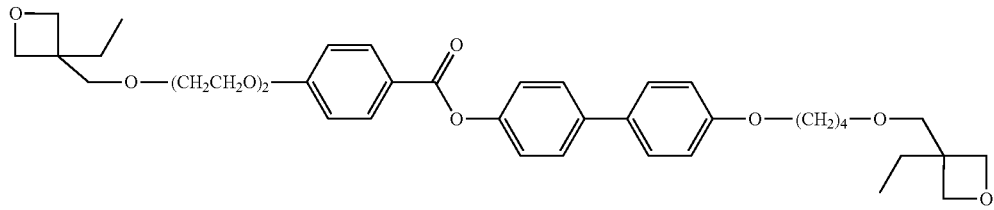
(1-3-53)
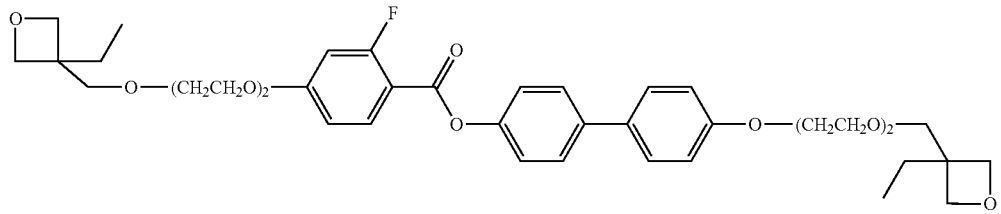
1-3-54)
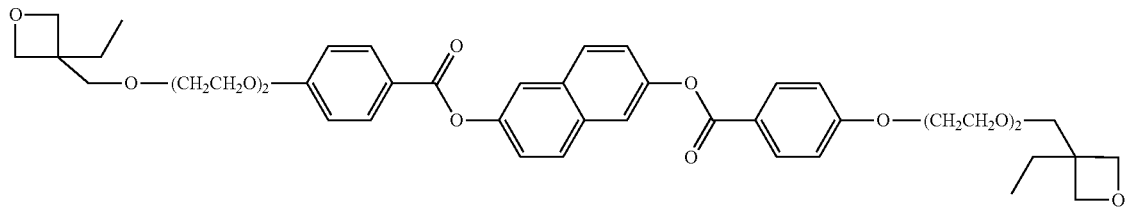
(1-3-55)
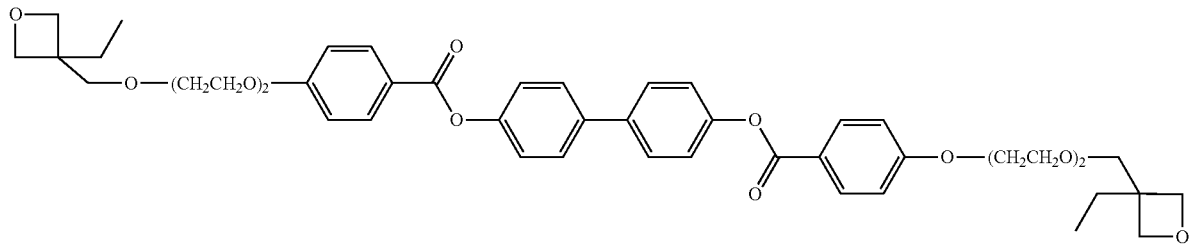
(1-3-56)
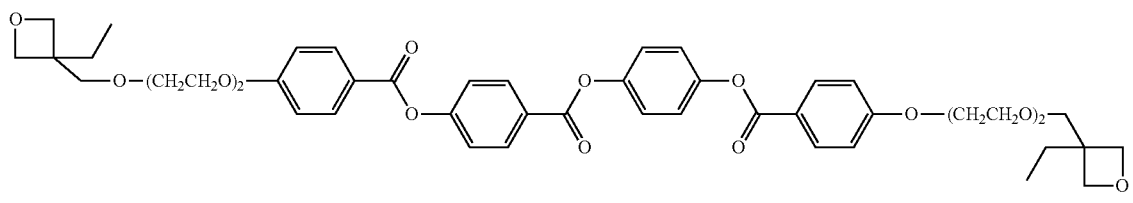
(1-3-57)
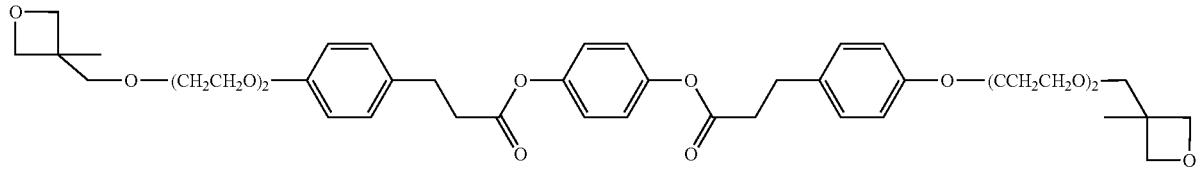
(1-3-58)
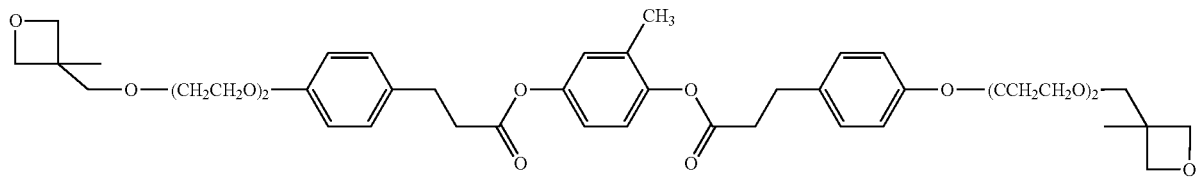

(1-3-59)
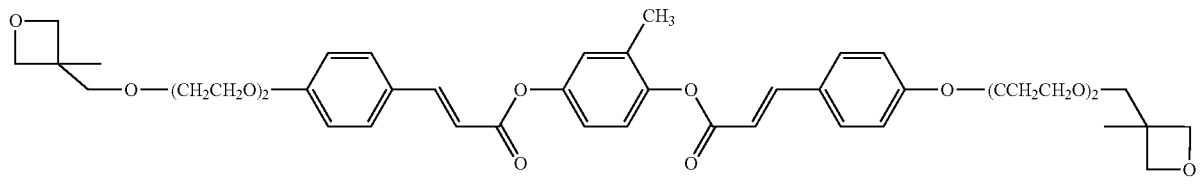
(1-3-60)
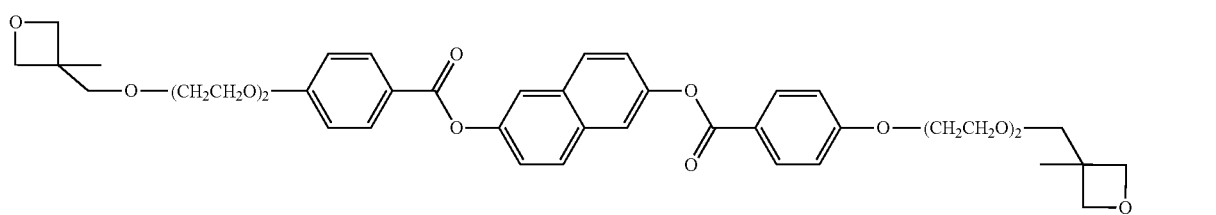
(1-3-61)
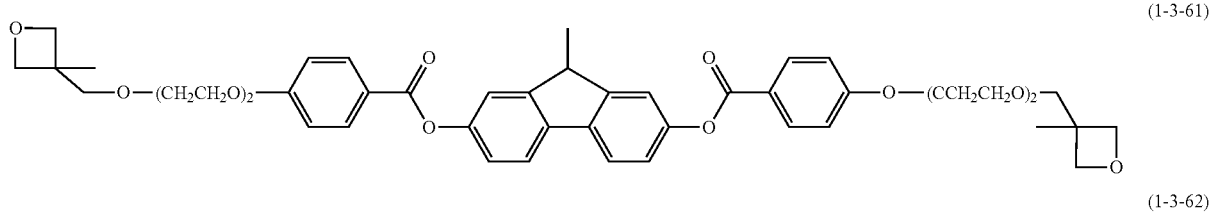
(1-3-62)
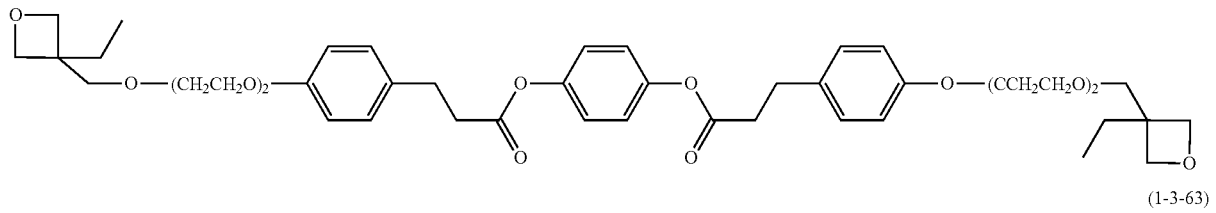
(1-3-63)
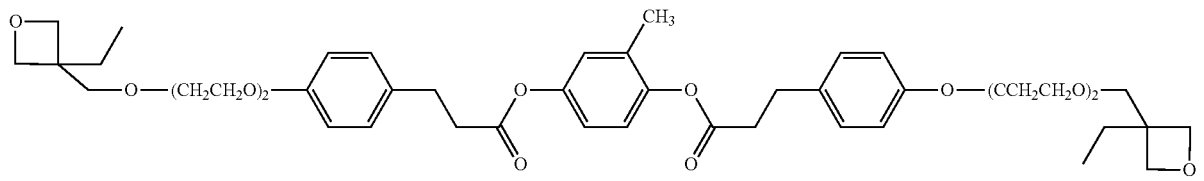
(1-3-64)
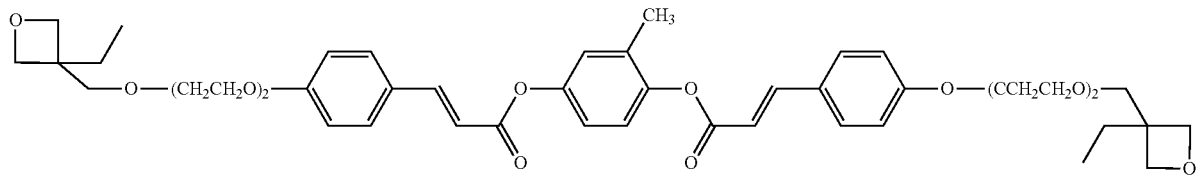
(1-3-65)
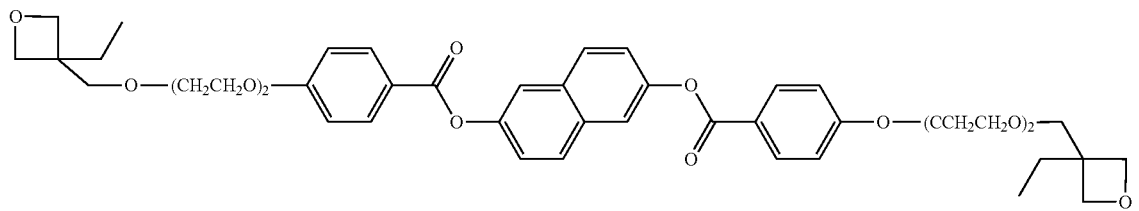

-continued

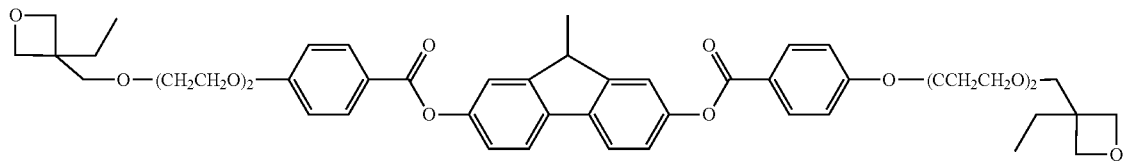
(1-3-66)

Next, the polymerizable liquid crystal composition of the invention will be explained. The composition of the invention includes at least one of the compound (1) and at least one compound selected from the group of compounds represented by formula (M1), formula (M2), formula (M3) and formula (M4). The compounds (M1), (M2) and (M3) have the ability to exhibit a wide range of a liquid crystal phase and also can form a three-dimensional network, because they have two polymerizable groups in their structure, and they make it possible to form a polymer having a high mechanical strength. Since the compound (M4) is monofunctional and possess a substituent such as a polar group at the opposite side of a polymerizable group in the major axis direction of the molecules, an adjustment of orientation in a liquid crystal state can be attained. In any one of the compounds (M1) to (M4), a compound in which the ring $A^3$ is 1,4-phenylene gives a composition having a high optical anisotropy ($\Delta n$), and a compound in which the ring $A^3$ is 1,4-cyclohexylene gives a composition having a low optical anisotropy ($\Delta n$).

Desirable examples of the compound (M1), the compound (M2), the compound (M3) and the compound (M4) include the compound (M1-1) to the compound (M1-8), the compound (M2-1) to the compound (M2-18), the compound (M3-1) to the compound (M3-4) and the compound (M4-1) to the compound (M4-18), and are as follows.

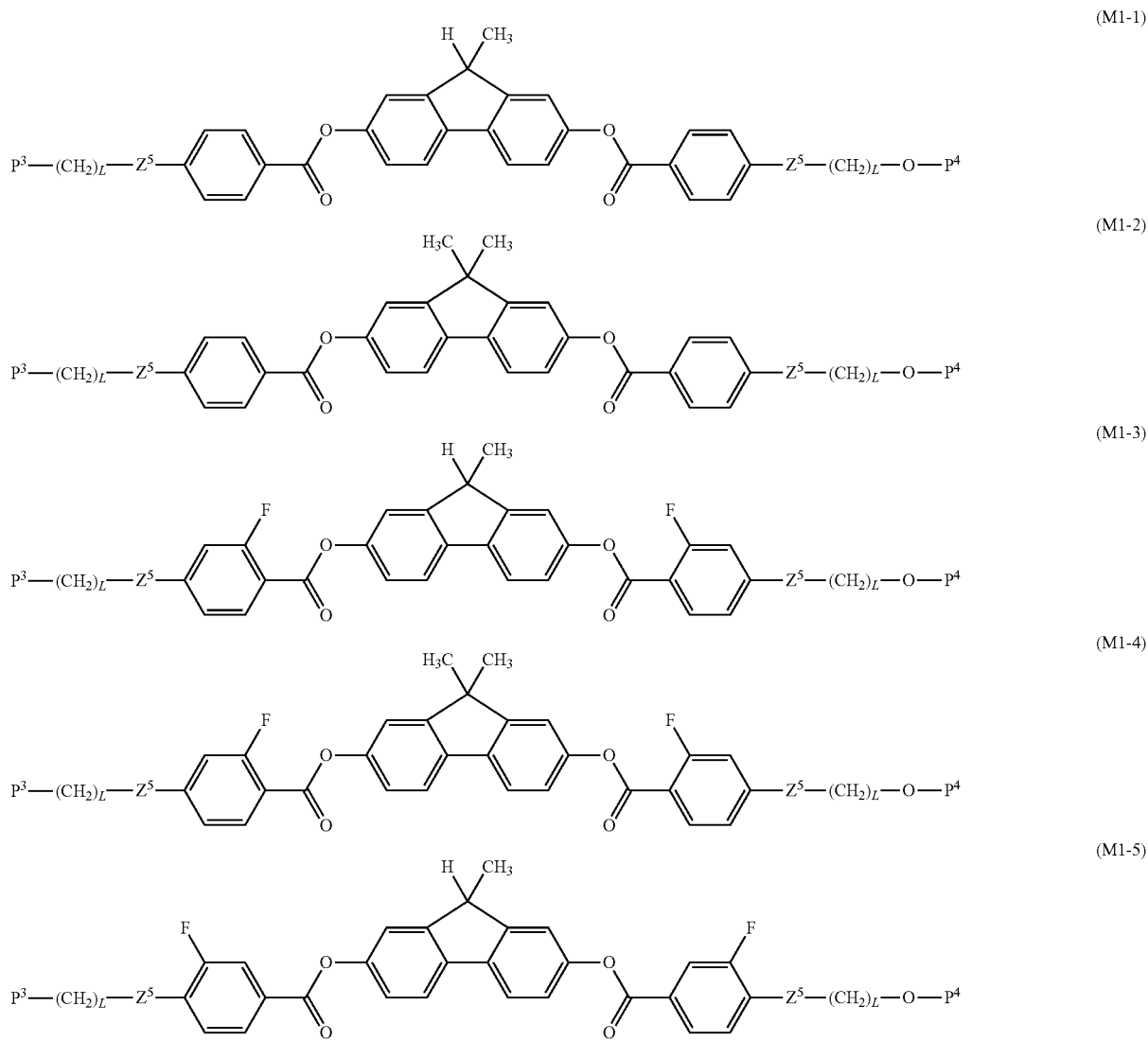

(M1-6)
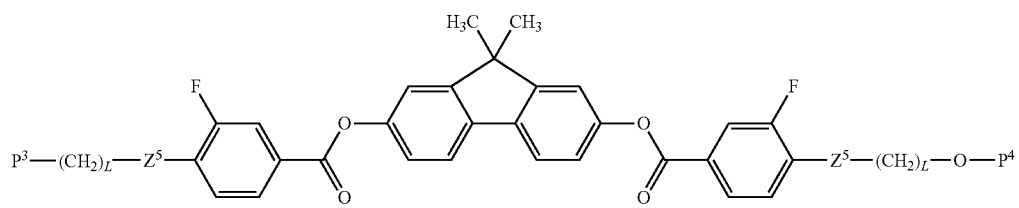
(M1-7)
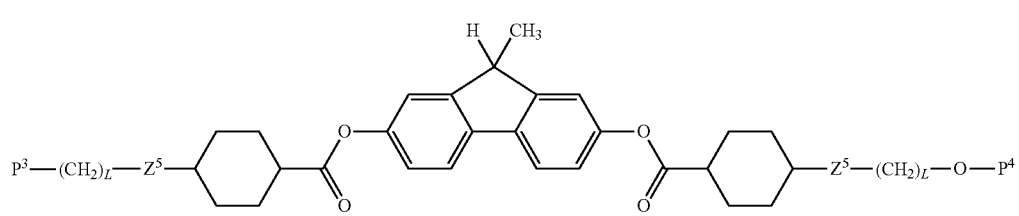
(M1-8)
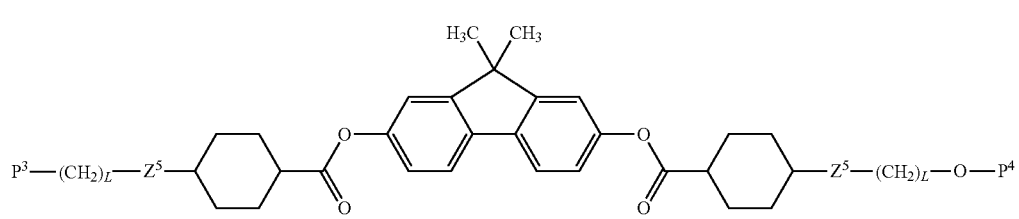
(M2-1)
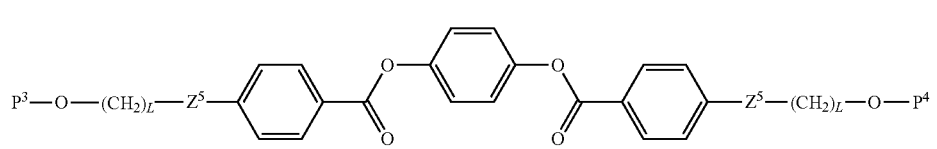
(M2-2)
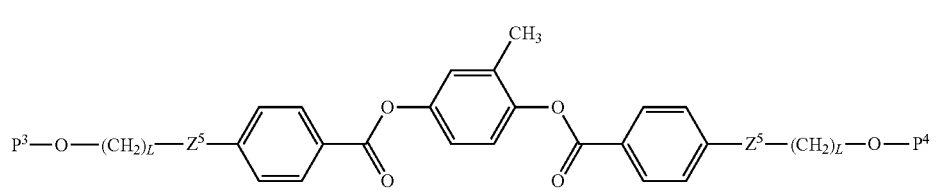
(M2-3)
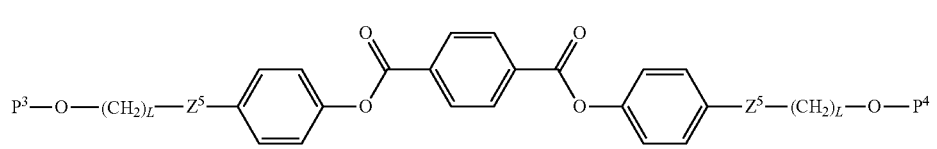
(M2-4)
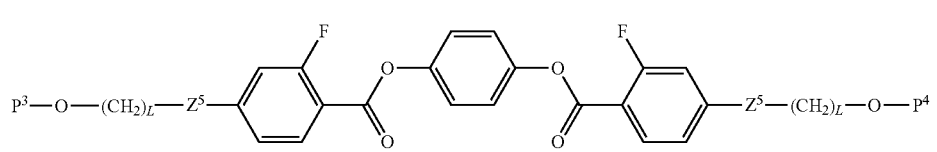
(M2-5)
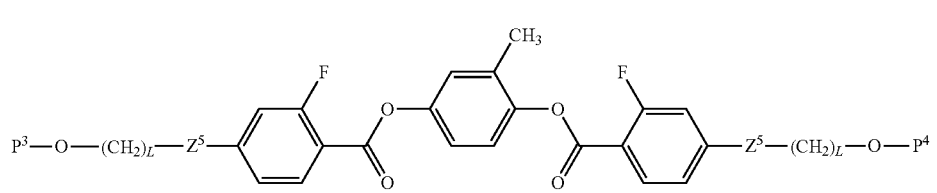
(M2-6)
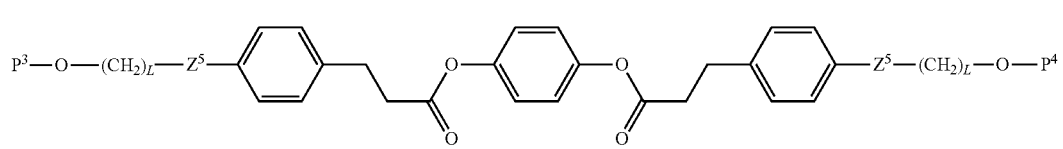

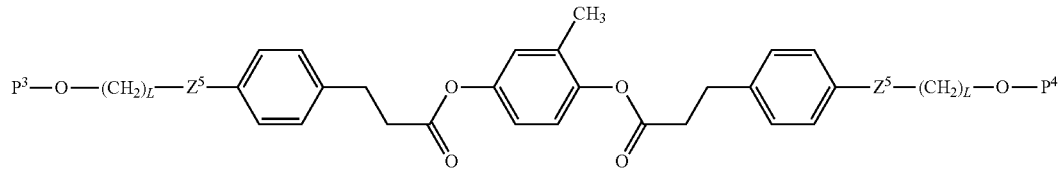
(M2-7)
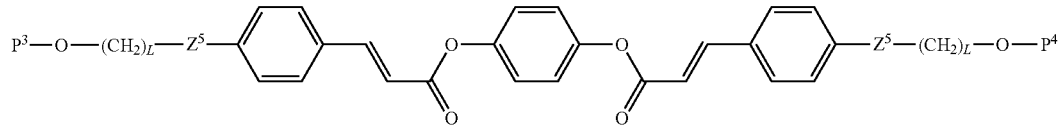
(M2-8)
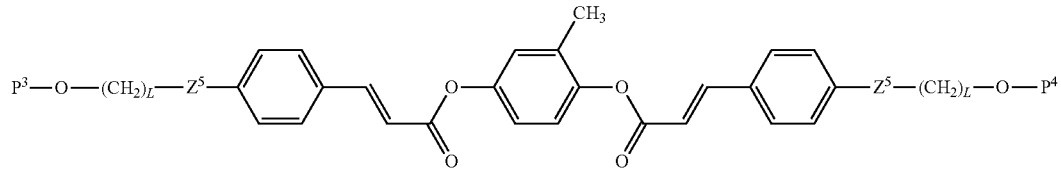
(M2-9)
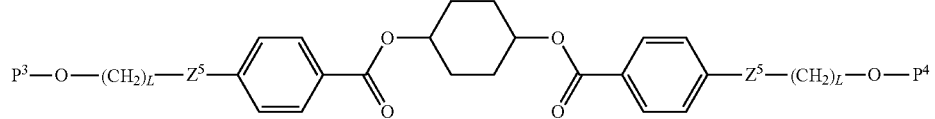
(M2-10)
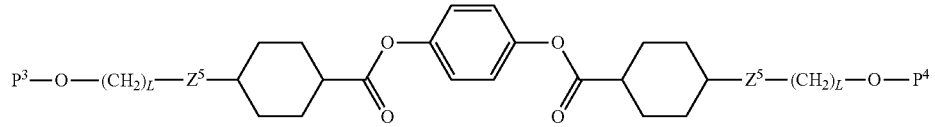
(M2-11)
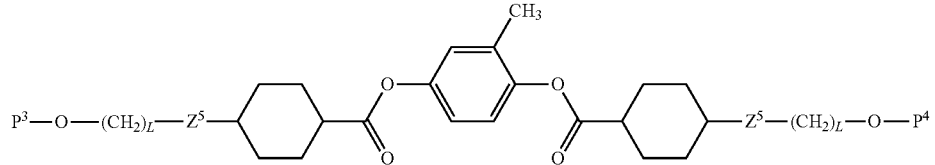
(M2-12)
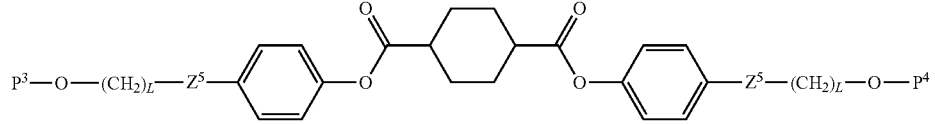
(M2-13)
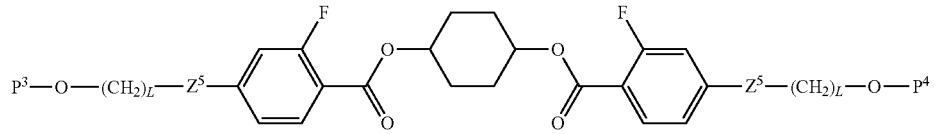
(M2-14)
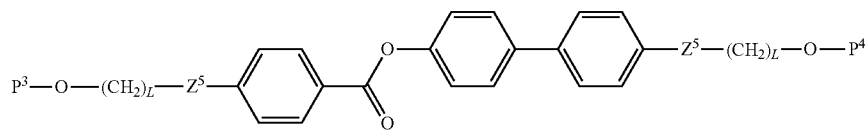
(M2-15)
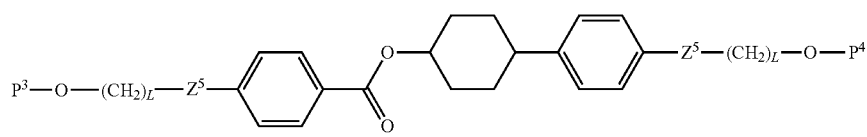
(M2-16)

-continued
(M2-17)
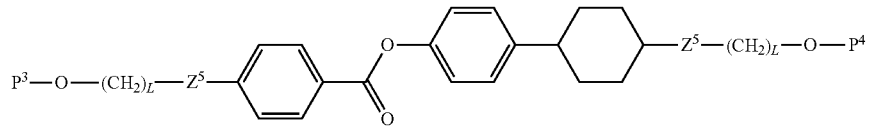
(M2-18)
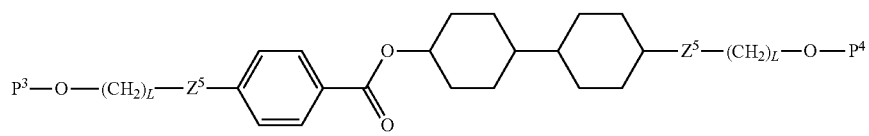
(M3-1)
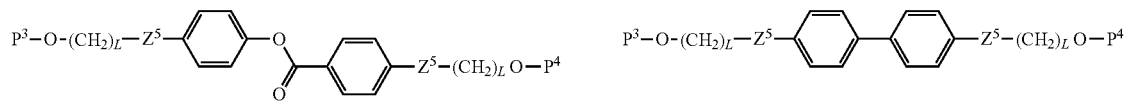
(M3-2)
(M3-3)
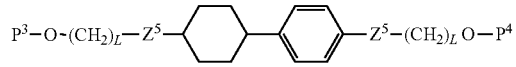
(M3-4)
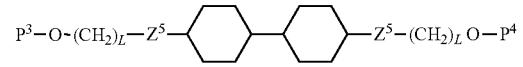
(M4-1)
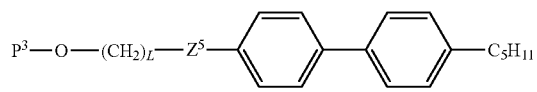
(M4-2)
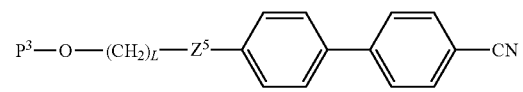
(M4-3)
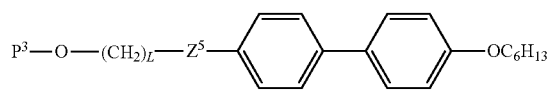
(M4-4)
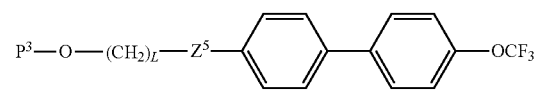
(M4-5)
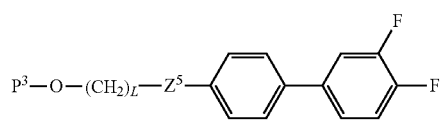
(M4-6)
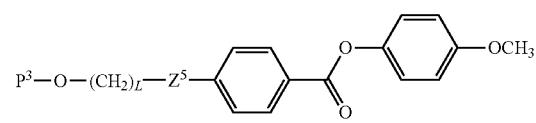
(M4-7)
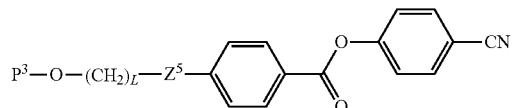
(M4-8)
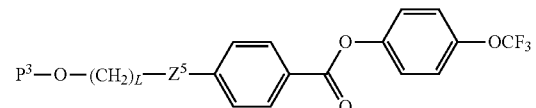
(M4-9)
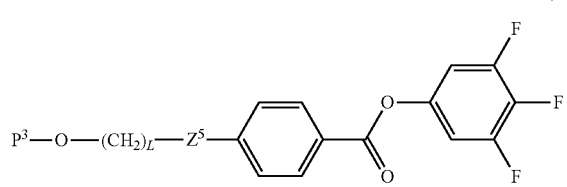
(M4-10)
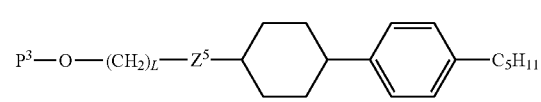
(M4-11)
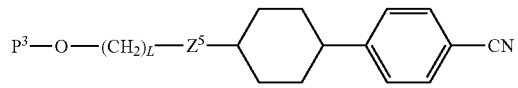
(M4-12)
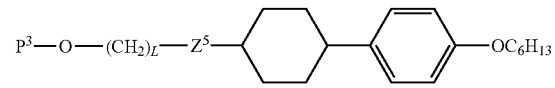
(M4-13)
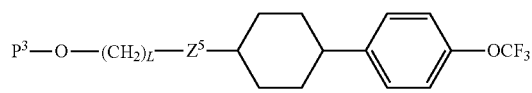
(M4-14)
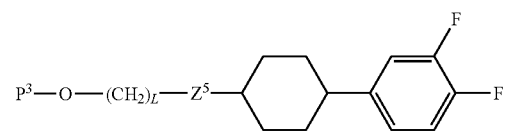

(M4-15)

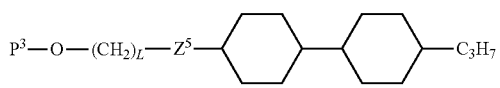

(M4-16)

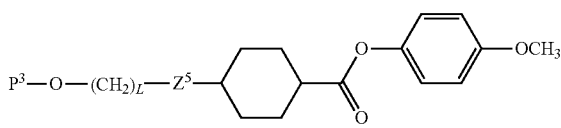

(M4-17)

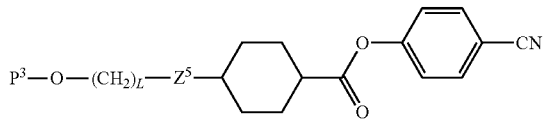

(M4-18)

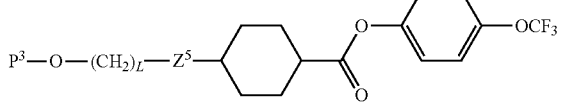

In these compounds, $Z^5$ and L have the same meanings with those in formulas (M1) to (M4) described above, and $P^3$ and $P^4$ are a group represented by any one of formula (2-1) to formula (2-3):

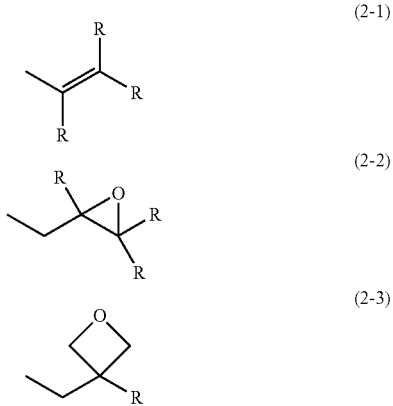

wherein R is independently hydrogen, halogen or alkyl having 1 to 5 carbons.

In the following explanation, the compound (M1), the compound (M2), the compound (M3) and the compound (M4) are generically referred to as the compound (M). The polymerizable liquid crystal composition of the invention includes at least one of the compound (1) and at least one of the compound (M) as described above. A desirable ratio of the compound (1) in the polymerizable liquid crystal composition of the invention is in the range of approximately 5% to approximately 95% by weight based on the total amount of the compound (1) and the compound (M). A more desirable ratio is in the range of approximately 10% to approximately 90% by weight, and an even more desirable ratio is in the range of approximately 20% to approximately 70% by weight. A desirable ratio of the compound (M) is in the range of approximately 5% to approximately 95% by weight based, on the total amount of the compound (1) and the compound (M). A more desirable ratio is in the range of approximately 10% to approximately 90% by weight and an even more desirable ratio is in the range of approximately 30% to approximately 80% by weight. Although it is desirable that the polymerizable liquid crystal composition of the invention is composed of the compound (1) and the compound (M), the composition may further include another component.

Non-liquid crystal polymerizable compound can be added to the polymerizable liquid crystal composition of the invention for the purpose of adjusting the ability to form a coat, mechanical strength or the like. A desirable example of the non-liquid crystal polymerizable compound includes (meth) acrylate compounds, vinyl compounds, styrene compounds, vinyl ether compounds, allyl ether compounds, epoxy compounds and oxetane compounds.

A desirable example of the non-liquid crystal polymerizable compound includes methyl(meth)acrylate, ethyl(meth) acrylate butyl(meth)acrylate, 2-ethylhexyl(meth)acrylate, phenyl(meth)acrylate, vinyl chloride, vinyl fluoride, vinyl acetate, vinyl pivalate, vinyl 2,2-dimethylbutanate, vinyl 2,2-dimethylpentanoate, vinyl 2-methyl-2-butanoate, vinyl propionate, vinyl stearate, vinyl 2-ethyl-2-methylbutanoate, N-vinylacetoamide, vinyl p-t-butylbenzoate, vinyl N,N-dimethylaminobenzoate, vinyl benzoate, stylene, o-, m- or p-chloromethylstylene, α-methylstylene, tetrafluoroethylene and hexafluoropropene, and further includes ethyl vinyl ether, hydroxybutyl monovinyl ether, t-amyl vinyl ether and cyclohexanedimethanol methyl vinyl ether. 3-ethyl-3-hydroxymethyloxetane, 3-methyl-3-hydroxymethyloxetane, di(3-ethyl-oxetan-3-ylmethyl) or 3-ethyl-3-(2-ethylhexyloxymethyl) oxetane is also added for the purpose of adjusting the viscosity of the composition or avoiding shrinkage caused by curing.

A polyfunctional acrylate can be added to the composition for further increasing the ability to form a coat. A desirable polyfunctional acrylate includes 1,4-butanedioldiacrylate, 1,6-hexanedioldiacrylate, 1,9-nonanedioldiacrylate, neopentyl glycol diacrylate, triethylene glycol diacrylate, dipropylene glycol diacrylate, tripropylene glycol diacrylate, tetraethylene glycol diacrylate, trimethylolpropane triacrylate, ethylene oxide modified trimethylolpropane triacrylate, pentaerythritol triacrylate, tris(acryloyloxyethy)phosphate, ethylene oxide modified bisphenol A diacrylate, bisphenol A glycidyl diacrylate (trade name: Viscoat #700 available from Osaka Organic Chemical Industry Ltd.,) and polyethylene glycol diacrylate.

A polyfunctional cationic polymerizable compound can also be added to the composition for increasing the ability to form a coat. A desirable example of the compound includes the following compounds (3-1) to (3-10). The compound may be added to the polymerizable liquid crystal composition of the invention for adjusting the viscosity, adjusting the alignment, or increasing the hardness of the polymer.

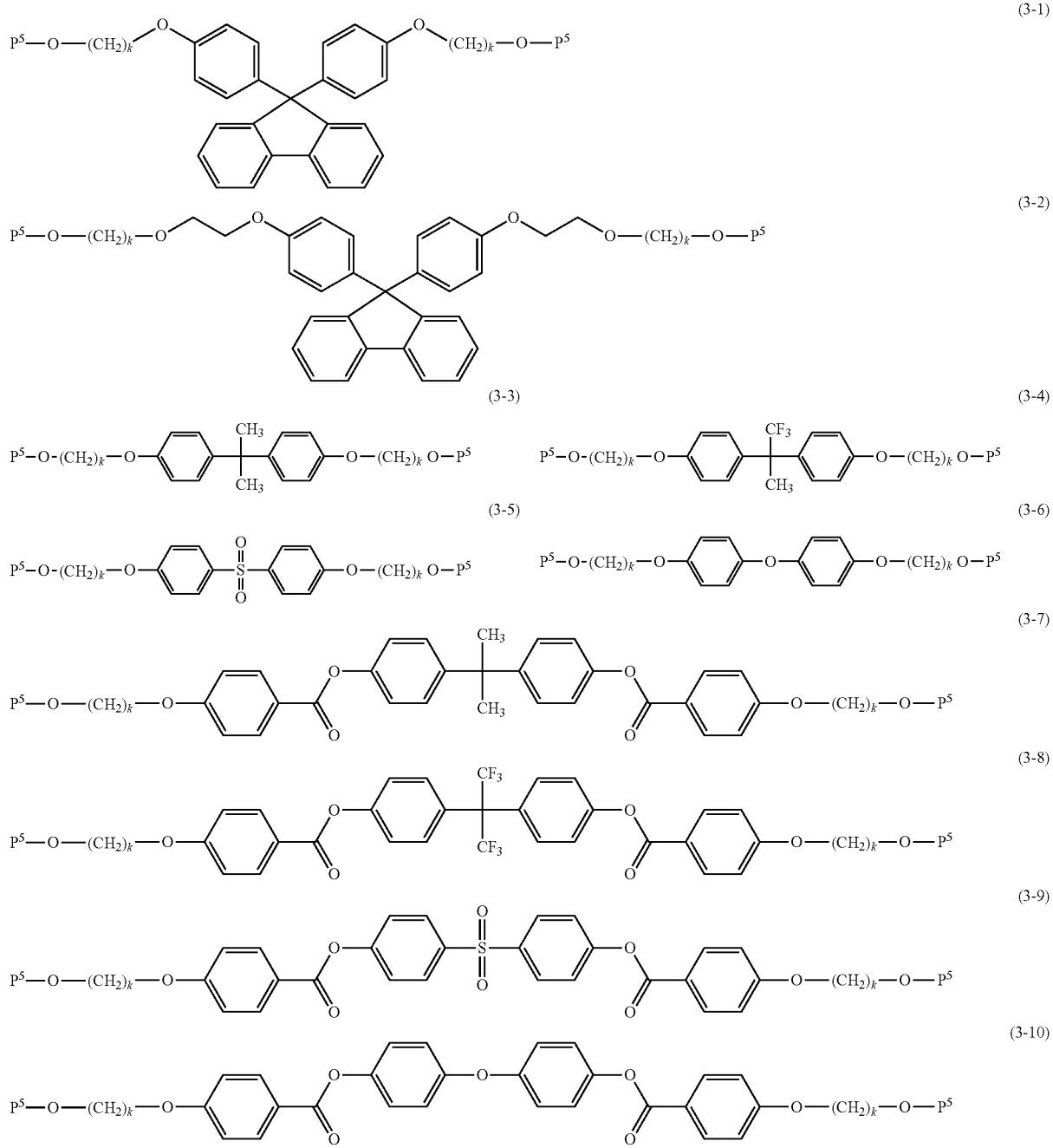

In these compounds, k is an integer of 2 to 10 and $P^5$ is a group represented by any one of formula (2-1) to formula (2-3) described above. An example of another polymerizable compound includes an epoxy-type compound having one polymerizable group and an epoxy-type compound having two or more polymerizable groups. An example of epoxy resins that may be added to the composition includes, but is not limited to, epoxy resins that can be derived from divalent phenols, such as bisphenol A-type epoxy resins, bisphenol F-type epoxy resins, bisphenol S-type epoxy resins, bisphenol AD-type epoxy resins, resorcinol-type epoxy resins, hydroquinone-type epoxy resins, catechol-type epoxy resins, dihydroxynaphthalene-type epoxy resins, biphenyl-type epoxy resins and tetramethylbiphenyl-type epoxy resins; epoxy resins that can be derived from trivalent or polyvalent phenols, such as phenol novolac-type epoxy resins, cresol novolac-type epoxy resins, triphenylmethane-type epoxy resins, tetraphenylethane-type epoxy resins, dicyclopentadiene-phenol modified epoxy resins, phenol aralkyl-type epoxy resins, biphenyl aralkyl-type epoxy resins, naphthol novolac-type epoxy resins, naphthol aralkyl-type epoxy resins, naphthol-phenol cocondensated novolac-type epoxy resins, naphthol-cresol cocondensed novolac-type epoxy resins, aromatic hydrocarbon formaldehyde resin-modified phenol resin-type epoxy resins and biphenyl-modified novolac-type epoxy resins; tetrabromobisphenol A-type epoxy resins, brominated phenol novolac-type epoxy resins, polycarboxylic acid polyglycidyl ester, polyol polyglycidyl ether, aliphatic acid-type epoxy resins, alicyclic epoxy resins, glycidylamine-type epoxy resins, triphenolmethane-type epoxy resins and dihydroxybenzene-type epoxy resins. These epoxy resins may be solely used or two or more epoxy resins may be mixed.

A specific example of epoxy-type compounds includes, alkyl monoglycidyl ether having 2 to 25 carbons (for example, butyl glycidyl ether, 2-ethylhexyl glycidyl ether, decyl glycidyl ether, stearyl glycidyl ether), butanediol diglycidyl ether, 1,6-hexanediol diglycidyl ether, neopentylglycol diglycidyl ether, dodecanediol diglycidyl ether, pentaethyltriol polyglycidyl ether, trimethylolpropane polyglycidyl ether, glycerol polyglycidyl ether, phenyl glycidyl ether, p-sec-butylphenyl glycidyl ether, p-tert-butylphenyl glycidyl ether, resorcinol glycidyl ether, allyl glycidyl ether, tetrafluoropropyl glycidyl ether, octafluoropropyl glycidyl ether, dodecafluoropentyl glycidyl ether, stylene oxide, 1,7-octadiene diepoxide, limonene diepoxide, limonene monoxide, α-pinene epoxide, β-pinene epoxide, cyclohexene epoxide, cyclooctene epoxide, vinylcyclohexene oxide, butoxy polyethylene glycol glycidyl ether, polyethylene glycol diglycidyl ether, 3,4-epoxycyclohexenylmethyl-3',4'-epoxycyclohexene carboxylate, 3,4-epoxycyclohexenylethyl-3',4'-epoxycyclohexene carboxylate, 1,2-epoxy-4-vinylcyclohexane, vinylcyclohexene dioxide, allylcyclohexene dioxide, 1-epoxyethyl-3,4-epoxycyclohexane, 3,4-epoxy-4-methylcyclohexyl-2-propylene oxide, bis(3,4-epoxycyclohexyl)ether, bis (3,4-epoxycyclohexylmethyl)adipate, diglycidyl phthalate, diglycidyl terephthalate, diglycidyl hexahydrophthalate, diglycidyl tetrahydrophthalate, tris(2,3-epoxypropyl)isocyanurate, 3-ethyl-3-hydroxymethyloxetane, 3-ethyl-3-(phenoxymethyl)oxetane, di(1-ethyl(3-oxetanyl))methyl ether, 3-ethyl-3-hydroxymethyloxetane, 3-methyl-3-hydroxymethyloxetane, di(3-ethyl-oxetan-3-ylmethyl) and 3-ethyl-3-(2-ethylhexyloxymethyl)oxetane. A specific example further includes vinyl-type compounds such as ethyl vinyl ether, hydroxybutyl monovinyl ether, t-amyl vinyl ether and cyclohexanedimethanol methyl vinyl ether in addition to the epoxy-type compounds described above.

Next, a nonionic surfactant will be explained. A desirable example of a nonionic surfactant includes a fluorine-based nonionic surfactant, a silicone-based nonionic surfactant and a hydrocarbon-based nonionic surfactant. An example of the fluorine-based nonionic surfactant includes BYK-340, Futargent 251, Futargent 221MH, Futargent 250, FTX-215M, FTX-218M, FTX-233M, FTX-245M, FTX-290M, FTX-209F, FTX-213F, Futargent 222F, FTX-233F, FTX-245F, FTX-208G, FTX-218G, FTX-240G, FTX-206D, Futargent 212D, FTX-218, FTX-220D, FTX-230D, FTX-240D, FTX-720C, FTX-7400, FTX-207S, FTX-211S, FTX-220S, FTX-230S, KB-L82, KB-L85, KB-L97, KB-L109, KB-L110, KB-F2L, KB-F2M, KB-F2S, KB-F3M and KB-FaM.

An example of the silicone-based nonionic surfactant includes Polyflow ATF-2, Granol 100, Granol 115, Granol 400, Granol 410, Granol 435, Granol 440, Granol 450, Granol B-1484, Polyflow KL-250, Polyflow KL-260, Polyflow KL-270, Polyflow KL-280, BYK-300, BYK-302, BYK-306, BYK-307, BYK-310, BYK-315, BYK-320, BYK-322, BYK-323, BYK-325, BYK-330, BYK-331, BYK-333, BYK-337, BYK-341, BYK-344, BYK-345, BYK-346, BYK-347, BYK-348, BYK-370, BYK-375, BYK-377, BYK-378, BYK-3500, BYK-3510 and BYK-3570. An example of the hydrocarbon-based nonionic surfactant includes Polyflow No. 3, Polyflow No. 50EHF, Polyflow No. 54N, Polyflow No. 75, Polyflow No. 77, Polyflow No. 85HF, Polyflow No. 90, Polyflow No. 95, BYK-350, BYK-352, BYK-354, BYK-355, BYK-358N, BYK-361N, BYK-380N, BYK-381, BYK-392 and BYK-Silclean3700, where the main component is an acryl-type polymer. Incidentally, both Polyflow and Granol described above are trade names of the products available from Kyoeisha Chemical Co., Ltd. BYK is a trade name of the product available from BYK Additives & Instruments. Futargent, FTX and KB are trade names of the products available from Neos Company Limited.

A surfactant other than the types described above may be used as required. A specific example includes a variety of compounds such as polyether-type compounds, acrylic acid copolymer-type compounds, titanate-type compounds, imidazoline, tertiary ammonium salts, alkylamine oxides, polyamine derivatives, polyoxyethylene-polyoxypropylene condensates, polyethylene glycol and its esters, sodium lauryl sulfate, ammonium lauryl sulfate, amine lauryl sulfates, alkyl-substituted aromatic sulfonates, alkyl phosphates, aliphatic or aromatic sulfonate formaldehyde condensates, lauryl amidopropyl betaine, lauryl aminoacetic acid betaine, polyethylene glycol aliphatic acid esters, polyoxyethylene alkylamines, perfluoroalkylsulfonic acid salts and perfluoroalkylcarboxylic acid salts. These surfactants are effective in facilitating application of the composition to a supporting substrate and, so forth.

An ordinary cationic photopolymerization initiator is added to the composition of the invention. The polymerization initiator includes diaryliodonium salts (hereinafter referred to as DAS) and triarylsulfonium salts (hereinafter referred to as TAS). An example of DAS includes diphenyliodonium tetrafluoroborate, diphenyliodonium hexafluorophosphonate, diphenyliodonium hexafluoroarsenate, diphenyliodonium trifluoromethanesulfonate, diphenyliodonium trifluoroacetate, diphenyliodonium p-toluenesulfonate, diphenyliodonium tetra(pentafluorophenyl)borate, 4-methoxyphenylphenyliodonium tetrafluoroborate, 4-methoxyphenylphenyliodonium hexafluorophosphonate, 4-methoxyphenylphenyliodonium hexafluoroarsenate, 4-methoxyphenylphenyliodonium trifluoromethanesulfonate, 4-methoxyphenylphenyliodonium trifluoroacetate, 4-methoxyphenylphenyliodonium p-toluenesulfonate, 4-methoxyphenylphenyliodonium diphenyliodonium tetra (pentafluorophenyl)borate, bis(4-tert-butylphenyl)iodonium diphenyliodonium tetrafluoroborate, bis(4-tert-butylphenyl) iodonium diphenyliodonium hexafluoroarsenate, bis(4-tert-butylphenyl)iodonium diphenyliodonium trifluoromethanesulfonate, bis(4-tert-butylphenyl)iodonium trifluoroacetate, bis(4-tert-butylphenyl)iodonium p-toluenesulfonate and bis (4-tert-butylphenyl)iodonium diphenyliodonium tetra(pentafluorophenyl)borate.

DAS can be sensitized by the addition of a photosensitizer such as thioxanthone, phenothiazine, chlorothioxanthone, xanthone, anthracene, diphenyl anthracene and rubrene.

An example of TAS includes triphenylsulfonium tetrafluoroborate, triphenylsulfonium hexafluorophosphonate, triphenylsulfonium hexafluoroarsenate, triphenylsulfonium trifluoromethanesulfonate, triphenylsulfonium trifluoroacetate, triphenylsulfonium p-toluenesulfonate, triphenylsulfonium tetra(pentafluorophenyl)borate, 4-methoxyphenyldiphenylsulfonium tetrafluoroborate, 4-methoxyphenyldiphenylsulfonium hexafluorophosphonate, 4-methoxyphenyldiphenylsulfonium hexafluoroarsenate, 4-methoxyphenyldiphenylsulfonium trifluoromethanesulfonate, 4-methoxyphenyldiphenylsulfonium trifluoroacetate, 4-methoxyphenyldiphenylsulfonium p-toluenesulfonate, 4-methoxyphenyldiphenylsulfonium triphenylsulfonium tetra(pentafluorophenyl)borate, 4-phenylthiophenyldiphenylsulfonium tetrafluoroborate, 4-phenylthiophenyldiphenylsulfonium hexafluorophosphonate, 4-phenylthiophenyldiphenylsulfonium hexafluoroarsenate, 4-phenylthiophenyldiphenylsulfonium trifluoromethanesulfonate, 4-phenylthiophenyldiphenylsulfonium p-toluenesulfonate and 4-phenylthiophenyldiphenylsulfonium tetra(pentafluorophenyl)borate.

A specific trade name of the cationic photopolymerization initiator includes Cyracure UVI-6990, Cyracure UVI-6974 and Cyracure UVI-6992 available from U.C.C.; Adeka Optomer SP-150, SP-152, SP-170 and SP-172 available from Adeka Corporation; Photoinitiator 2074 available from Rhodia Japan Ltd.; Irgacure 250 available from Ciba Japan K. K.; UV-9380C available form GE silicones Inc.; and CPI series available from San-Apro Ltd, and also includes TPS-series, TAZ-series, DPI-series, BPI-series, MDS-series, DTS-series, SI-series, PI-series, NDI-series, PAI-series, NAI-series, NI-series, DAM-series, MBZ-series, PYR-series, DNB-series and NB-series available from Midori Kagaku Co., Ltd.

A hybrid curing system in which a cationic photopolymerization initiator is added to a normal radical photopolymerization initiator can be used for the composition of the invention. An example of the radical photopolymerization initiator includes Darocure 1173 (2-hydroxy-2-methyl-1-phenylpropan-1-one), Irgacure 184 (1-hydroxycyclohexyl phenyl ketone), Irgacure 651 (2,2-dimethoxy-1,2-diphenylethan-1-one), Irgacure 500, Irgacure 2959, Irgacure 907, Irgacure. 369, Irgacure 1300, Irgacure 819, Irgacure 1700, Irgacure 1800, Irgacure 1850, Darocure 4265 and Irgacure 784 available from Ciba Japan K. K.

Another example of the radical photopolymerization initiator includes p-methoxyphenyl-2,4-bis(trichloromethyl)triazine, 2-(p-butoxystyryl)-5-trichloromethyl-1,3,4-oxadiazole, 9-phenylacridine, 9,10-benzphenazine, a mixture of benzophenone/Michler's ketone, a mixture of hexaarylbiimidazole/mercaptobenzimidazole, 1-(4-isopropylphenyl)-2-hydroxy-2-methylpropan-1-one, benzyldimethylketal, 2-methyl-1-[4-(methylthio)phenyl]-2-morphorinopropane-1-one, a mixture of 2,4-diethylxanthone/methyl p-dimethylaminobenzoate and a mixture of benzophenone/methyltriethanolamine.

In the invention, a thermal polymerization initiator may be used. An example of a specific trade name includes San-Aid (a main agent) SI-60, SI-80, SI-100, SI-110, SI-145, SI-150, SI-160 and SI-180, and San-Aid-San-Aid SI (an auxiliary agent) available from Sanshin Chemical Industry Co., Ltd. The initiator may be used together with a radical photopolymerization-initiator and a cationic photopolymerization initiator, or together with a radical photopolymerization initiator.

The polymerizable liquid crystal composition of the invention may include a photosensitizer. An example of the photosensitizer includes thioxanetone derivatives, Anthraquinone derivatives and naphthoquinone derivatives. A desirable example of the photosensitizer includes the following compounds (Z-1) to (Z-6). An especially desirable example of the photosensitizer includes the compound (Z-1) and the compound (Z-2). The photosensitizer can be used solely or in combination of two or more of them.

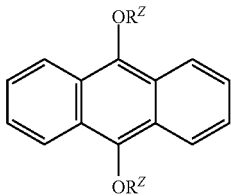

(Z-1)

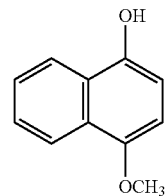

(Z-2)

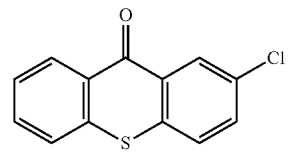

(Z-3)

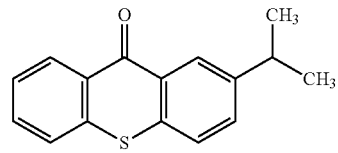

(Z-4)

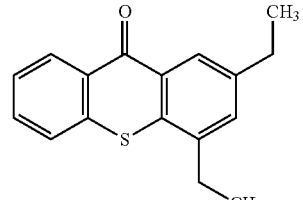

(Z-5)

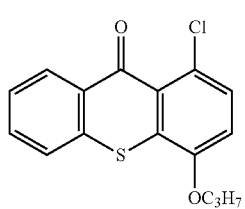

(Z-6)

In these formulas, $R^z$ is independently straight-chain alkyl having 1 to 10 carbons.

The compound (Z-1) where $R^z$ is n-butyl is available from Kawasaki Kasei Chemicals Ltd. in the trade name of Anthracure WS-1331. The compound (Z-2) is available from Kawasaki Kasei Chemicals Ltd. in the trade name of Anthracure ET-2111. The compound (Z-3) is available from Lambson Ltd. in the trade name of Speedcure CTX. The compound (Z-4) is available from Shell Chemical Co. in the trade name of Quantacure ITX. The compound (Z-5) is available from Nippon Kayaku Co., Ltd. in the trade name of Kayacure DETX-S. The compound (Z-6) is available from Lambson Ltd. in the name of Speedcure CPTX.

A combination of DAS and a photosensitizer increases sensitivity to light. A desirable mixing ratio of the photosensitizer to DAS is 10 to 200 weight parts of the photosensitizer to 100 weight parts of DAS. A more desirable mixing ratio is 20 to 100 weight parts of a photosensitizer to 100 weight parts of DAS.

An ultraviolet absorber, a light stabilizer (a radical scavenger) and an antioxidant or the like may be added for further increasing weather resistance of the polymerizable liquid crystal composition. An example of the ultraviolet absorber includes Tinuvin PS, Tinuvin P, Tinuvin 99-2, Tinuvin 109, Tinuvin 213, Tinuvin 234, Tinuvin 326, Tinuvin 328, Tinuvin 329, Tinuvin 384-2, Tinuvin 571, Tinuvin 900, Tinuvin 928, Tinuvin 1130, Tinuvin 400, Tinuvin 405, Tinuvin 460, Tinuvin 479, Tinuvin 5236, Adeka Stab LA-32, Adeka Stab LA-34, Adeka Stab LA-36, Adeka Stab LA-31, Adeka Stab 1413 and Adeka Stab LA-51. "Tinuvin" is a trade name of Ciba Japan K. K. and "Adeka Stab" is a trade name of Adeka Corporation.

An example of the light stabilizer includes Tinuvin 111FDL, Tinuvin 123, Tinuvin 144, Tinuvin 152, Tinuvin 292, Tinuvin 622, Tinuvin 770, Tinuvin 765, Tinuvin 780, Tinuvin 905, Tinuvin 5100, Tinuvin 5050, 5060, Tinuvin 5151, Chimassorb 119FL, Chimassorb 944FL, Chimassorb 944LD, Adeka Stab LA-52, Adeka Stab LA-57, Adeka Stab LA-62, Adeka Stab LA-67, Adeka Stab LA-63P, Adeka Stab LA-68LD, Adeka Stab LA-77, Adeka Stab LA-82 and Adeka Stab LA-87; Cyasorb UV-3346 available from Sun Chemical Company Ltd.; and Goodlight UV-3034 available from Goodrich Corporation. "Chimassorb" is a trade name of Ciba Japan K. K.

An example of the antioxidant includes Adeka Stab AO-20, AO-30, AO-40, AO-50, AO-60 and AO-80 available from Adeka Corporation; Sumilizer BHT, Sumilizer BBM-S and Sumilizer GA-80 available from Sumitomo Chemical Co., Ltd.; and Irganox 1076, Irganox 1010, Irganox 3114 and Irganox 245 available from Ciba Japan K. K. These commercial products may be used.

The composition of the invention may be cured by use of base-amplifying reaction under irradiation with light (K. Arimitsu, M. Miyamoto, K. Ichimura, Angew. Chem. Int. Ed, 2000, 39, 3425).

The polymerizable liquid crystal composition of the invention may include a solvent described above. Usually, the polymerizable liquid crystal composition is prepared by dissolving each component described above in a solvent. The polymerizable liquid crystal composition may be further diluted with a solvent to adjust the viscosity for an easy application. The solvent can be used solely or in combination of two or more of them. An example of a solvent includes ester-type solvents, amide-type solvents, alcohol-type solvents, ether-type solvents, glycol monoalkyl ether-type solvents, aromatic hydrocarbon-type solvents, halogenated aromatic hydrocarbon-type solvents, aliphatic hydrocarbon-type solvents, halogenated aliphatic hydrocarbon-type solvents, alicyclic hydrocarbon-type solvents, ketone-type solvent and acetate-type solvent.

A desirable example of the ester-type solvents includes alkyl acetates (for example, methyl acetate, ethyl acetate, propyl acetate, isopropyl acetate, butyl acetate, 3-methoxybutyl acetate, isobutyl acetate, pentyl acetate and isopentyl acetate), ethyl trifluoroacetate, alkyl propionate (for example, methyl propionate, methyl 3-methoxypropionate, ethyl propionate, propyl propionate and butyl propionate), alkyl butanoates (for example, methyl butanoate, ethyl butanoate, butyl butanoate, isobutyl butanoate and propyl butanoate), dialkylmalonates (for example, diethyl malonates), alkyl glycolates (for example, methyl glycolate and ethyl glycolate), alkyl lactates (for example, methyl lactate, ethyl lactate, isopropyl lactate, n-propyl lactate, butyl lactate and ethylhexyl lactate), monoacetin, γ-butyrolactone and γ-valerolactone.

A desirable example of the amide-type solvents includes N-methyl-2-pyroridone, N,N-dimethylacetoamide, N-methylpropionamide, N,N-dimethylformamide, N,N-diethylformamide, N,N-diethylacetoamide, N,N-dimethylacetoamide dimethyl acetal, N-methylcaprolactam and dimethylimidazolidinone.

A desirable example of the alcohol type solvents includes methanol, ethanol, 1-propanol, 2-propanol, 1-methoxy-2-propanol, t-butyl alcohol, sec-butyl alcohol, butanol, 2-ethylbutanol, n-hexanol, n-heptanol, n-octanol, 1-dodecanol, ethylhexanol, 3,5,5-trimethylhexanol, n-amyl alcohol, hexafluoro-2-propanol, glycerine, ethylene glycol, diethylene glycol, triethylene glycol, tetraethylene glycol, propylene glycol, dipropylene glycol, tripropylene glycol, hexylene glycol, 1,3-butanediol, 1,4-butanediol, 2,3-butanediol, 1,5-pentanediol, 2,4-pentanediol, 2,5-hexanediol, 3-methyl-3-methoxybutanol, cyclohexanol and methylcyclohexanol.

A desirable example of the ether-type solvents includes ethylene glycol dimethyl ether, diethylene glycol dimethyl ether, bis(2-propyl)ether, 1,4-dioxane and tetrahydrofuran (THF).

A desirable example of the glycol monoalkyl ether type solvents includes ethylene glycol monoalkyl ethers (for example, ethylene glycol monomethyl ether and ethylene glycol monobutyl ether), diethylene glycol monoalkyl ethers (for example, diethylene glycol monoethyl ether), triethylene glycol monoalkyl ethers, propylene glycol monoalkyl ethers (for example, propylene glycol monobutyl ether), dipropylene glycol monoalkyl ethers (for example, dipropylene glycol monomethyl ether), ethylene glycol monoalkyl ether acetates (for example, ethylene glycol monobutyl ether acetate), diethylene glycol monoalkyl ether acetates (for example, diethylene glycol monoethyl ether acetate), triethylene glycol monoalkyl ether acetates, propylene glycol monoalkyl ether acetates (for example, propylene glycol monomethyl ether acetate, propylene glycol monoethyl ether acetate and propylene glycol monobutyl ether acetate), dipropylene glycol monoalkyl ether acetates (for example, dipropylene glycol monomethyl ether acetate) and diethylene glycol methyl ethyl ether.

A desirable example of the aromatic hydrocarbon-type solvents includes benzene, toluene, xylene, mesitylene, ethylbenzene, diethylbenzene, i-propylbenzene, n-propylbenzene, t-butylbenzene, s-butylbenzene, n-butylbenzene and tetraline. A desirable example of the halogenated aromatic hydrocarbon-type solvents includes chlorobenzene. A desirable example of the aliphatic hydrocarbon-type solvents includes hexane and heptane. A desirable example of the halogenated aliphatic hydrocarbon-type solvents includes chloroform, dichloromethane, carbon tetrachloride, dichloroethane, trichloroethylene and tetrachloroethylene. A desirable example of the alicyclic hydrocarbon-type solvents includes cyclohexane and decaline.

A desirable example of the ketone-type solvents includes acetone, methyl ethyl ketone, methyl isobutyl ketone, cyclohexanone, cyclopentanone and methyl propyl ketone.

A desirable example of the acetate-type solvents includes ethylene glycol monomethyl ether acetate, propylene glycol monomethyl ether acetate, propylene glycol monoethyl ether acetate, methyl acetoacetate and 1-methoxy-2-propyl acetate.

The amide-type solvents, the aromatic hydrocarbon-type solvents, the ketone-type solvents are desirable in view of the solubility of the polymerizable liquid crystal compound. The ester-type solvents, the alcohol-type solvents, the ether-type solvents and the glycol monoalkyl ether-type solvents are desirable in consideration of the boiling points of the solvents. Although selection of the solvent is not especially limited, it is necessary to decrease drying temperature in order to avoid deformation of a supporting substrate and to prevent penetration of the solvent to the supporting substrate when a plastic substrate is used as the supporting substrate. A desirable example of the solvent used in such cases includes the aromatic hydrocarbon-type solvents, the ketone-type solvents, the ester-type solvents, the ether-type solvents, the alcohol-type solvents, the acetate-type solvents and the glycol monoalkyl ether-type solvents.

The ratio of the solvent in the polymerizable liquid crystal composition of the invention is in the range of 0% to approximately 95% by weight. A desirable ratio is in the range of approximately 40% to approximately 95% by weight in view of the solubility of the polymerizable liquid crystal compound and an optimum viscosity for applying the solution, and also in an economic view of the solvent cost, and the period of time and calorific values during evaporation of the solvent. A more desirable ratio is in the range of approximately 45% to approximately 90% by weight and an even more desirable ratio is in the range of approximately 50% to approximately 85% by weight.

Next, polymerization conditions of the composition in the invention will be explained. A polymer is obtained by polymerization of the polymerizable liquid crystal composition of the invention. Polymerization in the presence of a photopolymerization catalyst is preferable to thermal polymerization when a polymer with an excellent orientation is desired. This is because polymerization can be carried out readily under the conditions that the composition exhibits a liquid crystal state.

Desirable kinds of light used for photopolymerization include ultraviolet light, visible light and infrared light. Electromagnetic waves such as electron beams and X-rays may be used. Ultraviolet light and visible light are usually desirable. Desirable wavelengths are in the range of approximately 150 nm to approximately 500 nm. More desirable wavelengths are in the range of approximately 250 nm to approximately 450 nm and most desirable wavelengths are in the range of approximately 300 nm to approximately 400 nm. An example of a light source includes a low-pressure mercury lamp (a germicidal lamp, a chemical fluorescent lamp and a black light), a high-intensity discharge lamp (a high-pressure mercury lamp and a metal halide lamp) and a short-arc lamp (an ultra high-pressure mercury lamp, a xenon lamp and a mercury-xenon lamp). A desirable light source is a high-pressure mercury lamp. The composition may be irradiated directly with light from the light source. The composition may be irradiated with light of a specific wavelength (or specific range of wavelengths) selected by a filter. Desirable irradiation energy density is in the range of approximately 2 to approximately 5000 mJ/cm$^2$. More desirable irradiation energy density is in the range of approximately 10 to approximately 3000 mJ/cm$^2$. Most desirable irradiation energy density is in the range of approximately 100 to approximately 2000 mJ/cm$^2$. Desirable illuminance is in the range of approximately 0.1 to approximately 5000 mW/cm$^2$. More desirable illuminance is in the range of approximately 1 to approximately 2000 mW/cm$^2$. Temperature on irradiation with light is set up in order that the composition exhibits a liquid crystal phase. A desirable temperature for illuminance is approximately 100° C. or lower. An excellent orientation may not be attained at approximately 100° C. or higher because of the possibility of thermal polymerization.

The form of the polymer may be filmy, platy, granular, powdery and so forth. The polymer may be molded. A supporting substrate is generally employed to form a polymer film. The polymer film is obtained by application of the composition to the supporting substrate and then by polymerization of the paint film exhibiting a liquid crystal phase. A desirable thickness of the polymer depends on the value of optical anisotropy and usage of the polymer. Then, a desirable thickness cannot be exemplified strictly and may be in the range of approximately 0.05 to approximately 50 μm. A more desirable thickness is in the range of approximately 0.1 to approximately 20 μm. An especially desirable thickness is in the range of approximately 0.5 to approximately 10 μm. A haze value (cloudiness) of the polymer is generally approximately 1.5% or less. Transmissivity of the polymer is generally approximately 80% or more in the visible light range. Such a polymer is suitable for a thin film with optical anisotropy used for a liquid crystal display device.

An example of a supporting substrate includes triacetyl cellulose (may be referred to as TAC), polyvinyl alcohol, polyimide, polyester, polyarylate, polyetherimide, polyethylene terephthalate and polyethylene naphthalate. An example of the trade name includes "Acton" of JSR Corporation, "Zeonex" and "Zeonor" of Zeon Corporation and "Apel" of Mitsui Chemicals, Inc. The supporting substrate includes a uniaxially stretched film and a biaxially stretched film. A desirable supporting substrate is a triacetyl cellulose film. The film may be used without pre-treatment. The film may be processed by means of a surface-treatment as required, such as a saponification-treatment, a corona-treatment, an UV-ozone treatment and a plasma-treatment. An additional example includes a supporting substrate made of metal such as aluminum, iron and copper, and a supporting substrate made of glass such as alkali glass, borosilicate glass and flint.

A paint film on a supporting substrate is prepared by application of the composition as it is. The paint film is also prepared by dissolution of the composition in a suitable solvent and then by evaporation of the solvent. An application method includes spin coating, roll coating, curtain coating, flow coating, printing, micro-gravure coating, gravure coating, wire-bar coating, dip coating, spray coating, meniscus coating and casting film-forming.

In the polymerizable liquid crystal composition of the invention, factors determining orientation of liquid crystal molecules includes 1) the kinds of compounds included in a composition, 2) kinds of a supporting substrate, and 3) methods of alignment treatment. A desirable method of the alignment treatment includes oblique-deposition by use of silicon dioxide and slit etching of the surface. An especially desirable method for alignment treatment includes rubbing treatment in which the surface is rubbed with a rayon cloth in one direction. In the rubbing treatment, a supporting substrate itself may be rubbed. A supporting substrate that is coated with a thin film made from polyimide, polyvinyl alcohol or the like may be rubbed. A specific thin film on which an excellent alignment is possible without rubbing treatment is also known. A supporting substrate coated with a liquid crystal polymer having a side chain is also effective.

A classification of orientation in liquid crystal molecules includes homogeneous (parallel) orientation, homeotropic (perpendicular) orientation and hybrid orientation. The homogeneous orientation means the state in which a director is parallel to a supporting substrate and is arranged in one direction. The homeotropic orientation means the state in which a director is perpendicular to a supporting substrate. The hybrid orientation means the state in which the director is standing up from a parallel direction to a perpendicular direction to the substrate as the distance from a substrate is increased. These orientations are observed in the composition having a nematic phase and so forth.

The polymerizable liquid crystal composition of the invention may include an optically active compound. The composition including a suitable amount of an optically active compound is applied to an aligned substrate and then is polymerized, giving an optical retardation film in which a helical structure (a twist structure) is fixed. Characteristics of the resulting formed body depend on a helical pitch in the helical structure formed. The length of the helical pitch can be adjusted by the kinds and the amount of the optically active compound. Only one optically active compound may be added, or a plurality of optically active compounds may be added for the purpose of compensating temperature dependence of the helical pitch.

The selective reflection of visible light, which is the characteristics of the formed body having optical anisotropy described above, arises from the action of a helical structure on incident light, which leads to the reflection of circularly polarized light or elliptically polarized light. Characteristics of the selective reflection are represented by $\lambda = n \cdot \text{Pitch}$ ($\lambda$ is the central wavelength of selective reflection, n is an average refractive index and Pitch is a helical pitch). Hence, $\lambda$ and its bandwidth ($\Delta\lambda$) can be suitably adjusted by an amount of n or Pitch. When a helical pitch is 1/n (n is an average refractive index in a thin film with optical anisotropy) of a wavelength of light, right- or left-circularly polarized light among light with the wavelength, depending on the direction of the helix, can be reflected according to Bragg's law. This phenomenon can be utilized to, for example, a functional device that separates circularly polarized light. The direction of helix depends on configuration of an optically active compound. A desired helical direction can be induced by a suitable selection of configuration of an optically active compound. For example, a formed body having optical anisotropy can be obtained in which a helical pitch changes consecutively in the thickness-direction of the formed body according to the disclosure in JP H06-281814 A (1994), and then it can reflect light with a wide wavelength range that depends on the pitch. The bandwidth $\Delta\lambda$ should be decreased for an improvement of color purity, and $\Delta\lambda$ should be increased for broadband reflection. Furthermore, the selective reflection is greatly affected by cell thickness. The cell thickness should not be made too small for maintaining color purity. The thickness should not be made too large for maintaining orientation uniformity. Thus, a suitable adjustment of the cell thickness is necessary, and a desirable cell thickness is in the range of approximately 0.5 μm to approximately 25 μm, and a more desirable thickness is in the range of approximately 0.5 μm to approximately 5 μm.

The negative-type C-plate (negative C-plate) described in W. H. de Jeu, Physical Properties of Liquid Crystalline Materials, Gordon and Breach, New York (1980) can be prepared by making the helical pitch shorter than the wavelengths of visible light. A shorter helical pitch can be achieved by the addition of an optically active compound having a large twisting power (HTP: helical twisting power) and by increasing the amount of the compound added. The negative-type C-plate can be formed specifically when $\lambda$ is approximately 350 nm or less, and preferably approximately 200 nm or less. This negative-type C-plate serves as an optical compensation film suitable for a display device of a VAN-type, a VAC-type, an OCB-type or the like, among liquid crystal display devices.

Any optically active compound may be used if the optically active compound can induce a helical structure and can be mixed appropriately with the polymerizable liquid crystal composition that is a base. An optically active compound may be polymerizable or non-polymerizable, and an optimum compound can be added according to a purpose. The polymerizable compound is more suitable when heat resistance and solvent resistance are taken into consideration. An example of a skeleton which exhibits optical activity includes alkylene and alkenylene having one or more asymmetric carbons, or compounds having the following structures.

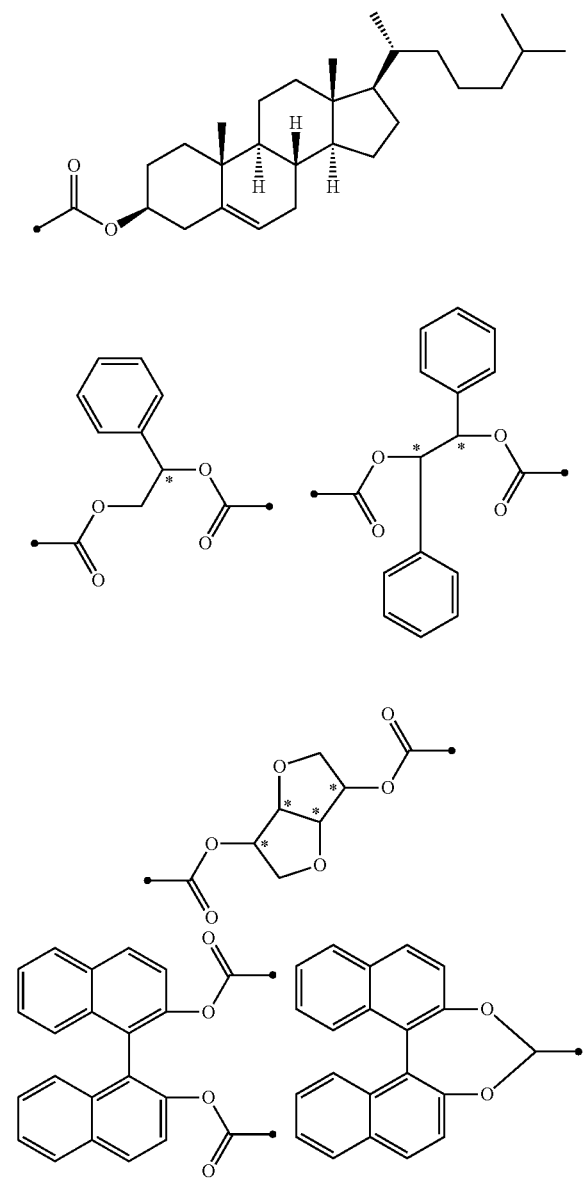

An optically active compound having a large twisting power (HTP: helical twisting power) among the compounds described above is suitable for decreasing the helical pitch. A representative example of a compound having a large twisting power is described in GB 2,298,202 A and DE 10,221,751 A1.

Next, the polymer of the invention will be explained. The polymer is formed by polymerization of the polymerizable liquid crystal composition of the invention. The polymer satisfies a plurality of characteristics such that it is colorless and transparent, photoelasticity is small, it is hard to be peeled, it has a sufficient hardness, heat resistance is large, and weather resistance is large.

Usage of the polymer is as follows. The polymer can be used as a formed body having optical anisotropy. An example of the polymer includes an optical film such as an optical retardation film (a ½ wavelength plate, a ¼ wavelength plate and so forth), an antireflection film, a selective reflection film and a viewing angle-compensation film. The polymer having an orientation such as homogenious, hybrid, homeotropic or twist can be utilized for an optical retardation film, a polarizer, a liquid crystal alignment film, an antireflection film, a selective reflection film, a viewing angle-compensation film, and so forth. Such a polymer is utilized for an optical retardation film and a viewing angle-compensation film of a liquid crystal display device, for the purpose of optical compensation. An important use example in industry includes viewing angle-compensation in the liquid crystal display device with a mode of VA, IPS, TN or MVA. The polymer can be utilized for epoxy resins having a high thermal conductivity, adhesives, synthetic polymers having mechanical anisotropy, cosmetics, an ornament, non-linear optical materials, information storage materials and so forth.

An optical retardation film, which is one of example of usage of the polymer, has a function that converts the state of polarized light. A ½ wavelength plate has a function in which the direction of oscillation in linearly polarized light is rotated 90 degrees. The composition applied to a supporting substrate so as to satisfy the equation of $d=\lambda/2\times\Delta n$, wherein d is the thickness of the composition, $\lambda$ is a wavelength and $\Delta n$ is optical anisotropy. After orientation of the composition, polymerization gives a ½ wavelength plate. On the other hand, a ¼ wavelength plate has a function in which linearly polarized light is converted to circularly polarized light or linearly polarized light is converted to circularly polarized light. In this case, the paint film of the composition may be prepared so as to satisfy the equation of $d=\lambda/4\times\Delta n$. The thickness (d) of the polymer is adjusted as follows. A paint film having an objective thickness can be obtained by a suitable selection of the concentration of the composition, applying methods, applying conditions and so forth, when a method, in which the composition is diluted with a solvent and then applied to a supporting substrate, is employed. A method that utilizes a liquid crystal cell is also desirable. The liquid crystal cell is convenient because it contains an alignment film such as polyimide. The thickness of a paint film can be adjusted by regulating the interval in a liquid crystal cell when the composition is injected to the liquid crystal cell.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted, to limit the scope of the invention.

EXAMPLES

The invention is explained by way of the following Examples, but not limited to Examples. The structures of compounds were characterized by means of their nuclear magnetic resonance spectra, infrared spectra, mass spectra and so forth. The transition temperature was expressed in the degree Celsius (° C.), and the symbols C and I stand for crystals and an isotropic liquid phase, respectively. A parenthesized value shows that the phase transition is monotropic. In Example, the symbol L represents the liter that is a unit of volume. Methods of measurement are as follows.

<Structural Determination of Compounds>

The structures of synthesized compounds were determined by means of a 500 MHz-proton NMR spectroscopy Bruker ModelDRX-500. A unit of described values is ppm and symbols s, d, t and m stand for singlet, doublet, triplet and multiplet, respectively.

<Phase Transition Temperature>

A sample was placed on a hot plate of a melting point apparatus equipped with a polarizing microscope and heated at a rate of 3° C./minute. Temperature was measured when a liquid crystal phase was transformed to another liquid crystal phase. The symbols C, N and I stand for crystals, a nematic phase and isotropic liquid, respectively. A NI-point means the maximum temperature of a nematic phase or transition temperature from a nematic phase to isotropic liquid. "C 50 N 63 I" shows that crystals were transformed to a nematic phase at 50° C. and the nematic phase was transformed to isotropic liquid at 63° C.

<Orientation of Liquid Crystal Molecules>

A polymer film (a liquid crystal alignment film) was formed on a glass substrate having a rubbed polyimide alignment film. Orientation of the polymer was determined by visual observation in the following way based on the angle dependence of transmitted light intensity.

Visual observation: A polymer film was placed between two polarizers that were arranged in the crossed Nicols and light irradiated the film surface vertically (the tilt angle was zero degrees). The change of transmitted light intensity was observed as the tilt angle of irradiation increased, for example, from zero degrees to 50 degrees. The tilted direction of irradiation was the same with that of the rubbing (a major axis direction of liquid crystal molecules). Orientation was determined to be homogenious when transmitted light in the vertical direction was maximum. The polymer functions as a A-plate, because the director of liquid crystal molecules is parallel to the glass substrate in the homogeneous orientation. On the other hand, orientation was determined to be homeotropic when transmitted light in the vertical direction was minimum, and transmitted light increased as a tilt angle was increased. The polymer functions as a C-plate, because the director of liquid crystal molecules is perpendicular to the glass substrate in the homeotropic orientation.

Measurement with a polarimeter: An Optipro polarimeter made by Shintech, Inc. was used. A polymer film was irradiated with light of wavelength at 550 nm. Retardation ($\Delta n\times d$) was measured as incident angle of light to the film surface decreased from 90 degrees.

Example 1

Synthesis of the Compound (1-2-14)

Step 1

Sodium hydride (10.8 g) was added to a mixture of diethylene glycol (39.5 g) and acetone (200 ml) under a nitrogen atmosphere and the mixture was stirred at room temperature. Allyl bromide (30.0 g) was added to the reaction mixture, which was stirred under reflux for 3 hours. Salts deposited were filtered off under reduced pressure. The filtrate was concentrated with a rotary evaporator and the residue was purified by column chromatography (silica gel; eluent:toluene/ethyl acetate=1/2 by volume), giving colorless oil [H1] (23.0 g).

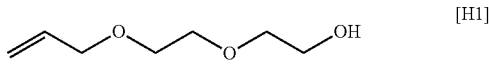

The NMR spectra of the compound [H1] were as follows.
$^1$H-NMR (CDCl$_3$; δ ppm): 5.99-5.90 (m, 1H), 5.31 (d, 1H), 5.22 (d, 1H), 4.06 (d, 2H), 3.79-3.74 (m, 2H), 3.73-3.70 (m, 2H) and 3.66-3.62 (m, 4H).

Step 2

A mixture of the compound [H1] (23.0 g), pyridine (40 ml) and toluene (100 ml) was cooled under a nitrogen atmosphere and p-toluenesulfonyl chloride (45.0 g) was added thereto and stirred at room temperature for 16 hours. Salts deposited were filtered off under reduced pressure. Water (100 ml) and pyridine (40 ml) were added to the filtrate and the mixture was stirred at 40° C. for 2 hours. The product was extracted and the extract was washed sequentially with 2N-hydrochloric acid, a saturated aqueous solution of sodium hydrogencarbonate and water, and dried over anhydrous magnesium sulfate. The solvent was distilled off under reduced pressure, giving crude colorless oil [H2] (57.5 g).

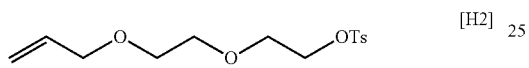

Step 3

A mixture of the compound [H2] (27.0 g), ethyl 4-hydroxybenzoate (29.9 g), potassium carbonate (37.3 g) and acetone (200 ml) was heated to reflux under a nitrogen atmosphere with stirring for 6 hours. Salts deposited were filtered off under reduced pressure. The filtrate was concentrated with a rotary evaporator, and toluene (200 ml) and water (200 ml) were added to the residue, and then the product was extracted. The extract was washed sequentially with a saturated aqueous solution of sodium hydrogencarbonate and water, and dried over anhydrous magnesium sulfate. The solvent was distilled off under reduced pressure, giving crude colorless oil [H3] (19.7 g).

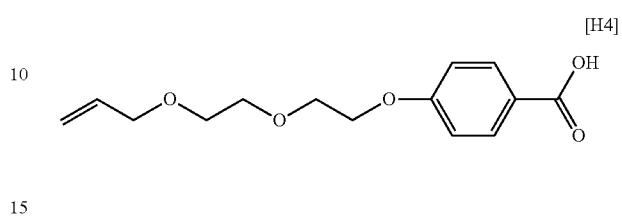

Step 4

A mixture of the compound [H3] (19.7 g), sodium hydroxide (5.4 g), water (150 ml) and ethanol (150 ml) was heated to reflux under a nitrogen atmosphere with stirring for 6 hours. The solvent was distilled off under reduced pressure and the residue was poured into 3N-hydrochloric acid. Ethyl acetate (200 ml) was added thereto and the product was extracted. The extract was washed with water and dried over anhydrous magnesium sulfate. Recrystallization from toluene gave colorless crystals of the compound (H4) (14.6 g).

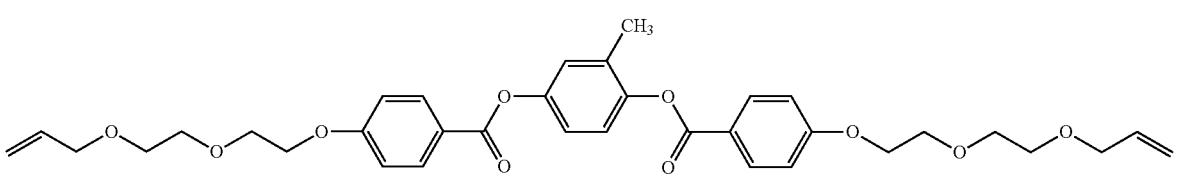

The NMR spectra of the compound [H4] were as follows.
$^1$H-NMR (CDCl$_3$; δ ppm): 8.10 (d, 2H), 7.20 (d, 2H), 6.05-5.98 (m, 1H), 5.41 (d, 1H), 5.28 (d, 1H), 4.04 (d, 2H), 3.82-3.76 (m, 2H), 3.74-3.71 (m, 2H) and 3.68-3.63 (m, 4H).

Step 5

A mixture of the compound [H4] (30.0 g), methylhydroquinone (6.8 g), dimethylaminopyridine (2.8 g) and dichloromethane (300 ml) was cooled under a nitrogen atmosphere and DCC (25.6 g) was added thereto, and then the mixture was stirred at room temperature for 16 hours. Precipitates were filtered off under reduced pressure and water was added to the filtrate, separating an organic layer. The organic layer was washed sequentially with 2N-hydrochloric acid and water, and then dried over magnesium sulfate. The solvent was distilled off under reduced pressure and the residue was purified by column chromatography (silica gel, eluent:toluene/ethyl acetate=1/1 by volume), and by recrystallization from methanol, giving colorless crystals of the compound [H5] (28.0 g).

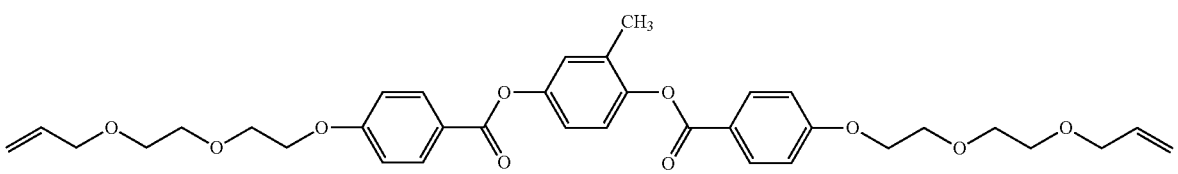

The phase transition temperature and NMR spectra of the compound [H5] were as follows.
C 53 N 59 I.
$^1$H-NMR (CDCl$_3$; δ ppm): 8.16 (d, 2H), 8.14 (d, 2H), 7.17 (d, 1H), 7.13 (d, 1H), 7.10-7.06 (m, 1H), 7.02 (d, 2H), 7.00 (d, 2H), 5.98-5.89 (m, 1H), 5.29 (d, 2H), 5.20 (d, 2H), 4.26-4.22 (m, 4H), 4.05 (d, 4H), 3.92 (t, 4H), 3.78-3.74 (m, 4H), 3.67-3.63 (m, 4H) and 2.24 (m, 3H).

Step 6

A mixture of the compound [H5] (23.0 g) and dichloromethane (230 ml) was cooled under a nitrogen atmosphere and m-chloroperbenzoic acid (21.6 g) was added thereto, and then the mixture was stirred for 16 hours. Precipitates were removed by filtration under reduced pressure and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent:toluene/ethyl acetate=1/2 by volume), and by recrystallization from ethanol, giving colorless crystals of the compound (1-2-14) (16.8 g).

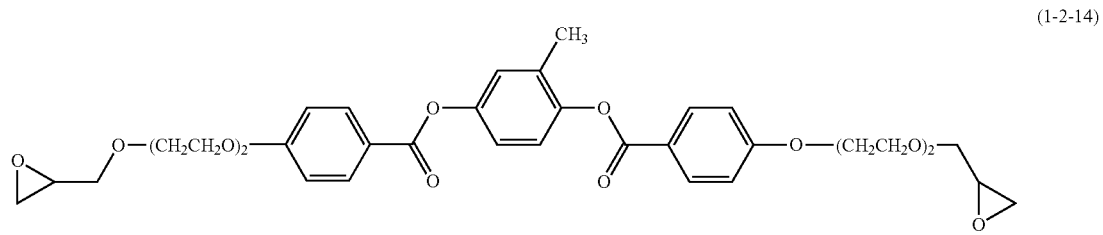

(1-2-14)

The phase transition temperature and NMR spectra of the compound (1-2-14) were as follows.

C 68 N 42 I.

$^1$H-NMR (CDCl$_3$; δ ppm): 8.16 (d, 2H), 8.14 (d, 2H), 7.17 (d, 1H), 7.13 (s, 1H), 7.08 (d, 1H), 7.02 (d, 2H), 7.00 (d, 1H), 4.28-4.20 (m, 4H), 3.95-3.87 (m, 4H), 3.83 (d, 2H), 3.80-3.66 (m, 8H), 3.47-3.41 (m, 2H), 3.20-3.15 (m, 2H), 2.80 (t, 2H), 2.63-2.60 (m, 2H) and 2.24 (s, 3H).

Example 2

Synthesis of the Compound (1-2-27)

Step 1

A mixture of the compound [H2] (15.0 g), 4,4'-biphenol (27.9 g), potassium carbonate (31.1 g), DMF (200 ml) was stirred at 90° C. for 6 hours. Ethyl acetate (500 ml) was added thereto and precipitates were filtered off under reduced pressure. Water (300 ml) was added to the filtrate and the product was extracted. The extract was washed sequentially with 2N-hydrochloric acid, 2N-sodium hydroxide solution and water, dried over anhydrous magnesium sulfate. The solvent was distilled off and the residue was purified by column chromatography (silica gel, eluent:toluene/ethyl acetate=2/1 by volume), giving colorless oil [H6] (24.9 g).

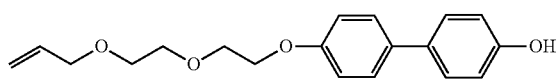

[H6]

The NMR spectra of the compound [H6] were as follows.
$^1$H-NMR, (CDCl$_3$; δ ppm): 7.68-7.62 (m, 4H), 7.05 (d, 2H), 6.86 (d, 2H), 6.06-5.99 (m, 1H), 5.42 (d, 1H), 5.28 (d, 1H), 4.08 (d, 2H), 3.79-3.74 (m, 2H), 3.72-3.69 (m, 2H) and 3.65-3.59 (m, 4H).

Step 2

A mixture of the compound [H4] (6.4 g) and the compound [H6] (7.5 g), dimetylaminopyridine (0.3 g) and dichloromethane (60 ml) was cooled under a nitrogen atmosphere and DCC (5.2 g) was added thereto, and then the mixture was stirred at room temperature for 16 hours. Precipitates were filtered off under reduced pressure and water was added to the filtrate, separating an organic layer. The organic layer was washed sequentially with 2N-hydrochloric acid and water and dried over magnesium sulfate. The solvent was distilled off under reduced pressure and the residue was purified by column chromatography (silica gel, eluent:toluene/ethyl acetate=4/1 by volume), and by recrystallization from methanol, giving colorless crystals of the compound [H7] (10.3 g).

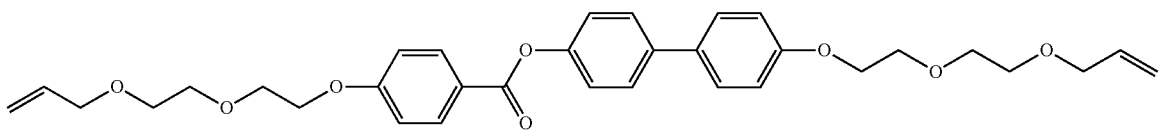

[7]

The phase transition temperature and NMR spectra of the compound [H7] were as follows.

C 87 N 102 I.

$^1$H-NMR (CDCl$_3$; δ ppm): 8.11 (d, 2H), 7.86 (d, 2H), 7.68 (d, 2H), 7.23 (d, 2H), 7.18-7.02 (m, 4H), 6.21-5.98 (m, 2H), 5.42 (d, 2H), 5.28 (d, 2H), 4.31 (t, 4H), 4.04 (d, 4H), 3.79 (t, 4H) and 3.58-3.50 (m, 8H).

Step 3

A mixture of the compound [H7] (10.3 g) and dichloromethane (100 ml) was cooled and m-choloroperbenzoic acid (29.2 g) was added under a nitrogen atmosphere and stirred at room temperature for 16 hours. Precipitates were removed by filtration under reduced pressure and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent: 2/1 by volume), and by recrystallization from ethanol, giving colorless crystals of the compound (1-2-27) (3.8 g).

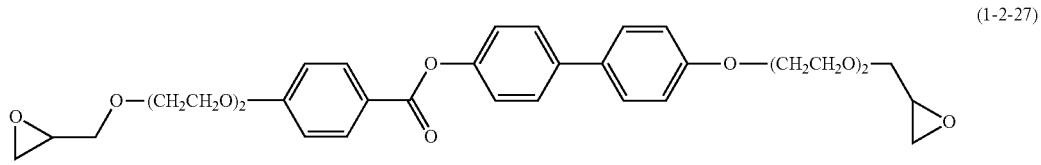

(1-2-27)

The phase transition temperature and NMR spectra of the compound (1-2-27) were as follows.

C 89 N 102 I.

$^1$H-NMR (CDCl$_3$; δ ppm): 8.19 (d, 2H), 7.61 (d, 2H), 7.54 (d, 2H), 7.28 (d, 2H), 7.03 (t, 4H), 4.26 (t, 2H), 4.22 (t, 2H), 3.96-3.91 (m, 4H), 3.88-3.83 (m, 2H), 3.81-3.70 (m, 8H), 3.50-3.43 (m, 2H), 3.23-3.18 (m, 2H), 2.85-2.81 (m, 2H) and 2.67-2.63 (m, 2H).

Example 3

Synthesis of the Compound (1-2-24)

Step 1

The compound [H2] (45.0 g) was added to a mixture of hydroquinone (82.5 g), potassium hydroxide (84.1 g) and methanol (500 ml) with stirring at 50° C. under a nitrogen atmosphere and the mixture was heated under reflux with stirring for 3 hours. The solvent was distilled off under reduced pressure and the residue was added to 2N-hydrochloric acid, neutralizing it. Toluene was added thereto and the product was extracted. The extract was washed with water, and dried over anhydrous magnesium sulfate. The solvent was distilled off under reduced pressure and the residue was purified by column chromatography (silica gel, eluent:toluene/ethyl acetate=2/1 by volume), giving colorless oil [H8] (12.8 g).

[H8]

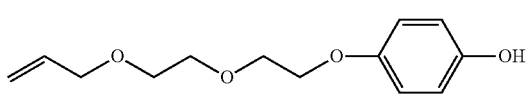

The NMR spectra of the compound [H8] were as follows.

$^1$H-NMR (CDCl$_3$; δ ppm): 7.00 (d, 2H), 6.82 (d, 2H), 6.06-5.99 (m, 1H), 5.41 (d, 1H), 5.25 (d, 1H), 4.08 (d, 2H), 3.79-3.74 (m, 2H), 3.72-3.69 (m, 2H) and 3.65-3.59 (m, 4H).

Step 2

A mixture of the compound [H8] (10.0 g), cyclohexanedicarboxylic acid (3.5 g), dimethylaminopyridine (0.3 g) and dichloromethane (90 ml) was cooled under a nitrogen atmosphere and DCC (8.7 g) was added thereto, and then the mixture was stirred at room temperature for 16 hours. Precipitates were filtered off under reduced pressure and water was added to the filtrate, separating an organic layer. The organic layer was washed sequentially with 2N-hydrochloric acid and water and dried over magnesium sulfate. The solvent was distilled off under reduced pressure and the residue was purified by column chromatography (silica gel, eluent:toluene/ethyl acetate=2/1 by volume), and by recrystallization from methanol, giving colorless crystals of the compound [H9] (12.1 g).

[H9]

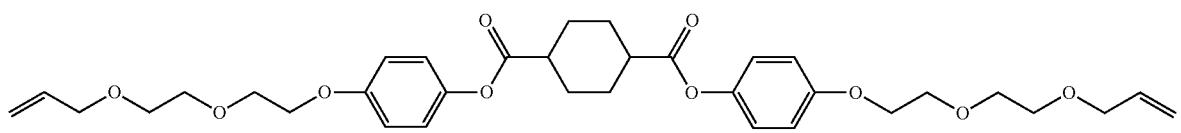

The phase transition temperature and NMR spectra of the compound [H9] were as follows.

C 59 N 78 I.

$^1$H-NMR (CDCl$_3$; δ ppm): 6.96 (t, 4H), 6.88 (d, 4H), 6.11-6.02 (m, 2H), 5.42 (d, 2H), 5.28 (d, 2H), 4.31 (t, 4H), 4.04 (d, 4H), 3.79 (t, 4H), 3.56-3.51 (m, 8H), 2.28-2.17 (m, 2H), 1.84-1.76 (m, 4H) and 1.59-1.50 (m, 4H).

Step 3

A mixture of the compound [H9] (10.0 g) and dichloromethane (100 ml) was cooled under a nitrogen atmosphere and m-chloroperbenzoic acid (33.8 g) was added thereto, and then the mixture was stirred at room temperature for 16 hours. Precipitates were removed by filtration under reduced pressure. The filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent:toluene/ethyl acetate=1/4 by volume), and by recrystallization from ethanol, giving colorless crystals of the compound (1-2-24) (3.7 g).

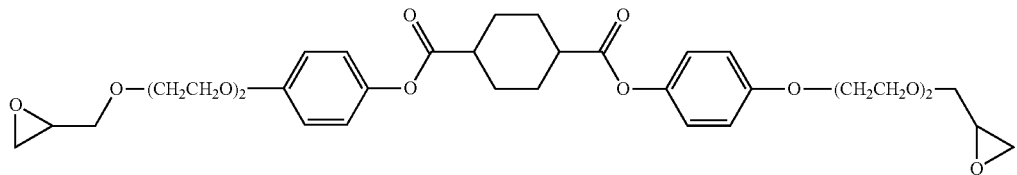

(1-2-24)

The phase transition temperature and NMR spectra of the compound (1-2-24) were as follows.

C 68 N 72 I.

$^1$H-NMR (CDCl$_3$; δ ppm): 6.99 (t, 4H), 6.93 (d, 4H), 4.15 (t, 4H), 3.88 (t, 4H), 3.86-3.81 (m, 2H), 3.79-3.3.68 (m, 8H), 3.49-3.3.43 (m, 2H), 3.22-3.17 (m, 2H), 2.82 (t, 2H), 2.65-2.55 (m, 4H), 2.29 (d, 4H) and 1.73-1.62 (m, 6H).

Example 4

Synthesis of the Compound (1-2-33)

Step 1

The compound [H10] was synthesized by a method similar to that of the synthesis of the compound [H4].

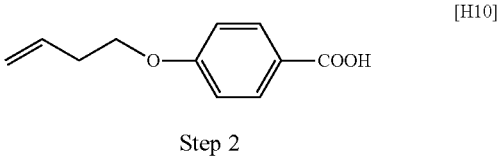

[H10]

Step 2

A mixture of the compound [H10] (6.0 g), the compound [H5] (9.8 g), dimethylaminopyridine (0.4 g) and dichloromethane (70 ml) was cooled under a nitrogen atmosphere and then DCC (6.4 g) was added thereto and the mixture was stirred at room temperature for 16 hours. Precipitates were filtered off under reduced pressure and water was added to the filtrate, separating an organic layer. The organic layer was washed sequentially with 2N-hydrochloric acid and water and dried over magnesium sulfate. The solvent was distilled off under reduced pressure and the residue was purified by column chromatography (silica gel, eluent:toluene/ethyl acetate=4/1 by volume), and by recrystallization from methanol, giving colorless crystals of the compound [H11] (13.7 g).

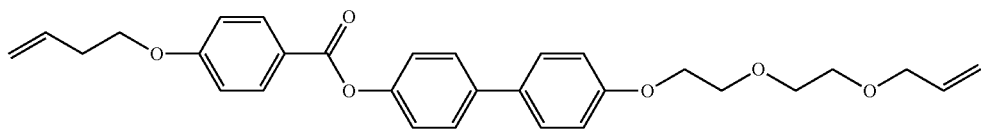

[H11]

The phase transition temperature and NMR spectra of the compound [H11] were as follows.

C 117 N 154 I.

$^1$H-NMR (CDCl$_3$; δ ppm): 8.14 (d, 2H), 7.86 (d, 2H), 7.72 (d, 2H), 7.23 (d, 2H), 7.14 (d, 2H), 7.05 (d, 2H), 6.09-6.01 (m, 1H), 5.84-5.75 (m, 1H), 5.45-5.26 (m, 2H), 5.11-5.00 (m, 2H), 4.31 (t, 2H), 4.08-3.94 (m, 4H), 3.79 (t, 2H), 3.59-3.52 (m, 4H) and 2.45-2.39 (m, 2H).

Step 3

A mixture of the compound [H11] (13.7 g) and dichloromethane (120 ml) was cooled under a nitrogen atmosphere and m-chloroperbenzoic acid (59.6 g) wad added thereto, and then the mixture was stirred at room temperature for 16 hours. Precipitates were filtered off under reduced pressure, and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent:toluene/ethyl acetate=1/1 by volume), and by recrystallization from ethanol, giving colorless crystals of the compound (1-2-33) (0.7 g).

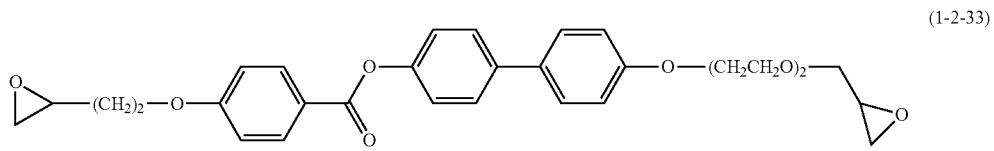

(1-2-33)

The phase transition temperature and NMR spectra of the compound (1-2-33) were as follows.

C 118 N 160 I.

$^1$H-NMR (CDCl$_3$; δ ppm): 8.18 (d, 2H), 7.58 (d, 2H), 7.51 (d, 2H), 7.25 (d, 2H), 7.03-6.98 (m, 4H), 4.27-4.17 (m, 4H), 3.90 (t, 2H), 3.85-3.81 (m, 1H), 3.79-3.68 (m, 4H), 3.48-3.42 (m, 1H), 3.21-3.16 (m, 2H), 2.86 (t, 1H), 2.80 (t, 1H), 2.64-2.59 (m, 2H), 2.24-2.16 (m, 1H) and 2.01-1.93 (m, 1H).

Example 5

Synthesis of the Compound (1-2-32)

Step 1

The compound [H12] was synthesized by a method similar to that of the synthesis of the compound.

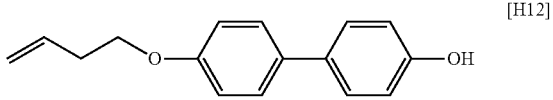 [SMILES: C=CCCOc1ccc(-c2ccc(O)cc2)cc1]

[H12]

The NMR spectra of the compound [H12] were as follows.

$^1$H-NMR (CDCl$_3$; δ ppm): 7.68 (m, 2H), 7.62 (m, 2H), 7.05 (d, 2H), 6.86 (d, 2H), 5.86-5.82 (m, 1H), 5.07 (d, 1H), 5.02 (d, 1H), 3.98 (t, 2H) and 2.45-2.39 (m, 2H).

Step 2

A mixture of the compound [H12] (5.5 g), the compound [H4] (6.7 g), dimethylaminopyridine (0.3 g) and dichloromethane (60 ml) was cooled under a nitrogen atmosphere and DCC (5.5 g) was added thereto, and then the mixture was stirred at room temperature for 16 hours. Precipitates were filtered off under reduced pressure and water was added to the filtrate, separating an organic layer. The organic layer was washed sequentially with 2N-hydrochloric acid and water and dried over magnesium sulfate. The solvent was distilled off under reduced pressure and the residue was purified by column chromatography (silica gel, eluent:toluene/ethyl acetate=5/1 by volume), and by recrystallization from methanol, giving colorless crystals of the compound [H13] (10.5 g).

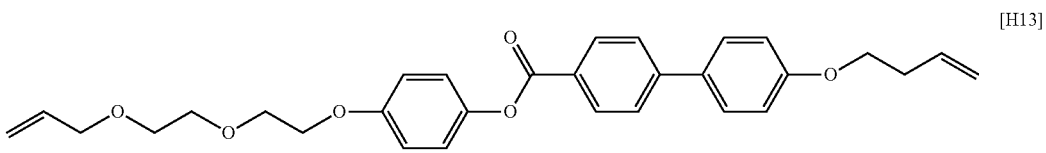 [SMILES: C=CCCOc1ccc(-c2ccc(C(=O)Oc3ccc(OCCOCCOCC=C)cc3)cc2)cc1]

[H13]

The phase transition temperature and NMR spectra of the compound [13] were as follows.

C 102 N 154 I.

$^1$H-NMR (CDCl$_3$; δ ppm): 8.11 (d, 2H), 7.79 (d, 2H), 7.68 (d, 2H), 7.26 (d, 2H), 7.09-7.02 (m, 4H), 6.11-6.02 (m, 1H), 5.87-5.78 (m, 1H), 5.48-5.42 (m, 2H), 5.14-5.05 (m, 2H), 4.31 (t, 2H), 4.08-3.94 (m, 4H), 3.79 (t, 2H), 3.58-3.54 (m, 4H) and 2.38-2.34 (m, 2H).

Step 3

A mixture of the compound [H13] (10.5 g.) and dichloromethane (100 ml) was cooled under a nitrogen atmosphere and m-chloroperbenzoic acid (34.2 g) wad added thereto, and then the mixture was stirred at room temperature for 16 hours. Precipitates were removed by filtration under reduced pressure, and the filtrate was washed sequentially with an aqueous 10% solution of sodium hydrogen sulfite, an aqueous 3% solution of sodium hydroxide and water, and dried over anhydrous magnesium sulfate. The solvent was distilled off under reduced pressure and the residue was purified by column chromatography (silica gel, eluent:toluene/ethyl acetate=3/2 by volume), and by recrystallization from ethanol, giving colorless crystals of the compound (1-2-32) (3.5 g).

(1-2-32)

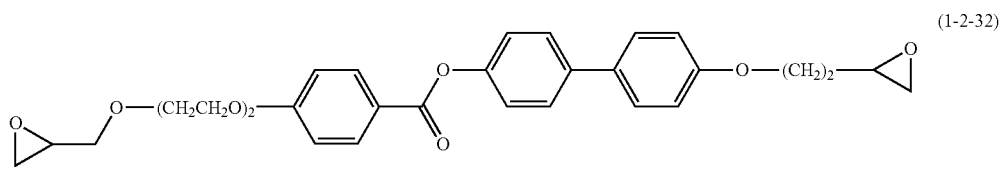

The phase transition temperature and NMR spectra of the compound (1-2-32) were as follows.

C 102 N 157 I.

$^1$H-NMR (CDCl$_3$; δ ppm): 8.19 (d, 2H), 7.61 (d, 2H), 7.55 (d, 2H), 7.27 (d, 2H), 7.06-6.99 (m, 4H), 4.26 (t, 2H), 4.23-4.15 (m, 2H), 3.94 (t, 2H), 3.88-3.84 (m, 1H), 3.82-3.69 (m, 4H), 3.49-3.44 (m, 1H), 3.23-3.18 (m, 2H), 2.87 (t, 1H), 2.83 (t, 1H), 2.66-2.62 (m, 2H), 2.21-2.13 (m, 1H) and 2.04-1.96 (m, 1H).

Example 6

Synthesis of the Compound (1-3-55)

Step 1

A mixture of 2-bromoethyl ether (50.0 g), toluene (200 ml), water (200 ml), 3-ethyl-3-oxetanemethanol (16.7 g), sodium hydroxide (28.7 g) and tetrabutylammonium bromide (4.6 g) was stirred under a nitrogen atmosphere at 100° C. for 3 hours. The organic layer was separated and washed sequentially with a saturated aqueous solution of sodium hydrogencarbonate and brine, and dried over anhydrous magnesium sulfate. The solvent was concentrated with a rotary evaporator, giving crude colorless oil [H14] (16.3 g).

[H14]

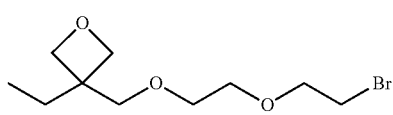

Step 2

A mixture of the compound [H14] (16.3 g), ethyl 4-hydroxybenzoate (13.2 g), potassium carbonate (10.1 g) and DMF (200 ml) was stirred under a nitrogen atmosphere at 80° C. for 6 hours. Ethyl acetate (200 ml) and water (200 ml) were added to the reaction mixture, separating an organic layer. The organic layer was washed sequentially with a saturated aqueous solution of sodium hydrogencarbonate and water, and dried over anhydrous magnesium sulfate. The solvent was distilled off under reduced pressure, giving crude colorless oil [H15] (17.9 g).

[H15]

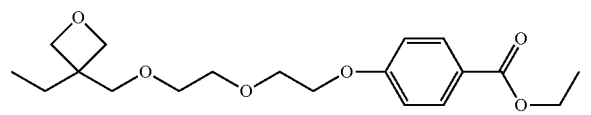

Step 3

A mixture of the compound [H15] (17.9 g), sodium hydroxide (2.9 g), water (100 ml) and methanol (100 ml) was heated under reflux with stirring for 3 hours under a nitrogen atmosphere. The solvent was distilled off under reduced pressure and the residue was poured into 3N-hydrochloric acid. Ethyl acetate (200 ml) was added thereto and the product was extracted. The extract was washed with water, and dried over anhydrous magnesium sulfate. Recrystallization from heptane gave colorless crystals of the compound (H16) (14.7 g).

[H16]

The spectra of the compound [H16] were as follows.

$^1$H-NMR (CDCl$_3$; δ ppm): 8.10 (d, 2H), 7.20 (d, 2H), 4.39-4.31 (m, 4H), 4.14 (s, 2H), 3.82-3.76 (m, 4H), 3.58-3.52 (m, 4H), 1.69 (m, 2H) and 1.03 (t, 3H).

Step 4

A mixture of the compound [H16] (14.7 g), biphenol (4.2 g), dimethylamminopyridine (1.1 g) and dichloromethane (150 ml) was cooled under a nitrogen atmosphere and DCC (10.3 g) was added thereto, and then the mixture was stirred at room temperature for 16 hours. Precipitates were filtered off under reduced pressure and water was added to the filtrate, separating an organic layer. The organic layer was washed sequentially with 2N-hydrochloric acid and water and dried over magnesium sulfate. The solvent was distilled off under reduced pressure and the residue was purified by column chromatography (silica gel, eluent:toluene/ethyl acetate=1/1 by volume), and by recrystallization from methanol, giving colorless crystals of the compound (1-3-55) (4.2 g).

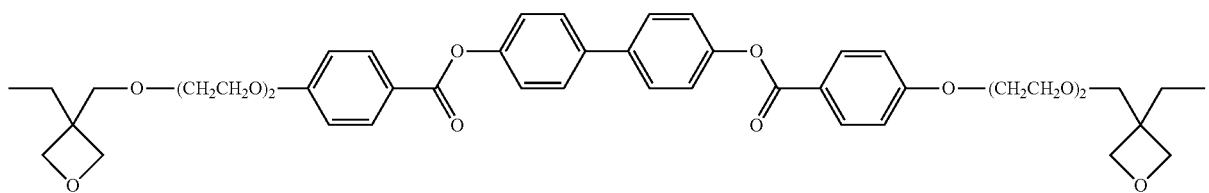
(1-3-55)
The NMR spectra of the compound (1-3-55) were as follows.
$^1$H-NMR (CDCl$_3$; δ ppm): 8.11 (d, 4H), 7.86 (d, 4H), 7.23 (d, 4H), 7.14 (d, 4H), 4.39-4.31 (m, 8H), 4.14 (s, 4H), 3.41-3.75 (m, 8H), 3.62-3.56 (m, 8H), 1.78 (m, 4H) and 1.05 (t, 6H).
Component compounds excluding the compound (1) used in Examples of the following polymerizable liquid crystal compositions are as follows.
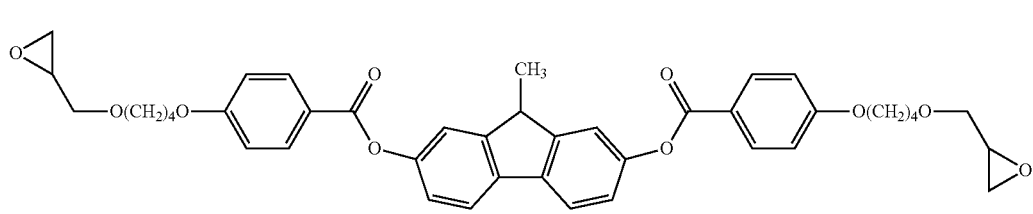
(M1-1-1)
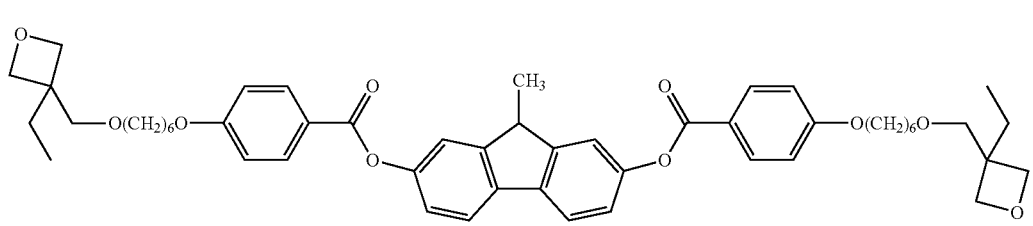
(M1-1-2)
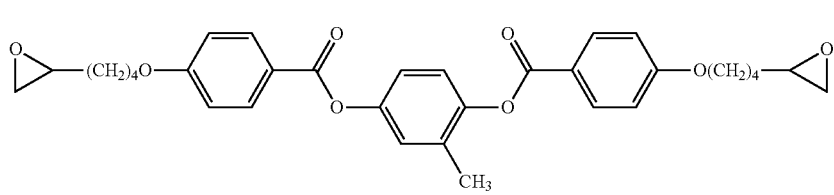
(M1-2-1)
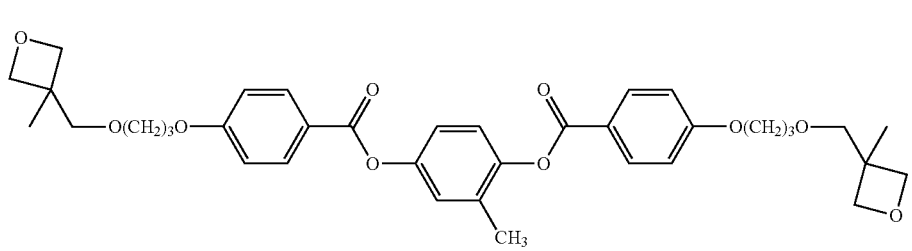
(M1-2-2)
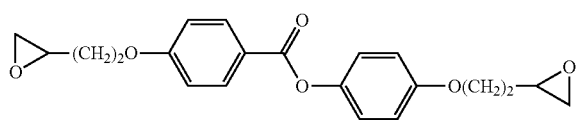
(M3-1-1)
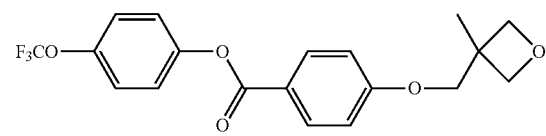
(M4-8-1)

-continued

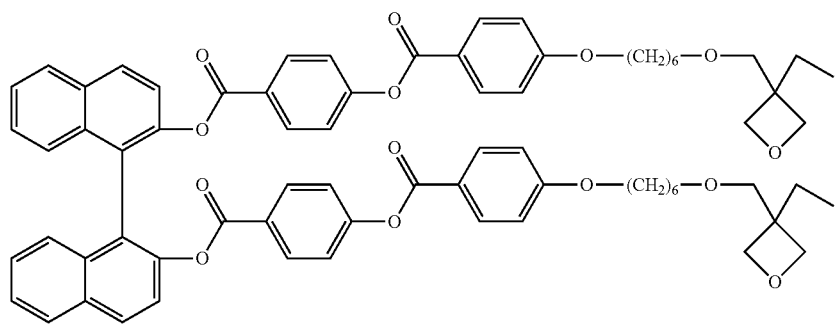
(Op-1)

Example 7

A mixture of the compound (1-2-14) and the compound (M3-1-1) at the weight ratio of 70/30 was dissolved in a mixed solvent (PGMEA/MMP=5/5) and a solution in which the concentration of the compounds was 30% by weight was prepared. After the solution had been allowed to stand at room temperature for 5 days, no crystals deposited.

Example 8

A mixture of the compound (1-2-32), the compound (1-3-55) and the compound (M3-1-1) was dissolved in cyclopentanone at the weight ratio of 25/25/50 and a solution in which the concentration of the compounds was 25% by weight was prepared. After the solution had been allowed to stand at room temperature for 5 days, no crystals deposited.

Comparative Example 1

A solution was prepared by the method described in Example 7 except that the compound (1-2-14) was replaced by the compound (M2-2-1). After the solution had been allowed to stand at room temperature for 1 day, crystals deposited.

Example 9

A fluorine-based nonionic surfactant FTX-218 (Neos Company Limited) at the weight ratio of 0.002 and a polymerization initiator CPI-110P (San-Apro Ltd.) at the weight ratio of 0.02 were added to the composition obtained in Example 7, based on the amount of the composition. The solution was applied with a spin-coater to a glass substrate having a rubbed polyimide alignment film. The glass substrate was placed on a hot plate at 70° C. for 120 seconds, evaporating the solvent and forming a paint film. Then, the paint film was photopolymerized in air at room temperature for 30 seconds, with irradiance of 30 mW/cm$^2$ (a central wavelength at 365 nm) using a 250 W-ultra high-pressure mercury lamp. The formed thin film was fixed in a homogeneous orientation and exhibited optical properties of an A-plate.

Example 10

A mixture of the compound (1-2-27)/the compound (M$_7$1-1-1)/the compound (M3-1-1) at the weight ratio of 30/30/40 was dissolved in a mixed solvent (PGMEA/MMP=5/5), and a solution in which the concentration of the compounds was 20% by weight was prepared. To the solution, a fluorine-based nonionic surfactant FTX-218 (Neos Company Limited) at the weight ratio of 0.002 and a polymerization initiator CPI-110P (San-Apro Ltd.) at the weight ratio of 0.02 were added on the basis of the amount of the composition. The thin film formed from the solution according to the method in Example 9 exhibited optical properties of an A-plate.

Example 11

A mixture of the compound (1-2-24)/the compound (M-1-1-2)/the compound (M4-8-1) at the weight ratio of 30/10/60 was dissolved in cyclopentanone, and a solution in which the concentration of the compounds was 20% by weight was prepared. To the solution, a polymerization initiator CPI-110P (San-Apro Ltd.) at the weight ratio of 0.02 was added on the basis of the composition. The solution was applied to a glass substrate with a spin-coater, forming a thin film. The glass substrate was placed on a hot plate at 70° C. for 120 seconds, evaporating the solvent and forming a paint film. Then, the paint film was photopolymerized in air at room temperature for 30 seconds, with irradiance of 30 mW/cm$^2$ (a central wavelength at 365 nm) using a 250 W-ultra high-pressure mercury lamp. The formed thin film was fixed in a homogeneous orientation and exhibited optical properties of a C-plate.

Example 12

A mixture of the compound (1-2-33)/the compound (M1-1-1)/the compound (M-2-2-1)/the compound (M3-1-1)/the compound (Op-1) at the weight ratio of 10/10/10/60/10 was dissolved in a mixed solvent (PGMEA/cyclopentanone=3/7), and a solution in which the concentration of the compounds was 20% by weight was prepared. To the solution, a fluorine-based nonionic surfactant FTX-218 (Neos Company Limited) at the weight ratio of 0.002 and a polymerization initiator CPI-110P (San-Apro Ltd.) at the weight ratio of 0.02 were added on the basis of the amount of the composition. The thin film formed from the solution according to the method in Example 9 exhibited optical properties of a negative C-plate.

Example 13

A mixture of the compound (1-2-14)/the compound (1-3-55)/the compound (M-2-2-1)/the compound (M3-1-1)/the compound (Op-1) at the weight ratio of 10/10/10/65/5 was dissolved in methyl ethyl ketone, and a solution in which the concentration of the compounds was 20% by weight was prepared. To the solution, Polyflow No. 75 (Kyoeisha Chemical Co., Ltd.) at the weight ratio of 0.002 and a polymerization initiator CPI-110P (San-Apro Ltd.) at the weight ratio of 0.02 were added. The thin film formed from the solution according to the method in Example 9 exhibited selective reflection of visible light.

Example 14

A mixture of the compound (1-2-33)/the compound (M-2-2-2)/the compound (M4-8-1)/the compound (M3-1-1) at the weight ratio of 20/10/5/65 was dissolved in toluene, and a solution in which the concentration of the compounds was 20% by weight was prepared. To the solution, a polymerization initiator DTS-102 (Midori Kagaku Co., Ltd.) at the weight ratio of 0.02 was added on the basis of the total amount of the composition. The thin film formed from the solution according to the method in Example 9 exhibited optical properties of a negative O-plate.

INDUSTRIAL APPLICABILITY

The invention concerns a polymerizable liquid crystal compound that is used for a component of the polymerizable liquid crystal composition. The polymer of the invention can be utilized, for example, for an element of a liquid crystal display device, such as an optical retardation plate, a polarizer, a selective reflection film, a brightness enhancement film and a viewing angle-compensation film.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

What is claimed is:

1. A polymerizable liquid crystal compound represented by formula (1)

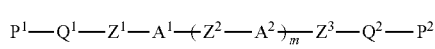
(1)

wherein $A^1$ and $A^2$ are each independently 1,4-cyclohexylene or 1,4-phenylene, and one or two hydrogens in the 1,4-phenylene may be replaced by fluorine or methyl;

$Z^1$ and $Z^3$ are a single bond; $Z^2$ is a single bond, —COO—, or —OCO—;

m is 1 or 2;

$Q^1$ and $Q^2$ are each independently —O(CH$_2$ CH$_2$ O)$_2$—, —O(CH$_2$ CH$_2$ O)$_3$—, —O(CH$_2$ CH$_2$ CH$_2$ O)— or —O(CH$_2$ CH$_2$ CH$_2$ O)$_3$; and $P^1$ and $P^2$ are a polymerizable group represented by formula (2-2) and R is hydrogen:

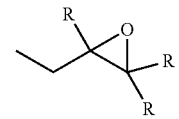
(2-2)

2. A polymerizable liquid crystal composition comprising at least one of compounds according to claim 1.

3. An optically anisotropic film formed by polymerization of at least one of compounds according to claim 1.

4. The optically anisotropic film according to claim 3, wherein the film has optical properties of an A-plate.

5. The optically anisotropic film according to claim 3, wherein the film has optical properties of a C-plate.

6. The optically anisotropic film according to claim 3, wherein the film has optical properties of a negative C-plate.

7. The optically anisotropic film according to claim 3, wherein the film has optical properties of an O-plate.

8. A liquid crystal display device that comprises the optically anisotropic film according to claim 3.

* * * * *